US011713467B2

(12) United States Patent
Campbell et al.

(10) Patent No.: US 11,713,467 B2
(45) Date of Patent: Aug. 1, 2023

(54) PLASMID CONSTRUCTS FOR HETEROLOGOUS PROTEIN EXPRESSION AND METHODS OF USE

(71) Applicant: OncoSec Medical Incorporated, Pennington, NJ (US)

(72) Inventors: Jean Campbell, Seattle, WA (US); David A. Canton, Poway, CA (US); Robert H. Pierce, San Diego, CA (US)

(73) Assignee: OncoSec Medical Incorporated, Ewing, NJ (US)

(*) Notice: Subject to any disclaimer, the term of this patent is extended or adjusted under 35 U.S.C. 154(b) by 926 days.

(21) Appl. No.: 16/062,983

(22) PCT Filed: Dec. 16, 2016

(86) PCT No.: PCT/US2016/067388

§ 371 (c)(1),
(2) Date: Jun. 15, 2018

(87) PCT Pub. No.: WO2017/106795

PCT Pub. Date: Jun. 22, 2017

(65) Prior Publication Data

US 2019/0153469 A1 May 23, 2019

Related U.S. Application Data

(60) Provisional application No. 62/375,245, filed on Aug. 15, 2016, provisional application No. 62/269,702, filed on Dec. 18, 2015.

(51) Int. Cl.

| | |
|---|---|
| ***C12N 15/85*** | (2006.01) |
| ***C07K 14/54*** | (2006.01) |
| ***C07K 14/52*** | (2006.01) |
| ***C07K 14/715*** | (2006.01) |
| ***A61K 9/00*** | (2006.01) |
| ***A61P 35/00*** | (2006.01) |
| ***C07K 14/57*** | (2006.01) |
| ***G01N 33/574*** | (2006.01) |

(52) U.S. Cl.

CPC ............ *C12N 15/85* (2013.01); *A61K 9/0009* (2013.01); *A61K 9/0019* (2013.01); *A61P 35/00* (2018.01); *C07K 14/52* (2013.01); *C07K 14/5434* (2013.01); *C07K 14/5443* (2013.01); *C07K 14/57* (2013.01); *C07K 14/7155* (2013.01); *G01N 33/574* (2013.01); *C07K 2319/00* (2013.01)

(58) Field of Classification Search

CPC ......... C12N 15/85; A61P 35/00; A61K 9/019; C07K 14/52; C07K 14/57

See application file for complete search history.

(56) References Cited

U.S. PATENT DOCUMENTS

| | | | | |
|---|---|---|---|---|
| 5,891,432 | A | 4/1999 | Hoo | |
| 7,245,963 | B2 | 7/2007 | Draghia-Akli et al. | |
| 8,802,643 | B1 | 8/2014 | Heller et al. | |
| 2004/0023332 | A1* | 2/2004 | Sung ...................... | A61K 39/39 435/69.5 |
| 2004/0023389 | A1 | 2/2004 | Scaria et al. | |
| 2005/0052630 | A1 | 3/2005 | Smith et al. | |
| 2008/0033340 | A1 | 2/2008 | Heller et al. | |
| 2010/0158930 | A1 | 6/2010 | Zhu et al. | |
| 2011/0027373 | A1 | 2/2011 | Maples et al. | |
| 2011/0124048 | A1* | 5/2011 | Yun ......................... | A61P 35/00 435/69.52 |
| 2011/0268766 | A1 | 11/2011 | Robert et al. | |
| 2017/0348390 | A1 | 12/2017 | Wong et al. | |
| 2020/0123566 | A1 | 4/2020 | Canton | |

FOREIGN PATENT DOCUMENTS

| | | | |
|---|---|---|---|
| CN | 1147834 | A | 4/1997 |
| DE | 102005055128 | A1 | 5/2007 |
| EP | 2 724 727 | A1 | 4/2014 |
| JP | 2004-500047 | A | 1/2004 |
| JP | 2007-501283 | A | 1/2007 |
| JP | 2009-544310 | A | 12/2009 |
| JP | 2010-531878 | A | 9/2010 |
| WO | WO 95/24485 | A2 | 9/1995 |
| WO | WO 97/41241 | A2 | 11/1997 |
| WO | WO 2000/075292 | A1 | 12/2000 |
| WO | WO 01/29233 | A2 | 4/2001 |
| WO | WO 2004/035799 | A2 | 4/2004 |

(Continued)

OTHER PUBLICATIONS

Lima et al., "A DNA vaccine encoding genetic fusions of carcinoembryonic antigen (CEA) and granulocyte/macrophage colony-stimulating factor (GM-CSF)", 2005, Vaccine 23, p. 1273-1283.*

Zhang et al., "Optimizing DC Vaccination by Combination With Oncolytic Adenovirus Coexpressing IL-12 and GM-CSF", published online: Apr. 5, 2011, Molecular Therapy 19(8), p. 1558-1568.*

Chudley et al., "DNA fusion-gene vaccination in patients with prostate cancer induces high-frequency CD8(+) T-cell responses and increases PSA doubling time," Cancer Immunol Immunother, 61(11):2161-2170, (2012).

(Continued)

*Primary Examiner* — Arthur S Leonard

(74) *Attorney, Agent, or Firm* — Procopio, Cory Hargreaves & Savitch LLP

(57) ABSTRACT

Provided are plasmid vector constructs encoding multiple immunomodulatory proteins where each protein or component thereof can be expressed utilizing appropriate promotors and/or translation modifiers. Additional immunomodulatory proteins and genetic adjuvants containing shared tumor antigens can be added to further therapeutic potential as well as allow tracking of therapeutic treatment. Also provides are methods of expressing the plasmid constructs.

14 Claims, 7 Drawing Sheets

Specification includes a Sequence Listing.

(56) References Cited

FOREIGN PATENT DOCUMENTS

| | | | | |
|---|---|---|---|---|
| WO | WO 2004/110371 A2 | 12/2004 | | |
| WO | WO 2008/140173 A1 | 11/2008 | | |
| WO | WO 2009/002562 A2 | 12/2008 | | |
| WO | WO 2010/042189 A2 | 4/2010 | | |
| WO | WO-2010042189 A2 * | 4/2010 | ............. | C12N 15/86 |
| WO | WO 2013/176772 A1 | 11/2013 | | |
| WO | WO 2015/164818 | 10/2015 | | |
| WO | WO 2016/161201 A2 | 10/2016 | | |
| WO | WO 2018/229696 A1 | 12/2018 | | |

OTHER PUBLICATIONS

Connolly et al., "Non-contact helium-based plasma for delivery of DNA vaccines. Enhancement of humoral and cellular immune responses," Hum Vaccin Immunother, 8(11):1729-1733, (2012).

Currier et al., "Widespread intratumoral virus distribution with fractionated injection enables local control of large human rhabdomyosarcoma xenografts by oncolytic herpes simplex viruses," Cancer Gene Ther., 12(4):407-416, (2005).

Garcia et al., "Non-thermal irreversible electroporation for deep intracranial disorders," Conf Proc IEEE Eng Med Biol Soc, 2010:2743-2746, (2010).

GenBank: Accession No. LT727462.1, "Vector pUCT7POL, complete sequence," Feb. 6, 2017. [Retrieved from the Internet Mar. 9, 2020: <URL: https://www.ncbi.nlm.nih.gov/nuccore/LT727462.1?report=genbank>].

Graddis et al., "Structure-function analysis of FLT3 ligand-FLT3 receptor interactions using a rapid functional screen," J Biol Chem, 273(28):17626-17633, (1998).

Menne et al., "A comparison of signal sequence prediction methods using a test set of signal peptides," Bioinformatics, 16(8):741-742, (2000).

Von Heijne, G., "A new method for predicting signal sequence cleavage sites," Nucleic Acids Res., 14(11):4683-4690, (1986).

Von Heijne, G., "Patterns of amino acids near signal-sequence cleavage sites," Eur J Biochem, 133(1):17-21, (1983).

Wren et al., "SIGNAL—Sequence Information and GeNomic AnaLysis," Computer Methods and Programs in Biomedicine, 68(2):177-181, (2002).

WIPO Application No. PCT/IB2018/054344, PCT International Search Report and Written Opinion of the International Searching Authority dated Nov. 13, 2018.

Almeida et al., "CTdatabase: a knowledge-base of high-throughput and curated data on cancer-testis antigens," Nucleic Acids Res., 37(Database Issue):D816-819, (2009). [Retrieved from the Internet May 23, 2019: <URL: https://www.ncbi.nlm.nih.gov/pmc/articles/PMC2686577/pdf/gkn673.pdf>].

Bakker et al., "Melanocyte lineage-specific antigen gp100 is recognized by melanoma-derived tumor-infiltrating lymphocytes," J. Exp. Med., 179(3):1005-1009, (1994). [Retrieved from the Internet May 23, 2019: <URL: http://jem.rupress.org/content/jem/179/3/1005.full.pdf>].

Beckhove et al., "Rapid T cell-based identification of human tumor tissue antigens by automated two-dimensional protein fractionation," J. Clin. Invest., 120(6):2230-2242, (2010). [Retrieved from the Internet May 23, 2019: <URL: https://www.ncbi.nlm.nih.gov/pmc/articles/PMC2877924/pdf/JCI37646.pdf>].

Brandt et al., "The B7 family member B7-H6 is a tumor cell ligand for the activating natural killer cell receptor NKp30 in humans," J. Exp. Med., 206(7):1495-1503, (2009). [Retrieved from the Internet May 23, 2019: <URL: http://jem.rupress.org/content/jem/206/7/1495.full.pdf>].

Burger et al., "Plasmids encoding granulocyte-macrophage colony-stimulating factor and CD154 enhance the immune response to genetic vaccines," Vaccine, 19(15-16):2181-2189, (2001).

Chambers et al., "High-level generation of polyclonal antibodies by genetic immunization," Nature Biotechnology, 21(9):1088-1092, (2003).

Cheng et al., "Tumor-specific immunity and antiangiogenesis generated by a DNA vaccine encoding calreticulin linked to a tumor antigen," J. Clin. Invest., 108(5):669-678, (2001). [Retrieved from the Internet May 23, 2019: <URL: https://www.ncbi.nlm.nih.gov/pmc/articles/PMC209378/pdf/JCI0112346.pdf>].

Chow et al., "Cell-mediated immune responses to the hemagglutinin and neuraminidase antigens of influenza A virus after immunization in humans," Infect. Immun., 25(1):103-109, (1979). [Retrieved from the Internet May 23, 2019: <URL: https://iai.asm.org/content/iai/25/1/103.full.pdf>].

GenBank: : Accession No. ADV31546.2, "tumor necrosis factor-alpha [*Homo sapiens*]," May 3, 2011. [Retrieved from the Internet Jun. 3, 2019: <URL: https://www.ncbi.nlm.nih.gov/protein/ADV31546>].

Gnjatic et al., "NY-ESO-1: review of an immunogenic tumor antigen," Adv. Cancer Res., 95:1-30, (2006).

Hayashi et al., "The innate immune response to bacterial flageliin is mediated by Toll-like receptor 5," Nature, 410(6832):1099-1103, (2001).

Hung et al., "Enhancement of DNA vaccine potency by linkage of antigen gene to a gene encoding the extracellular domain of Fms-like tyrosine kinase 3-ligand," Cancer Res., 61(3):1080-1088, (2001). [Retrieved from the Internet May 23, 2019: <URL: http://cancerres.aacrjournals.org/content/61/3/1080.full-text.pdf>].

Ibrahimi et al., "Highly efficient muiticistronic Ientivirai vectors with peptide 2A sequences," Hum. Gene. Ther., 20(8):845-860, (2009). [Retrieved from the Internet May 30, 2019: <URL: https://www.liebertpub.com>].

Kim et al., "High cleavage efficiency of a 2A peptide derived from porcine teschovirus-1 in human cell lines, zebrafish and mice," PLoS One, 6(4):e18556, (2011). [Retrieved from the Internet May 23, 2019: <URL: https://journals.plos.org/plosone/article?id=10.1371/journal.pone.0018556>].

Kreiter et al., "FLT3 ligand enhances the cancer therapeutic potency of naked RNA vaccines," Cancer Res., 71(19):6132-6142, (2011). [Retrieved from the Internet May 23, 2019: <URL: http://cancerres.aacrjournals.org/content/71/19/6132.full-text.pdf>].

Lee et al., "Inhibition of Established Subcutaneous and Metastatic Murine Tumors by Intramuscular Electroporation of the Interleukin-12 Gene," J Biomed Sci, 10(1):73-86, (2003).

Li et al., "MART-1-specific melanoma tumor-infiltrating lymphocytes maintaining CD28 expression have improved survival and expansion capability following antigenic restimulation in vitro," J. Immunol., 184(1):452-465, (2010). [Retrieved from the Internet May 23, 2019: <URL: http://www.jimmunol.org/content/jimmunol/184/1/452.full.pdf>].

Lima et al., "A DNA vaccine encoding genetic fusions of carcinoembryonic antigen (CEA) and granulocyte/macrophage colony-stimulating factor (GM-CSF)," Vaccine, 23(10):1273-1283, (2005).

Lin et al., "DNA vaccines encoding IL-2 linked to HPV-16 E7 antigen generate enhanced E7-specific CTL responses and antitumor activity," Immunol. Lett., 114(2):86-93, (2007). [Retrieved from the Internet May 23, 2019: <URL: https://www.ncbi.nlm.nih.gov/pmc/articles/PMC2169502/pdf/nihms36013.pdf>].

Lladser et al., "Naked DNA immunization as an approach to target the generic tumor antigen survivin induces humoral and cellular immune responses in mice," Immunobiology, 211(1-2):11-27, (2006).

Maraskovsky et al., "In vivo generation of human dendritic cell subsets by Flt3 ligand," Blood, 96(3):878-884, (2000). [Retrieved from the Internet May 23, 2019: <URL: http://www.bloodjournal.org/content/bloodjournal/96/3/878.full.pdf>].

Marchi et al., "Gene therapy with interleukin-10 receptor and interleukin-12 induces a protective interferon-γ-dependent response against B16F10-Nex2 melanoma," Cancer Gene Ther., 18(2):110-122, (2011). [Retrieved from the Internet May 23, 2019: <URL: https://www.nature.com/articles/cgt201058.pdf>].

NCBI Reference Sequence No. NM_000586.3, "*Homo sapiens* interleukin 2 (IL2), mRNA," May 14, 2019. [Retrieved from the Internet Jun. 3, 2019: <URL: https://www.ncbi.nlm.nih.gov/nuccore/NM_000586.3>].

NCBI Reference Sequence No. NM_000589.3, "*Homo sapiens* interleukin 4 (IL4), transcript variant 1, mRNA," Nov. 18, 2018.

(56) References Cited

OTHER PUBLICATIONS

[Retrieved from the Internet Jun. 3, 2019: <URL: https://www.ncbi.nlm.nih.gov/nuccore/NM_000589.3>].
NCBI Reference Sequence No. NM_000590.1, "*Homo sapiens* interleukin 9 (IL9), mRNA," May 4, 2019. [Retrieved from the Internet Jun. 3, 2019: <URL: https://www.ncbi.nlm.nih.gov/nuccore/NM_000590.1>].
NCBI Reference Sequence No. NM_000758.3, "*Homo sapiens* colony stimulating factor 2 (CSF2), mRNA," Oct. 13, 2018. [Retrieved from the Internet May 24, 2019: <URL: https://www.ncbi.nlm.nih.gov/nuccore/NM_000758.3>].
NCBI Reference Sequence No. NM_001199886.1, "*Homo sapiens* interleukin 7 (IL7), transcript variant 2, mRNA," May 14, 2019. [Retrieved from the Internet Jun. 3, 2019: <URL: https://www.ncbi.nlm.nih.gov/nuccore/NM_001199886.1>].
NCBI Reference Sequence No. NM_001288705.2, "*Homo sapiens* colony stimulating factor 1 receptor (CSF1R), transcript variant 2, mRNA," May 21, 2019. [Retrieved from the Internet May 24, 2019: <URL: https://www.ncbi.nlm.nih.gov/nuccore/NM_001288705.2>].
NCBI Reference Sequence No. NM_002176.3, "*Homo sapiens* interferon beta 1 (IFNB1), mRNA," Sep. 24, 2018. [Retrieved from the Internet Jun. 3, 2019: <URL: https://www.ncbi.nlm.nih.gov/nuccore/NM_002176.3>].
NCBI Reference Sequence No. NM_002187.2, "*Homo sapiens* interleukin 12B (IL12B), mRNA," May 4, 2019. [Retrieved from the Internet Jun. 3, 2019: <URL: https://www.ncbi.nlm.nih.gov/nuccore/NM_002187.2>].
NCBI Reference Sequence No. NM_004343.2, "*Homo sapiens* calreticulin (CALR), mRNA," Oct. 12, 2008. [Retrieved from the Internet May 24, 2019: <URL: https://www.ncbi.nlm.nih.gov/nuccore/NM_004343.2>].
NCBI Reference Sequence No. NM 005755.2, "*Homo sapiens* Epstein-Barr virus induced 3 (EBI3), mRNA," Oct. 21, 2018. [Retrieved from the Internet Jun. 3, 2019: <URL: https://www.ncbi.nlm.nih.gov/nuccore/NM_005755.2>].
NCBI Reference Sequence No. NM_006900.3, "*Homo sapiens* interferon alpha 13 (IFNA13), mRNA," May 4, 2019. [Retrieved from the Internet Jun. 3, 2019: <URL: https://www.ncbi.nlm.nih.gov/nuccore/NM_006900.3>].
NCBI Reference Sequence No. NM_021803.3, "*Homo sapiens* interleukin 21 (IL21), transcript variant 1, mRNA," Jun. 17, 2018. [Retrieved from the Internet Jun. 3, 2019: <URL: https://www.ncbi.nlm.nih.gov/nuccore/NM_021803.3>].
NCBI Reference Sequence No. NM_024013.2, "*Homo sapiens* interferon alpha 1 (IFNA1), mRNA," May 4, 2019. [Retrieved from the Internet Jun. 3, 2019: <URL: https://www.ncbi.nlm.nih.gov/nuccore/NM_024013.2>].
NCBI Reference Sequence No. NM_145659.3, "*Homo sapiens* interleukin 27 (IL27), mRNA," May 21, 2019. [Retrieved from the Internet Jun. 3, 2019: <URL: https://www.ncbi.nlm.nih.gov/nuccore/NM_145659.3>].
NCBI Reference Sequence No. NP_000577.2, "interleukin-2 precursor [*Homo sapiens*]," May 14, 2019. [Retrieved from the Internet Jun. 3, 2019: <URL: https://www.ncbi.nlm.nih.gov/protein/NP_000577.2>].
NCBI Reference Sequence No. NP_000580.1, "interleukin-4 isoform 1 precursor [*Homo sapiens*]," May 28, 2019. [Retrieved from the Internet Jun. 3, 2019: <URL: https://www.ncbi.nlm.nih.gov/protein/NP_000580.1>].
NCBI Reference Sequence No. NP_000581.1, "interleukin-9 precursor [*Homo sapiens*]," May 17, 2019. [Retrieved from the Internet Jun. 3, 2019: <URL: https://www.ncbi.nlm.nih.gov/protein/NP_000581.1x>].
NCBI Reference Sequence No. NP_000610.2 , "interferon gamma precursor [*Homo sapiens*]," May 14, 2019. [Retrieved from the Internet Jun. 3, 2019: <URL: https://www.ncbi.nlm.nih.gov/protein/NP_000610.2>].
NCBI Reference Sequence No. NP_000873.2, "interleukin-12 subunit alpha isoform 1 precursor [*Homo sapiens*]," May 21, 2019. [Retrieved from the Internet Jun. 3, 2019: <URL: https://www.ncbi.nlm.nih.gov/protein/NP_000873.2>].
NCBI Reference Sequence No. NP_001003292.1, "interleukin-12 subunit beta precursor [Canis lupus familiaris]," Feb. 16, 2019. [Retrieved from the Internet Jun. 3, 2019: <URL: https://www.ncbi.nlm.nih.gov/protein/NP_001003292.1>].
NCBI Reference Sequence No. NP_001152896.1, "interleukin-12 subunit alpha isoform 1 [Mus musculus]," May 19, 2019. [Retrieved from the Internet Jun. 3, 2019: <URL: https://www.ncbi.nlm.nih.gov/protein/NP_001152896.1>].
NCBI Reference Sequence No. NP_001186815.1, "interleukin-7 isoform 2 precursor [*Homo sapiens*]," May 14, 2019. [Retrieved from the Internet Jun. 3, 2019: <URL: https://www.ncbi.nlm.nih.gov/protein/NP_001186815.1>].
NCBI Reference Sequence No. NP_001290173.1, "interleukin-12 subunit beta precursor [Mus musculus]," May 14, 2019. [Retrieved from the Internet Jun. 3, 2019: <URL: https://www.ncbi.nlm.nih.gov/protein/NP_001290173.1>].
NCBI Reference Sequence No. NP_002167.1, "interferon beta precursor [*Homo sapiens*]," May 28, 2019. [Retrieved from the Internet Jun. 3, 2019: <URL: https://www.ncbi.nlm.nih.gov/protein/NP_002167.1>].
NCBI Reference Sequence No. NP_002178.2, "interleukin-12 subunit beta precursor [*Homo sapiens*]," May 4, 2019. [Retrieved from the Internet Jun. 3, 2019: <URL: https://www.ncbi.nlm.nih.gov/protein/NP_002178.2>].
NCBI Reference Sequence No. NP_005746.2, "interleukin-27 subunit beta precursor [*Homo sapiens*]," Jun. 2, 2019. [Retrieved from the Internet Jun. 3, 2019: <URL: https://www.ncbi.nlm.nih.gov/protein/NP_005746.2>].
NCBI Reference Sequence No. NP_008831.3, "interferon alpha-1/13 precursor [*Homo sapiens*]," May 4, 2019. [Retrieved from the Internet Jun. 3, 2019: <URL: https://www.ncbi.nlm.nih.gov/protein/NP_008831.3>].
NCBI Reference Sequence No. NP_068575.1, "interleukin-21 isoform 1 precursor [*Homo sapiens*]," Jun. 2, 2019. [Retrieved from the Internet Jun. 3, 2019: <URL: https://www.ncbi.nlm.nih.gov/protein/NP_068575.1>].
NCBI Reference Sequence No. NP_076918.1, "interferon alpha-1/13 precursor [*Homo sapiens*]," May 17, 2019. [Retrieved from the Internet Jun. 3, 2019: <URL: https://www.ncbi.nlm.nih.gov/protein/NP_076918.1>].
NCBI Reference Sequence No. NP_663634.2, "interleukin-27 subunit alpha precursor [*Homo sapiens*]," May 21, 2019. [Retrieved from the Internet Jun. 3, 2019: <URL: https://www.ncbi.nlm.nih.gov/protein/NP_663634.2>].
NCBI Reference Sequence No. XM_01 1537494.1, "Predicted: *Homo sapiens* lysosomal associated membrane protein 1 (LAMP1), transcript variant X1, mRNA," Jun. 6, 2016. [Retrieved from the Internet May 23, 2019: <URL: https://www.ncbi.nlm.nih.gov/nuccore/XM_011537494.1].
NCBI Reference Sequence No. XM_011538477.2, "Predicted: *Homo sapiens* interleukin 23 subunit alpha (IL23A), transcript variant X1, mRNA," Mar. 26, 2018. [Retrieved from the Internet Jun. 3, 2019: <URL: https://www.ncbi.nlm.nih.gov/nuccore/XM_011538477.2>].
NCBI Reference Sequence No. XM_017026533.1, "Predicted: *Homo sapiens* fms related tyrosine kinase 3 ligand (FLT3LG), transcript variant X11, mRNA," Mar. 26, 2018. [Retrieved from the Internet May 23, 2019: <URL: https://www.ncbi.nlm.nih.gov/nuccore/XM_017026533>].
NCBI Reference Sequence No. XP_011536779.1, "interleukin-23 subunit alpha isoform X1 [*Homo sapiens*]," Mar. 26, 2018. [Retrieved from the Internet Jun. 3, 2019: <URL: https://www.ncbi.nlm.nih.gov/protein/XP_011536779.1>].
NCBI Reference Sequence No. XP_013965819.1, "interleukin-12 subunit alpha isoform X1 [Canis lupus familiaris]," Sep. 5, 2017. [Retrieved from the Internet Jun. 3, 2019: <URL: https://www.ncbi.nlm.nih.gov/protein/XP_013965819.1>].
Peng et al., "Characterization of human papillomavirus type 11-specific immune responses in a preclinical model," Laryngoscope,

(56) References Cited

OTHER PUBLICATIONS

120(3):504-510, (2010). [Retrieved from the Internet May 23, 2019: <URL: https://www.ncbi.nlm.nih.gov/pmc/articles/PMC2908018/pdf/nihms-220705.pdf>].
Rivoltini et al., "Human Tumor-Derived Heat Shock Protein 96 Mediates In Vitro Activation and In Vivo Expansion of Melanoma- and Colon Carcinoma-Specific T Cells," J Immunol, 171(7):3467-3474, (2003). [Retrieved from the Internet Apr. 9, 2019: <URL: http://www.jimmunol.org/content/171/7/3467>].
Rivoltini et al., "Human tumor-derived heat shock protein 96 mediates in vitro activation and in vivo expansion of melanoma- and colon carcinoma-specific T cells," J. Immunol., 171(7):3467-3474, (2003). [Retrieved from the Internet May 23, 2019: <URL: http://www.jimmunol.org/content/jimmunol/171/7/3467.full.pdf>].
Schmidt et al., "Survivin is a shared tumor-associated antigen expressed in a broad variety of malignancies and recognized by specific cytotoxic T cells," Blood, 102(2):571-576, (2003). [Retrieved from the Internet May 23, 2019: <URL: http://www.bloodjournal.org/content/bloodjournal/102/2/571.full.pdf>].
Seo et al., "Optimal induction of HPV DNA vaccine-induced CD8+ T cell responses and therapeutic antitumor effect by antigen engineering and electroporation," Vaccine, 27(42):5906-5912, (2009).
Shi et al., "Genome-wide analysis of molecular changes in IL-12-induced control of mammary carcinoma via IFN-gamma-independent mechanisms," J. Immunol., 172(7):4111-4122, (2004). [Retrieved from the Internet May 23, 2019: <URL: http://www.jimmunol.org/content/jimmunol/172/7/4111.full.pdf>].
Skipper et al., "An HLA-A2-restricted tyrosinase antigen on melanoma cells results from posttranslational modification and suggests a novel pathway for processing of membrane proteins," J. Exp. Med., 183(2):527-534, (1996). [Retrieved from the Internet May 23, 2019: <URL: http://jem.rupress.org/content/jem/183/2/527.full.pdf>].
Szymczak et al., "Correction of multi-gene deficiency in vivo using a single 'self-cleaving' 2A peptide-based retroviral vector," Nat. Biotechnol., 22(5):589-594, (2004).
Tenbusch et al., "Coexpression of GM-CSF and antigen in DNA prime-adenoviral vector boost immunization enhances polyfunctional CD8+ T cell responses, whereas expression of GM-CSF antigen fusion protein induces autoimmunity," BCM Immunology, 9(13):1-15, (2008).
Vergati et al., "Strategies for Cancer Vaccine Development," Journal of Biomedicine and Biotechnology, 2010:Article ID 596432, 13 pages, (2010).
Vom Berg et al., "Intratumorai IL-12 combined with CTLA-4 blockade elicits T cell-mediated glioma rejection," J. Exp. Med., 210(13):2803-2811, (2013). [Retrieved from the Internet May 23, 2019: <URL: http://jem.rupress.org/content/jem/210/13/2803.full.pdf>].
Vonderheide, RH, "Telomerase as a universal tumor-associated antigen for cancer immunotherapy," Oncogene, 21(4):674-679, (2002). [Retrieved from the Internet May 23, 2019: <URL: https://www.nature.com/articles/1205074.pdf>].
Wen et al., "Tricistronic viral vectors co-expressing interleukin-12 (1L-12) and CD80 (B7-1) for the immunotherapy of cancer: Preclinical studies in myeloma," Cancer Gene Therapy, 8(5):361-370, (2001).
Wieking et al., "A non-oncogenic HPV 16 E6/E7 vaccine enhances treatment of HPV expressing tumors," Cancer Gene Ther., 19(10):667-674, (2012). [Retrieved from the Internet May 23, 2019: <URL: https://www.nature.com/articles/cgt201255>].
Yo et al., "Coexpression of Flt3 ligand and GM-CSF genes modulates immune responses induced by HER2/neu DNA vaccine," Cancer Gene Therapy, 14(11):904-917, (2007).
Zeng et al., "Development of a DNA vaccine targeting Merkel cell polyomavirus," Vaccine, 30(7):1322-1329, (2012).
Zhu et al., "Novel human interleukin-15 agonists," J. Immunol., 183(6):3598-3607, (2009). [Retrieved from the Internet May 23, 2019: <URL: http://www.jimmunol.org/content/jimmunol/183/6/3598.full.pdf>].
European Application No. 16876875.2, Supplementary Partial European Search Report and Provisional Opinion dated Apr. 25, 2019, 19 pages.
"PCI-neo Mammalian Expression Vector: Instructions for Use of Product E1841," Promega Corporation, 5 pages, (2009).
Chaplin et al., "Production of Interleukin-12 as a Self-Processing 2A Polypeptide," Journal of Inteferon and Cytokine Research, 19:235-241, (1999).
Dubois et al., "Preassociation of IL-15 with IL-15Rα-IgG1-Fc Enhances its Activity on Proliferation of NK and CD8+ /CD44high T Cells and its Antitumor Action," The Journal of Immunology, 180:2099-2106, (2008).
Japan Application No. 2018-532285, Office Action dated Nov. 4, 2020.
Dean, D.A., et al., "Electrical Impedance Spectroscopy Study of Biological Tissues," Journal of Electrostatics, vol. 66(3-4): 165-177 (Mar. 2008).
PCT International Search Report and Written Opinion of the International Searching Authority for application PCT/US2016/673388 dated May 5, 2017.
PCT International Preliminary Report on Patentability for application PCT/US2016/673388 dated Jun. 28, 2018.
Hajizadeh-Sikaroodi et al., "Lentiviral Mediating Genetic Engineered Mesenchymal Stem Cells for Releasing IL-27 as a Gene Therapy Approach for Autoimmune Diseases," Cell Journal, 16(3):255-262, (Autumn 2014) (epub. Oct. 4, 2014).
Daud et al., "Intratumoral electroporation of plasmid interleukin-12: efficacy and biomarker analyses from a phase 2 study in melanoma (OMS-I100)," Journal of Translational Medicine, 13(Suppl 1):O11, (Jan. 2015).
Almo et al., "Considerations for Combined Immume Checkpoint Modulation and Radiation Treatment," Radiation Research, 182(2):230-238, (Aug. 2014).
Gao et al., "Tumoral expression of IL-33 inhibits tumor growth and modifies the tumor microenvironment through CD8+ T and NK cells," J. Immunol., 194(1):438-445, (Jan. 2015). [Retrieved from the Internet May 23, 2019: <URL: http://www.jimmunol.org/content/jimmunol/194/1/438.full.pdf>].
Grubor-Bauk et al., "Intradermal delivery of DNA encoding HCV NS3 and perforin elicits robust cell-mediated immunity in mice and pigs," Gene Ther., 23(1):26-37, (Jan. 2016) (epub. Oct. 2015).
Hu-Lieskovan et al., "Combining Target Therapy with Immunotherapy in BRAF-Mutant Melanoma: Promise and Challenges," J. Clin. Oncol., 32(21):2248-2254, (Jul. 20, 2014).
Kim et al., "Clearance of persistent HPV infection and cervical lesion by therapeutic DNA vaccine in CIN3 patients," Nat. Commun., 5:5317, 14 pages, (Oct. 30, 2014). [Retrieved from the Internet May 23, 2019: <URL: https://www.ncbi.nlm.nih.gov/pmc/articles/PMC4220493/pdf/ncomms6317.pdf>].
Lyngaa et al., "T-cell responses to oncogenic merkel cell polyomavirus proteins distinguish patients with merkel cell carcinoma from healthy donors," Clin. Cancer Res., 20(7):1768-1778, (Apr. 2014) (epub. Feb. 13, 2014).
Peng et al., "Identification of the murine H-2D(b) and human HLA-A*0201 MHC class I-restricted HPV6 E7-specific cytotoxic T lymphocyte epitopes," Cancer Immunol. Immunother., 65(3):261-271, (Mar. 2016). [Retrieved from the Internet May 23, 2019: <URL: https://www.ncbi.nlm.nih.gov/pmc/articles/PMC5690558/pdf/nihms751652.pdf>].
Quetglas et al., "Virotherapy with a Semliki Forest Virus-Based Vector Encoding IL12 Synergizes with PD-1/PD-L1 Blockade," Cancer Immunol. Res., 3(5):449-454, (May 2015) (epub. Feb. 17, 2015).
Rapoport et al., "NY-ESO-1-specific TCR-engineered T cells mediate sustained antigen-specific antitumor effects in myeloma," Nat. Med., 21(8):914-921, (Aug. 2015). [Retrieved from the Internet May 23, 2019: <URL: https://www.ncbi.nlm.nih.gov/pmc/articles/PMC4529359/pdf/nihms-702896.pdf>].
Sabado et al., "Resiquimod as an immunologic adjuvant for NY-ESO-1 protein vaccination in patients with high-risk melanoma," Cancer Immuno. Res., 3(3):278-287, (Mar. 2015) (epub. Jan. 29, 2015).

(56) References Cited

OTHER PUBLICATIONS

Vanneman et al., "Combining Immunotherapy and Targeted Therapies in Cancer Treatment," Nat. Rev. Cancer, 12(4):237-251, (Mar. 2012).
Zhang et al., "IL-12 augments antitumor responses to cycled chemotherapy," J. Immunother., 38(4):137-144, (May 2015).
Connolly et al., "Optimization of a plasma facilitated DNA delivery method," Bioelectrochemistry, 103:15-21, (Jun. 2015).
Chen et al., "A Review of Novel Intralesional Therapies for Melanoma, With an Emphasis on a Potential Combination Approach," Oncology, 30(5):442-443, (May 2016). [Retrieved from the Internet Mar. 9, 2020: <URL: https://www.cancernetwork.com/oncology-journal/review-novel-intralesional-therapies-melanoma-emphasis-potential-combination-approach>].
Burkart, et al., "Improving therapeutic efficacy of IL-12 intratumoral gene electrotransfer through novel plasmid design and modified parameters," Gene Therapy 25:93-103, (2018).
Esfandiary, et al., "New York esophageal squamous cell carcinoma-1 and cancer immunotherapy," Immunotherapy, 7(4), 411-439, (2015).
Lee, et al., "Activated B cells modified by electroporation of muitipie mRNAs encoding immune stimulatory molecules are comparable to mature dendritic cells in inducing in vitro antigen-specific T-cell responses," Immunology, 125, 229-240, (2008).
Lorenzo, et al., "Efficient expression of bioactive murine IL12 as a self-processing P2A Poly peptide driven by inflammation-regulated promoters in tumor cell lines," Cancer Gene Therapy, 22, 542-551,(2015).
Mukhopadhyay, et al., "Characterization of abscopal effects of intratumoral electroporation-mediated IL-12 gene therapy," Gene Therapy, 26:1-15, (2019).
Shore, et al., "A clinical trial for the safety and imunogenicity of a DNA-based Immunotherapy in men with biochemically (PSA) relapsed prostate cancer," Journal of Clinical Oncology, vol. 35, No. 15 suppl, pages e14634-e14634, (May 20, 2017).
European Application No. 18817400.7 Extened European Search Report dated Feb. 24, 2021.
Wang et al., "Target Gene Transfer Mediated by Electroporation for Cancer Therapy in vivo", DNA, Prog Biomchem Biopys, 29(5):734-740, (2002).
Chinese Application No. 201680081690.5, Office Action dated Jan. 4, 2022.
Cheever et al., "The Prioritization of Cancer Antigens: A National Cancer Institute Pilot Project for the Acceleration of Translational Research," Clin. Cancer Res., 15(17):5323-5337 (2009).
WIPO Application No. PCT/US2019/065639, PCT International Preliminary Report on Patentability dated Jun. 8, 2021.
WIPO Application No. PCT/US2019/065639, PCT International Search Report dated Apr. 10, 2020.

* cited by examiner

| | rhIL15 | IL15-2A-Ra | IL15-2A-Ra-Fc |
|---|---|---|---|
| EC50 | 5.829 | 11.96 | 11.82 |

PLASMID CONSTRUCTS FOR HETEROLOGOUS PROTEIN EXPRESSION AND METHODS OF USE

The Sequence Listing filed electronically herewith is also hereby incorporated by reference in its entirety (File Name: OM1507WO01-SEQLIST.txt; Date Created: Dec. 16, 2016; File Size: 41 KB.).

FIELD OF THE INVENTION

The present invention relates to recombinant expression vectors for intratumoral delivery of at least two genes encoding each chain of a therapeutically active multimeric polypeptide. Each nucleic acid chain encoding the multimer is separated by at least one translation modulating element. Additional genes encoding therapeutic polypeptides and tracking antigens can be added using additional translation modifiers to the nucleic acid chain or as a separate gene in the expression vector.

BACKGROUND OF THE INVENTION

*E. coli* plasmids have long been an important source of recombinant DNA molecules used by researchers and by industry. Today, plasmid DNA is becoming increasingly important as the next generation of biotechnology products (e.g., gene medicines and DNA vaccines) make their way into clinical trials, and eventually into the pharmaceutical marketplace. Expression plasmid DNA may find application as vehicles to deliver therapeutic proteins to sites on a patient where treatment is needed, e.g., tumors.

This "intratumoral delivery" often involves the delivery of immunomodulators to the tumor microenvironment. Immunotherapy has recently drawn attention as a fourth method following surgery, chemotherapy and radiation therapy for treating tumors. Since immunotherapy utilizes the immunity inherent to humans, it is said that the physical burden on patients are less in immunotherapy than those in other therapies. The therapeutic approaches known as immunotherapies include: cell transfer therapy in which cells such as lymphokine-activated cells, natural killer T-cells or γδT cells obtained, for example, from exogenously-induced cytotoxic T-lymphocytes (CTLs) or peripheral blood lymphocytes by expansion culture using various method are transferred; dendritic cell-transfer therapy or peptide vaccine therapy by which in vivo induction of antigen-specific CTLs is expected; Th1 cell therapy; and immune gene therapy in which genes expected to have various effects are introduced ex vivo into the above-mentioned cells to transfer them in vivo. In these immunotherapies, CD4-positive T cells and CD8-positive T cells have traditionally known to play a critical role.

In vivo electroporation is a gene delivery technique that has been used successfully for efficient delivery of plasmid DNA to many different tissues. Studies have reported the administration of in vivo electroporation for delivery of plasmid DNA to B16 melanomas and other tumor tissues. Systemic and local expression of a gene or cDNA encoded by a plasmid can be obtained with administration of in vivo electroporation. Use of in vivo electroporation enhances plasmid DNA uptake in tumor tissue, resulting in expression within the tumor, and delivers plasmids to muscle tissue, resulting in systemic cytokine expression.

It has been shown that electroporation can be used to transfect cells in vivo with plasmid DNA. Recent studies have shown that electroporation is capable of enhancing delivery of plasmid DNA as an antitumor agent. Electroporation has been administered for treatment of hepatocellular carcinomas, adenocarcinoma, breast tumors, squamous cell carcinoma and B16.F10 melanoma in rodent models. The B16.F10 murine melanoma model has been used extensively for testing potential immunotherapy protocols for the delivery of an immunomodulatory molecule including cytokines either as recombinant protein or by gene therapy.

Various protocols known in the art can be utilized for the delivery of plasmid encoding an immunomodulatory protein utilizing in vivo electroporation for the treatment of cancer. The protocols known in the art describe in vivo electroporation mediated cytokine based gene therapy, both intratumor and intramuscular, utilizing low-voltage and long-pulse currents.

Combination immunotherapies that involve various phases of the cancer-immunity cycle may enhance the ability to prevent immune escape by targeting multiple mechanisms by which tumor cells avoid elimination by the immune system, with synergistic effects that may offer improved efficacy in broader patient populations. Often these combination therapeutic immunomodulatory proteins are complex molecules involving one or more homo- or heterodimeric chains, e.g., IL-12 or IL-15/IL-15Rα, fusion proteins encoding genetic adjuvants and shared tumor antigens. Administration of multiple proteins as therapeutics is complex and costly. Use of intratumoral delivery of multiple encoded proteins using expression plasmids is simpler and more cost effective. However, current expression plasmid constructs do not address the need for adequate production of each immunomolulatory protein. The present invention addresses this need by providing a expression plasmids encoding multiple immunomodulators with appropriately placed promoters and translation modifiers.

SUMMARY OF THE INVENTION

Figure 1:
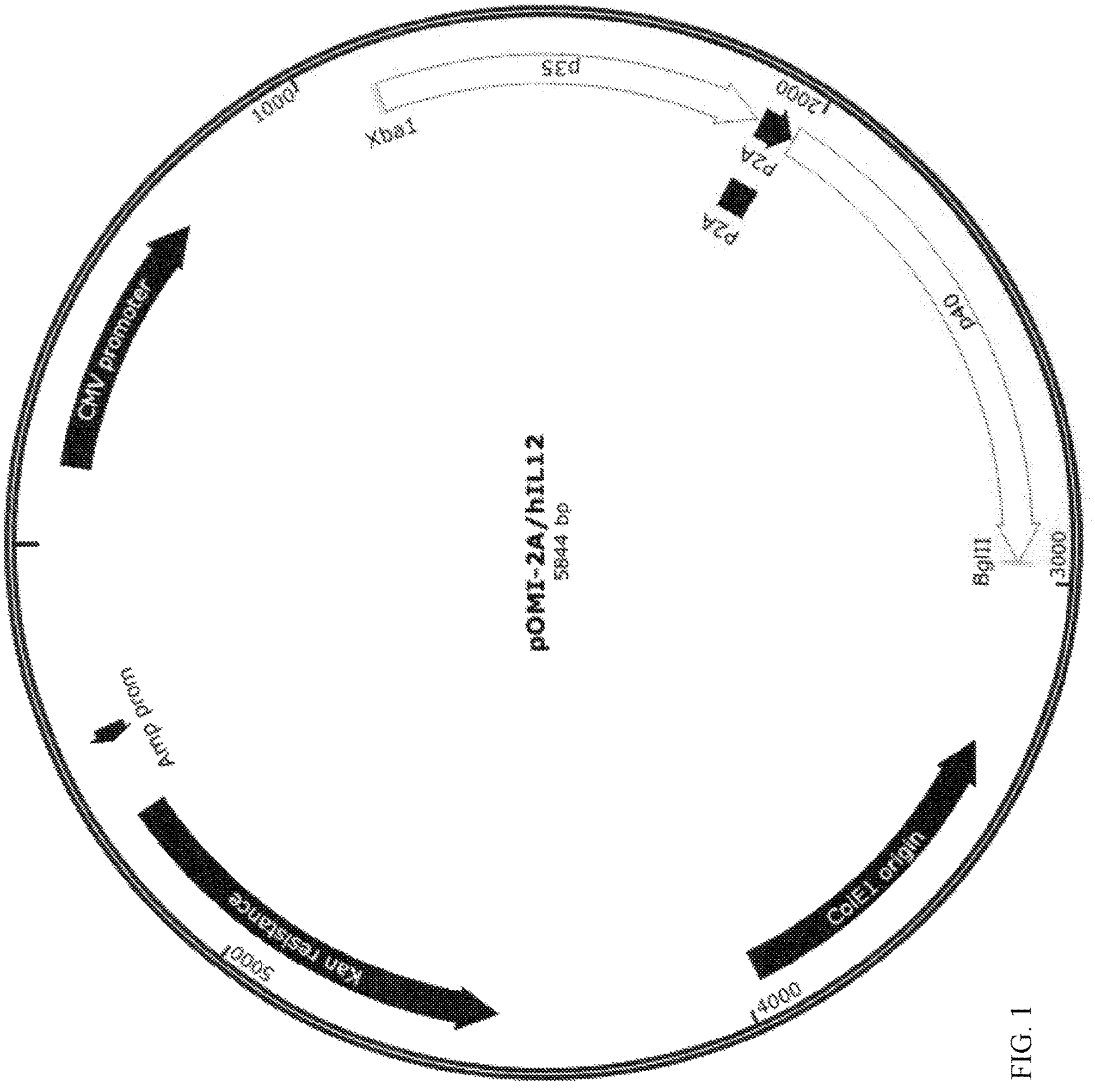
FIG. 1 shows the plasmid map of human IL-12 and P2A in pOMI2A.
Figure 2:
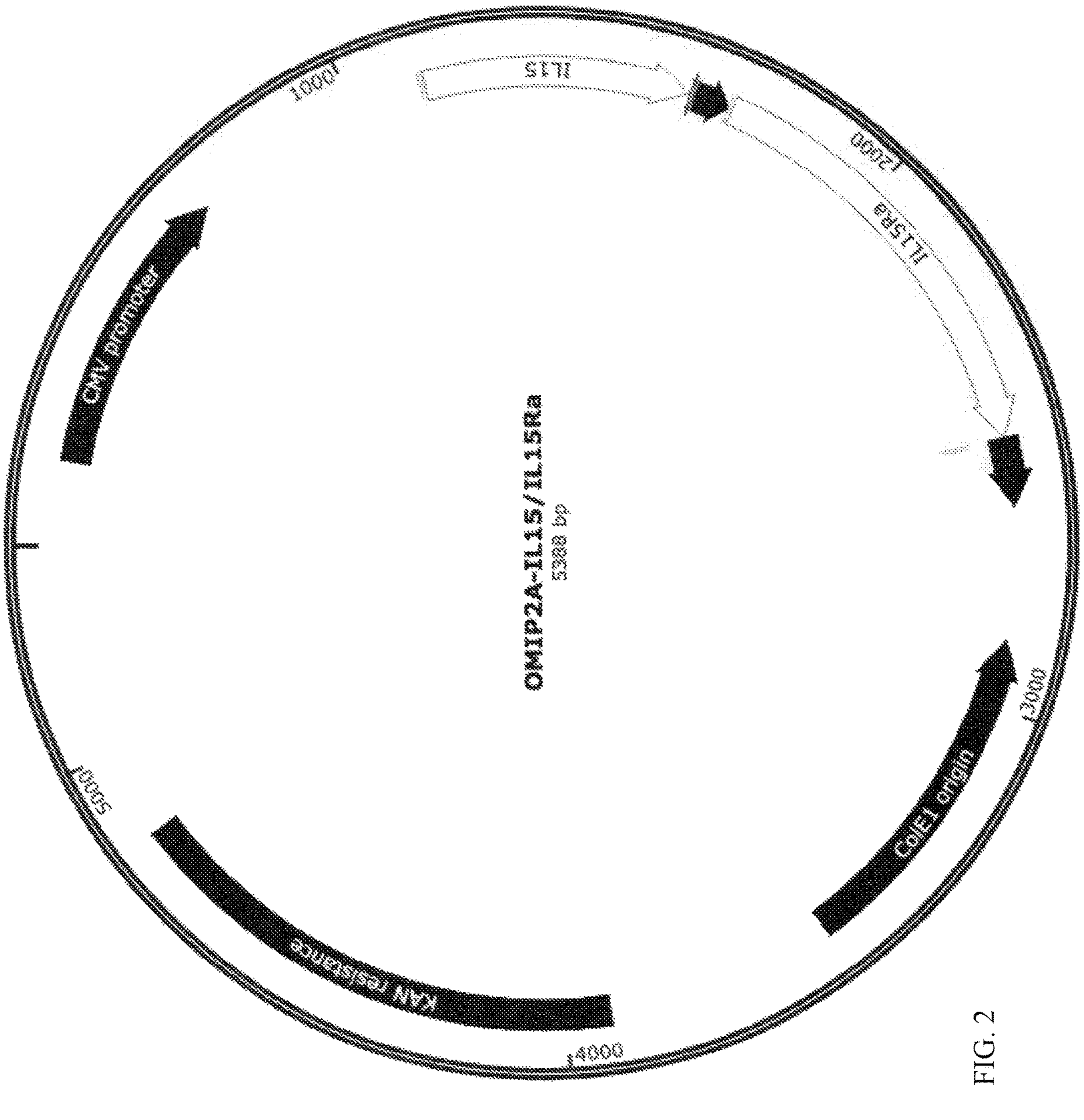
FIG. 2 shows the plasmid map of human IL-15/IL-15Ra and P2A in pOMI2A.

The present invention provides an expression plasmid construct comprising a plurality of expression cassettes defined by the formula: P-A-T-B where: a) P is an expression promotor; b) A and B encode immunomodulatory molecules; and c) T is a translation modification element. In certain embodiments, P is selected from the group consisting of a human CMV promoter, a simian CMV promoter, SV-40, mPGK, and β-Actin, and the immunomodulatory molecules are selected from the group consisting of immunostimulatory cytokines and genetic adjuvants fused to at least one antigen.

The present invention provides an expression plasmid comprising a plurality of expression cassettes defined by the formula: P-A-T-A'-T-B where a) P is an expression promotor; b) A and A' are chains of a heterodimeric cytokine; c) B is at least one genetic adjuvant fused to at least one antigen; and d) T is a translation modification element. In certain embodiments, P is selected from the group consisting of a human CMV promoter, a simian CMV promoter, SV-40, mPGK, and β-Actin, the heterodimeric cytokine is selected from the group consisting of IL-12, IL-15, IL-23, and IL-27; A is selected from the group consisting of IL-12p35, IL-23p19, EB13, IL-15; A' is selected from the group consisting of IL-12p40, IL-27p28, and IL-15Rα; the translation modification element is selected from the group consisting of a P2A family member and IRES; the genetic adjuvant is selected from the group consisting of Flt3 ligand, LAMP-1, Calreticulin, Human heat shock protein 96; GM-CSF, and CSF Receptor 1; antigen is selected from the group consisting of: NYESO-1, OVA, RNEU, MAGE-A1, MAGE-A2, Mage-A10, SSX-2, Melan-A, MART-1, Tyr, Gp100, LAGE-1, Survivin, PRS pan-DR, CEA peptide CAP-1, OVA, HCV-NS3, and an HPV vaccine peptide.

The present invention provides for an expression plasmid comprising a plurality of expression cassettes defined by the formula: P-A-T-B-T-B' where P is an expression promoter; A is at least one genetic adjuvant fused to at least one antigen; B and B' are chains of a heterodimeric cytokine; and T is a translation modification element. In certain embodiments, P is selected from the group consisting of a human CMV promoter, a simian CMV promoter, SV-40, mPGK, and β-Actin, the heterodimeric cytokine is selected from the group consisting of IL-12, IL-15, IL-23, and IL-27; A is selected from the group consisting of IL-12p35, IL-23p19, EBI3, IL-15; A' is selected from the group consisting of IL-12p40, IL-27p28, and IL-15Rα; the translation modification element is selected from the group consisting of a P2A family member and IRES; the genetic adjuvant is selected from the group consisting of Flt3 ligand; LAMP-1; Calreticulin; Human heat shock protein 96; GM-CSF; and CSF Receptor 1; and the antigen is selected from the group consisting of: NYESO-1, OVA, RNEU, MAGE-A1, MAGE-A2, Mage-A10, SSX-2, Melan-A, MART-1, Tyr, Gp100, LAGE-1, Survivin, PRS pan-DR, CEA peptide CAP-1, OVA, HCV-NS3, and an HPV vaccine peptide.

The present invention provides a method of treating a tumor in a subject comprising delivering the expression plasmid of either of the formulas P-A-T-A'-T-B or P-A-T-B'-T-B' into the tumor using at least one intratumoral electroporation pulse. In certain embodiments, the intratumoral electroporation pulse has a field strength of about 200 V/cm to 1500 V/cm; the subject is a human; the tumor is selected from the group of melanoma, triple negative breast cancer, Merkel Cell Carcinoma, CTCL, and head and neck squamous cell carcinoma; and the electroporation pulse is delivered by a generator capable of electrochemical impedance spectroscopy.

The present invention provides an expression plasmid construct comprising a plurality of expression cassettes defined by the formula: P-A-T-A' where a) P is an expression promotor; b) A, and A' encode subunits of an immunomodulatory molecule; and c) T is a translation modification sequence. In certain embodiments, P is selected from group consisting of human CMV promoter, a simian CMV promoter, SV-40, mPGK, and β-Actin, A is selected from the group consisting of IL-12p35, IL-23p19, EBI3, IL-15, A' is selected from the group consisting of IL-12p40, IL-27p28, and IL-15Rα; and T is selected from the group consisting of a P2A and IRES.

DETAILED DESCRIPTION

As used herein, including the appended claims, the singular forms of words such as "a," "an," and "the," include their corresponding plural references unless the context clearly dictates otherwise.

All references cited herein are incorporated by reference to the same extent as if each individual publication, patent application, or patent, was specifically and individually indicated to be incorporated by reference.

I. Definitions

"Activity" of a molecule may describe or refer to the binding of the molecule to a ligand or to a receptor, to catalytic activity, to the ability to stimulate gene expression, to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" may also mean specific activity, e.g., [catalytic activity]/[mg protein], or [immunological activity]/[mg protein], or the like.

"Translation modulating element" or "translation modifier" as used herein, means a specific translation initiator or ribosomal skipping modulator wherein a picornavirus-derived sequence in the nascent polypeptide chain prevents covalent amide linkage with the next amino acid. Incorporation of this sequence results in co-expression of each chain of a heterodimeric protein with equal molar levels of the translated polypeptides. Contemplated are: the 2A family of ribosomal skipping modulators that include, but are not limited to, P2A, T2A, E2A or F2A, all of which share the PG/P cleavage site (See Table 5); and internal ribosomal entry sites (IRES).

In accordance with the present invention there may be employed conventional molecular biology, microbiology, and recombinant DNA techniques within the skill of the art. Such techniques are explained in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook, et al., 1989"); DNA Cloning: A Practical Approach, Volumes I and II (D. N. Glover ed. 1985); Oligonucleotide Synthesis (M. J. Gaited. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel, et al. (eds.), Current Protocols in Molecular Biology, John Wiley & Sons, Inc. (1994).

A "polynucleotide," "nucleic acid" or "nucleic acid molecule" includes DNA or RNA. For example, in an embodiment of the invention, the polynucleotide is the circular plasmid pOMI2A.

A "polynucleotide sequence," "nucleic acid sequence" or "nucleotide sequence" is a series of nucleotides in a nucleic acid, such as DNA or RNA, and means any chain of two or more nucleotides.

A "coding sequence" or a sequence "encoding" an expression product such as a RNA or peptide (e.g., an immunoglobulin chain), is a nucleotide sequence that, when expressed, results in production of the product.

As used herein, the term "oligonucleotide" refers to a nucleic acid, generally of no more than about 300 nucleotides (e.g., 30, 40, 50, 60, 70, 80, 90, 150, 175, 200, 250 or 300), that may be hybridizable to a genomic DNA molecule, a cDNA molecule, or an mRNA molecule encoding a gene, mRNA, cDNA, or other nucleic acid of interest. Oligonucleotides are usually single-stranded, but may be double-stranded. Oligonucleotides can be labeled, e.g., by incorporation of 32P-nucleotides, 3H-nucleotides, 14C-nucleotides, 35S-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids. Generally, oligonucleotides are prepared synthetically, e.g., on a nucleic acid synthesizer.

A "protein sequence," "peptide sequence" or "polypeptide sequence," or "amino acid sequence" refers to a series of two or more amino acids in a protein, peptide or polypeptide.

"Protein," "peptide" or "polypeptide" includes a contiguous string of two or more amino acids.

The term "isolated polynucleotide" or "isolated polypeptide" includes a polynucleotide (e.g., RNA or DNA molecule, or a mixed polymer) or a polypeptide, respectively, which is partially or fully separated from other components that are normally found in cells or in recombinant DNA expression systems or any other contaminant. These components include, but are not limited to, cell membranes, cell walls, ribosomes, polymerases, serum components and extraneous genomic sequences.

An isolated polynucleotide (e.g., pOMI2A) or polypeptide will, preferably, be an essentially homogeneous composition of molecules but may contain some heterogeneity.

The term "host cell" includes any cell of any organism that is selected, modified, transfected, transformed, grown, or used or manipulated in any way, for the production of a substance by the cell, for example the expression or replication, by the cell, of a gene, a polynucleotide such as a circular plasmid (e.g., pOMI2A) or RNA or a protein. For example, a host cell may be a mammalian cell or bacterial cell (e.g., *E. coli*) or any isolated cell capable of maintaining pOMI2A plasmid and, in an embodiment of the invention, promoting expression of a polypeptide encoded by a polynucleotide in the plasmid, e.g., an immunoglobulin chain.

Vectors of the invention, such as pOMI2A, may be introduced into host cells according to any of the many techniques known in the art, e.g., dextran-mediated transfection, polybrene-mediated transfection, protoplast fusion, electroporation, calcium phosphate co-precipitation, lipofection, direct microinjection of the vector into nuclei, or any other means appropriate for a given host cell type.

A "cassette" or an "expression cassette" refers to a DNA coding sequence or segment of DNA that codes for an expression product (e.g., peptide or RNA) that can be inserted into a vector, e.g., at defined restriction sites. The expression cassette may comprise a promoter and/or a terminator and/or polyA signal operably linked to the DNA coding sequence.

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with or operably linked to other expression control sequences, including enhancer and repressor sequences or with a nucleic acid to be expressed. An expression control sequence is operably associated with or operably linked to a promoter if it regulates expression from said promoter.

Promoters which may be used to control gene expression include, but are not limited to, SRα promoter (Takebe et al., Molec. and Cell. Bio. 8:466-472 (1988)), the human CMV immediate early promoter (Boshart et al., Cell 41:521-530 (1985); Foecking et al., Gene 45:101-105 (1986)), the mouse CMV immediate early promoter, the SV40 early promoter region (Benoist et al., Nature 290:304-310 (1981)), the *Orgyia pseudotsugata* immediate early promoter, the herpes thymidine kinase promoter (Wagner et al., Proc. Natl. Acad. Sci. USA 78:1441-1445 (1981)), the regulatory sequences of the metallothionein gene (Brinster et al., Nature 296:39-42 (1982)); prokaryotic expression vectors such as the β-lactamase promoter (Villa-Komaroff et al., Proc. Natl. Acad. Sci. USA 75:3727-3731 (1978)), or the tac promoter (DeBoer et al., Proc. Natl. Acad. Sci. USA 80:21-25 (1983)); and promoter elements from yeast or other fungi such as the GAL1, GAL4 or GAL10 promoter, the ADH (alcohol dehydrogenase) promoter, PGK (phosphoglycerol kinase) promoter or the alkaline phosphatase promoter.

Viral long terminal repeat promoters such as the mouse mammary tumor virus long terminal repeat (MMTV-LTR) (Fasel et al., EMBO J. 1(1):3-7 (1982)), the moloney murine sarcoma virus long terminal repeat (Reddy et al., Proc. Natl. Acad. Sci. USA 77(9): 5234-5238 (1980)), the moloney murine leukemia virus long terminal repeat (Van Beveren et al., Proc. Natl. Acad. Sci. USA 77(6): 3307-3311 (1980)), the HIV LTR (Genbank Accession No. AB100245), the bovine foamy virus LTR (Genbank Accession No. NC—001831), RSV 5'-LTR (Genbank Accession No. K00087), the HIV-2 LTR (Genbank Accession No. NC—001722), an avian retroviral LTR (Ju et al., Cell 22: 379-386 (1980)) and the human herpesvirus LTR (Genbank Accession No. NC—001806) may be included in the vectors of the present invention.

Other acceptable promoters include the human and simian CMV5 promoter, the murine CMV promoter, the EF1α promoter, the SV40 promoter, a hybrid CMV promoter for liver specific expression (e.g., made by conjugating CMV immediate early promoter with the transcriptional promoter elements of either human α1-antitrypsin (HAT) or albumin (HAL) promoter), or promoters for hepatoma specific expression (e.g., wherein the transcriptional promoter elements of either human albumin (HAL; about 1000 bp) or human α1-antitrypsin (HAT, about 2000 bp) are combined with a 145 bp long enhancer element of human α1-microglobulin and bikunin precursor gene (AMBP); HAL-AMBP and HAT-AMBP). Table 1 provides examples of promoters that may be utilized.

TABLE 1

| Transcriptional Promoter/Enhancer | | |
|---|---|---|
| DNA element | Structure | Nucleotide sequence |
| Human CMV | promoter/enhancer | Seq ID 1 |
| Simian CMV | promoter/enhancer | Seq ID 2 |
| SV-40 | promoter/enhancer | Seq ID 3 |
| mPGK | promoter/enhancer | Seq ID 4 |

One or more promoters on a single plasmid construct may be employed to drive expression of one or more expression cassettes.

In addition, bacterial promoters, such as the T7 RNA Polymerase promoter or the tac promoter, may be used to control expression.

In one embodiment, the promoter is the human CMV (hCMV) promoter. The hCMV promoter provides a high level of expression in a variety of mammalian cell types.

A coding sequence is "under the control of", "functionally associated with", "operably linked to" or "operably associated with" transcriptional and translational control sequences in a cell when the sequences direct or regulate expression of the sequence. For example, a promoter operably linked to a gene will direct RNA polymerase mediated transcription of the coding sequence into RNA, preferably mRNA, which may then be spliced (if it contains introns) and, optionally, translated into a protein encoded by the coding sequence. A terminator/polyA signal operably linked to a gene terminates transcription of the gene into RNA and directs addition of a polyA signal onto the RNA.

The terms "express" and "expression" mean allowing or causing the information in a gene, RNA or DNA sequence to become manifest; for example, producing a protein by activating the cellular functions involved in transcription and translation of a corresponding gene. "Express" and "expression" include transcription of DNA to RNA and of RNA to protein. A DNA sequence is expressed in or by a cell to form an "expression product" such as an RNA (e.g., mRNA) or a protein. The expression product itself may also be said to be "expressed" by the cell.

The term "transformation" means the introduction of a nucleic acid into a cell. The introduced gene or sequence may be called a "clone". A host cell that receives the introduced DNA or RNA has been "transformed" and is a "transformant" or a "clone." The DNA or RNA introduced to a host cell can come from any source, including cells of the same genus or species as the host cell, or from cells of a different genus or species. Examples of transformation methods which are very well known in the art include liposome delivery, electroporation, CaPO4 transformation, DEAE-Dextran transformation, microinjection and viral infection.

The present invention includes vectors which comprise polynucleotides of the invention. The term "vector" may refer to a vehicle (e.g., a plasmid) by which a DNA or RNA sequence can be introduced into a host cell, so as to transform the host and, optionally, promote expression and/or replication of the introduced sequence.

The polynucleotides of the invention may be expressed in an expression system. The term "expression system" means a host cell and compatible vector which, under suitable conditions, can express a protein or nucleic acid which is carried by the vector and introduced to the host cell. Common expression systems include *E. coli* host cells and plasmid vectors, insect host cells and baculovirus vectors, and mammalian host cells and vectors such as plasmids, cosmids, BACs, YACs and viruses such as adenovirus and adenovirus associated virus (AAV).

The terms "immunostimulatory cytokine" or "immunostimulatory cytokines" refer to protein naturally secreted by cells involved in immunity that have the capacity to stimulate an immune response. Examples of immunostimulatory cytokines are provided in Table 2A and 2B.

The phrase "genetic adjuvants containing shared tumor antigens" as used herein refers to fusion proteins of receptor tyrosine kinases and known tumor antigens as described in Table 4.

II. General

The present invention provides expression vectors that allow adequate expression of multiple proteins following transfection of an in vivo cell, particularly a tumor cell.

Vectors are provided that contain some or all of the modifications described herein designed to improve their efficacy and safety. The optimization of the vectors includes the incorporation of sequences encoding appropriate peptides and the tailoring of sites to maximize gene expression. A peptide is understood to be any translation product regardless of size, and whether or not post-translationally modified, as, for example, in glycosylation and phosphorylation.

The present invention provides expression vectors comprising the translation control element, e.g., P2A, operatively linked to gene sequences to be expressed. In certain embodiments, the expression vector comprises at least two nucleic acid sequences to be translated and the translation control element is operatively linked to at least one of the sequences to be translated. Vectors are known or can be constructed by those skilled in the art and contain all expression elements necessary to achieve the desired transcription of the sequences in addition to the sequence of the present invention as shown in the Examples herein below. The vectors contain elements for use in either prokaryotic or eukaryotic host systems depending on their use. One of ordinary skill in the art will know which host systems are compatible with a particular vector.

Recombinant gene expression depends upon transcription of the appropriate gene and efficient translation of the message. A failure to perform correctly either one of these processes can result in the failure of a given gene to be expressed. This is further complicated when more than one gene needs to be expressed from a single plasmid. Traditionally, internal ribosomal entry sites (IRES's) were used between the genes to be expressed. IRES's have limitations because of their size and the translation efficiency of the second gene is much lower than the first. Recent studies have found that the use of picornaviru polyprotein 2A ("P2A") peptide results in stoichiometric expression of multiple proteins flanking the P2A peptide (see, e.g, Kim et al (2011) *PloS One* 6:318556).

Adequate recombinant expression of diverse immunomodulators including, e.g., heterodimeric proteins such as IL-12, IL-15/IL-15Ra, IL-23, IL-27; and genetic adjuvants containing shared tumor antigens, e.g., Flt3L-NYESO-1 fusion protein, in expression plasmids, This is especially true when the plasmid is delived to a tumor (intratumoral delivery) via in vivo electroporation.

Examples of immunostimulatory cytokines are provided in Table 2A.

TABLE 2A

Immunostimulatory cytokines.

| Gene | Structure | Sequence nucleotide | Sequence Protein |
|---|---|---|---|
| IL-12 | p35 and p40 subunits heterodimer | SEQ ID 5 | NP_000873.2, NP_002178.2 |
| IL-12 (mouse) | p35 and p40 subunits heterodimer | SEQ ID 6 | NP_001152896.1, NP_001290173.1 |
| IL-12 (canine) | p35 and p40 subunits heterodimer | SEQ ID 7 | XP_013965819.1, NP_001003292.1 |
| IL-15/ IL-15 receptor | IL15 and soluble IL15 receptor heterodimer | SEQ ID 8 SEQ ID 10 (IL-15Ra-Fc fusion) | SEQ ID 9, SEQ ID 11 (IL-15Ra-Fc fusion) |
| IL-23 | p19 and p40 subunits heterodimer | XM_011538477.2 NM_002187.2 | XP_011536779.1 NP_002178.2 |
| IL-27 | p28 and IL27B subunits heterodimer | NM_145659.3; NM_005755.2 | NP_663634.2; NP_005746.2 |
| IFNα | Full length protein | NM_006900.3. NM_024013.2. | NP_008831.3 NP_076918.1 |
| IFNβ | Full length protein | NM_002176.3. | NP_002167.1 |
| INFγ | Full length protein | SEQ ID 12 | NP_000610.2 |
| TNFα | Full length protein | X02910 | ADV31546 |
| IL-4 | Full length protein | NM_000589.3 | NP_000580.1 |
| IL-7 | Full length protein | NM_001199886.1 | NP_001186815.1 |
| IL-9 | Full length protein | NM_000590.1 | NP_000581.1 |
| IL-21 | Full length protein | NM_021803.3 | NP_068575.1 |
| IL-2 | Full length protein | NM_000586.3. | NP_000577.2 |

Also contemplated for immunostimulation are innate immunity regulators as described in Table 2B.

TABLE 2B

Innate immunity regulators

| Gene | Structure | Reference |
|---|---|---|
| IL-33 | Recombinant protein: amino acid 109 to 266 | Gao et al., J. Immunol. 2015; 194: 438 |
| Flagellin | TLR5 binding domain | Hayashi et al., Nature 2001; 410: 1099 |
| IL-10 Receptor | Recombinant soluble, secreted protein | Marchi et al., Cancer Gene Therapy 2011, 18: 110 |
| Sting Receptor | Dominant-active mutant | pUNO1-hSTING-M155 (InvivoGen) |
| IRF3 | Dominant-active mutant | pUNO1-hsaIRF3 (invivoGen) |

TABLE 3

Genetic Adjuvants

| Gene | Structure | Reference |
|---|---|---|
| Flt3 ligand | Extralcellular domain | XM_017026533.1 |
| LAMP-1 | (ECD) | XM_011537494.1 |
| Calreticulin | Full length protein | NM_004343; Cheng et al., 2001, J Clin Invest. 108: 669 |
| Human heat shock protein 96 | Full length protein | Rivoltini et al., 2003. J. Immunol. 171: 3467 |
| GM-CSF | Full length protein | NM_000758.3 |
| CSF Receptor 1 | | NM_001288705.2 |

TABLE 4

Genetic Adjuvants fused to shared tumor antigens or viral antigens (Flt3L protein fusions)

| Gene | Structure | Reference |
|---|---|---|
| NY-ESO-1 | Fusion of full length protein to ECD of Flt3L | SEQ ID 13 (DNA); SEQ ID 14 (protein):, Gnjatic et al., Advances in Cancer Res. 2006 |
| NY-ESO-1 | Fusion of amino acid# 80-180 to ECD of Flt3L | SEQ ID 15 (DNA); SEQ ID 16 (protein):, Sabado-R L, Cancer Immunol Res 2015 MARCH; 3(3) |
| NY-ESO-1 | Fusion of overlapping peptides: Amino acid# 81-100, 87-111, 157-165, 157-170, 161-180 to ECD of Flt3L | SEQ ID 17 (DNA); SEQ ID 18 (protein): |
| NY-ESO-1 | Fusion of amino acid # 157-165 to ECD of Flt3L | RAPOPORT-AP, NATURE MEDICINE, 2015 AUGUST 21(8) |
| MAGE-A1 | Fusion of full legth protein or antigenic peptides to ECD of Flt3L | Almeida et al., Nuc, Acids Res 2009; |
| MAGE-A2 | Fusion of full legth protein or antigenic peptides to ECD of Flt3L | Almeida et al., Nuc, Acids Res 2009; |
| MAGE-A3 | Fusion of full legth protein or antigenic peptides to ECD of Flt3L | Almeida et al., Nuc, Acids Res 2009; |
| MAGE-A10 | Fusion of full legth protein or antigenic peptides to ECD of Flt3L | Almeida et al., Nuc, Acids Res 2009; |
| SSX-2 | Fusion of full legth protein or antigenic peptides to ECD of Flt3L | Almeida et al., Nuc, Acids Res 2009; |

TABLE 4-continued

| Genetic Adjuvants fused to shared tumor antigens or viral antigens (Flt3L protein fusions) | | |
|---|---|---|
| Gene | Structure | Reference |
| MART-1 | Fusion of full length protein or antigenic peptide ELAGIGILTV to ECD of Flt3L | Li et al., J. Immunol. 2010, 184:452 |
| Tyrosinase | Fusion of antigenic peptide YMDGTMSQV to ECD of Flt3L | Skipper et al., J. Exp. Med 1996, 183:527 |
| Gp100 | Fusion of full legth protein or antigenic peptides to ECD of Flt3L | Bakker et al., J. Exp. Med. 1994, 179:1005 |
| Survivin | Fusion of full legth protein or antigenic peptide ELTLGEFLKL to ECD of Flt3L | Schmidt et al., Blood 2002, 102:571 |
| hTERT | Fusion of full legth protein or antigenic peptides to ECD of Flt3L | Vonderheide et al., Nature 2002, 21:674 |
| PRS pan-DR | Fusion of full legth protein or antigenic peptides to ECD of Flt3L | Almeida et al., Nuc, Acids Res 2009; |
| B7-H6 | Full length protein or fusion of full legth protein to ECD of Flt3L | Brandt et al., J. Exp Med. 2009, 206:1495 |
| HPV E7 | Full length protein or fusion of full legth protein to ECD of Flt3L | Huang et al., Cancer Res. 2001 61:1080; Seo et al., Vaccine 2009 27:5906; Lin et al., |
| HPV16 E6/E7 | 1-85 aa E6, 1-65 aa E7, 71-158 aa E6, 51-98 aa E7 fused to ECD of Flt3L | Kim et al, Nature 2014 5:5317 |
| HPV16 E6/E7 | E6 mutant L50A; E6 mutant ETNL146-151AAAA; E7 mutant H2P; E7 mutant C24G; E7 mutant E46A; E7 mutant L67R | Wieking et al., 2012, Cancer Gene Ther. 19:667 |
| HPV11 E6 | 44-51 aa E6 | Peng et al., 2010, Larynoscope 120:504 |
| HPV6b/11E7 | 21-29 aa E7, 82-90 aa E7 | Peng et al., 2016, Cancer Immunol. Immunother. 65:261 |
| HCV-NS3 | Fusion of full legth protein or antigenic peptides fused to ECD of Flt3L | Grubor-Bauk et al., 2016, Gene Ther. 23:26 |
| Influenza HA and NA | Fusion of full legth protein or antigenic peptides to ECD of Flt3L | Chow et al., 1979. Infect Immun. 25:103 |
| Polyoma-virus | MCPyV LTA aa1-258, aa136-160; various other peptides from VP1, LTA, and STA | Zeng et al., Vaccine 2012 30:1322; Lyngaa et al., 2014, Clin Can Res 2014, 20:1768 |

Several studies have shown that the translation modifiers can efficiently drive translation of genes encoding multimeric proteins (see, e.g., Kim, et al. (2011) PloS ONE 6:1-8; Ibrahimi, et al. (2009) *Human Gene Ther.* 20:845-860; Szymczak, et al. (2004) *Nat. Biotechnol.* 22:589-594). Table 5 provides examples of translational modifiers.

TABLE 5

| Translational modifiers | | |
|---|---|---|
| DNA element | Structure | Nucleotide sequence |
| P2A | Exon skipping motif in mRNA | Seq ID 19 |
| T2A | Exon skipping motif in mRNA | Seq ID 20 |
| E2A | Exon skipping motif in mRNA | Seq ID 21 |
| F2A | Exon skipping motif in mRNA | Seq ID 21 |
| IRES | Internal Ribosome Entry Site | Seq ID 23 |

III. Devices and Uses

The invention finds use in intratumoral gene electrotransfer. In particular the current plasmid constructs can be used to generate adequate concentrations of of several recombinantly expressed immunomodulatory molecules such as, multimeric cytokines or combination of multimeric cytokines, co-stimulatory molecules in native or engineered forms, genetic adjuvants containing shared tumor antigens, etc. To achieve transfer of the instant plasmid constructs into a tissue, e.g., a tumor, an electroporation device is employed.

The devices and methods of the present embodiment work to treat cancerous tumors by delivering electrical therapy continuously and/or in pulses for a period of time ranging from a fraction of a second to several days, weeks, and/or months to tumors. In a preferred embodiment, electrical therapy is direct current electrical therapy.

The term "electroporation" (i.e. rendering cellular membranes permeable) as used herein may be caused by any amount of coulombs, voltage, and/or current delivered to a patient in any period of time sufficient to open holes in cellular membranes (e.g. to allow diffusion of molecules such as pharmaceuticals, solutions, genes, and other agents into a viable cell).

Delivering electrical therapy to tissue causes a series of biological and electrochemical reactions. At a high enough voltage, cellular structures and cellular metabolism are severely disturbed by the application of electrical therapy. Although both cancerous and non-cancerous cells are destroyed at certain levels of electrical therapy tumor cells are more sensitive to changes in their microenvironment than are non-cancerous cells. Distributions of macroelements and microelements are changed as a result of electrical therapy. Destruction of cells in the vicinity of the electroporation is known as irreversible electroporation.

The use of reversible electroporation is also contemplated. Reversible electroporation occurs when the electricity applied with the electrodes is below the electric field threshold of the target tissue. Because the electricity applied is below the cells' threshold, cells are able to repair their phospholipid bilayer and continue on with their normal cell functions. Reversible electroporation is typically done with treatments that involve getting a drug or gene (or other molecule that is not normally permeable to the cell membrane) into the cell. (Garcia, et al. (2010) "Non-thermal irreversible electroporation for deep intracranial disorders". 2010 *Annual International Conference of the IEEE Engineering in Medicine and Biology:* 2743-6.)

In a single electrode configuration, voltage may be applied for fractions of seconds to hours between a lead electrode and the generator housing, to begin destruction of cancerous tissue. Application of a given voltage may be in a series of pulses, with each pulse lasting fractions of a second to several minutes. In certain embodiments, the pulse duration or width can be from about. Low voltage may also be applied for of a duration of fractions of seconds to minutes, which may attract white blood cells to the tumor site. In this way, the cell mediated immune system may remove dead tumor cells and may develop antibodies against tumor cells. Furthermore, the stimulated immune system may attack borderline tumor cells and metastases.

Various adjuvants may be used to increase any immunological response, depending on the host species, including but not limited to Freund's adjuvant (complete and incomplete), mineral salts such as aluminum hydroxide or aluminum phosphate, various cytokines, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diptheria toxoid, ovalbumin, cholera toxin or fragments thereof.

U.S. Pat. No. 7,245,963 by Draghia-Akli, et al. describes modular electrode systems and their use for facilitating the introduction of a biomolecule into cells of a selected tissue in a body or plant. The modular electrode systems comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk (see, e.g., U.S. Patent Pub. 2005/0052630) is hereby incorporated by reference.

The electrode arrays and methods described in U.S. Pat. No. 7,245,963 and U.S. Patent Pub. 2005/0052630 are adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes.

Also encompassed are electroporation devices incorporating electrochemical impedance spectroscopy ("EIS"). Such devices provide real-time information on in vivo, in particular, intratumoral electroporation efficiency, allowing for the the optimization of conditions. Examples of electroporation devices incorporating EIS can be found, e.g., in WO2016161201, which is hereby incorporated by reference.

Other alternative electroporation technologies are also contemplated. In vivo plasmid delivery can also be performed using cold plasma. Plasma is one of the four fundamental states of matter, the others being solid, liquid, and gas. Plasma is an electrically neutral medium of unbound positive and negative particles (i.e. the overall charge of a plasma is roughly zero). A plasma can be created by heating a gas or subjecting it to a strong electromagnetic field, applied with a laser or microwave generator. This decreases or increases the number of electrons, creating positive or negative charged particles called ions (Luo, et al. (1998) *Phys. Plasma* 5:2868-2870) and is accompanied by the dissociation of molecular bonds, if present.

Cold plasmas (i.e., non-thermal plasmas) are produced by the delivery of pulsed high voltage signals to a suitable electrode. Cold plasma devices may take the form of a gas jet device or a dielectric barrier discharge (DBD) device. Cold temperature plasmas have attracted a great deal of enthusiasm and interest by virtue of their provision of plasmas at relatively low gas temperatures. The provision of plasmas at such a temperature is of interest to a variety of applications, including wound healing, anti-bacterial processes, various other medical therapies and sterilization. As noted earlier, cold plasmas (i.e., non-thermal plasmas) are produced by the delivery of pulsed high voltage signals to a suitable electrode. Cold plasma devices may take the form of a gas jet device, a dielectric barrier discharge (DBD) device or multi-frequency harmonic-rich power supply.

Dielectric barrier discharge device, relies on a different process to generate the cold plasma. A dielectric barrier discharge (DBD) device contains at least one conductive electrode covered by a dielectric layer. The electrical return path is formed by the ground that can be provided by the target substrate undergoing the cold plasma treatment or by providing an in-built ground for the electrode. Energy for the dielectric barrier discharge device can be provided by a high voltage power supply, such as that mentioned above. More generally, energy is input to the dielectric barrier discharge device in the form of pulsed DC electrical voltage to form the plasma discharge. By virtue of the dielectric layer, the discharge is separated from the conductive electrode and electrode etching and gas heating is reduced. The pulsed DC electrical voltage can be varied in amplitude and frequency to achieve varying regimes of operation. Any device incorporating such a principle of cold plasma generation (e.g., a DBD electrode device) falls within the scope of various embodiments of the present invention.

Cold plasma has been employed to transfect cells with foreign nucleic acids. In particular, transfection of tumor cells (see, e.g., Connolly, et al. (2012) *Human Vaccines & Immunotherapeutics* 8:1729-1733; and Connolly et al (2015) *Bioelectrochemistry* 103: 15-21).

The devices are contemplated for use in patients afflicted with cancer or other non-cancerous (benign) growths. These growths may manifest themselves as any of a lesion, polyp, neoplasm (e.g. papillary urothelial neoplasm), papilloma, malignancy, tumor (e.g. Klatskin tumor, hilar tumor, noninvasive papillary urothelial tumor, germ cell tumor, Ewing's tumor, Askin's tumor, primitive neuroectodermal tumor, Leydig cell tumor, Wilms' tumor, Sertoli cell tumor), sarcoma, carcinoma (e.g. squamous cell carcinoma, cloacogenic carcinoma, adenocarcinoma, adenosquamous carcinoma, cholangiocarcinoma, hepatocellular carcinoma, invasive papillary urothelial carcinoma, flat urothelial carcinoma), lump, or any other type of cancerous or non-cancerous growth. Tumors treated with the devices and methods of the present embodiment may be any of noninvasive, invasive, superficial, papillary, flat, metastatic, localized, unicentric, multicentric, low grade, and high grade.

The devices are contemplated for use in numerous types of malignant tumors (i.e. cancer) and benign tumors. For example, the devices and methods described herein are contemplated for use in adrenal cortical cancer, anal cancer, bile duct cancer (e.g. periphilar cancer, distal bile duct cancer, intrahepatic bile duct cancer) bladder cancer, benign and cancerous bone cancer (e.g. osteoma, osteoid osteoma, osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astocytoma, oligodendrogliomas, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating lobular carcinoma, lobular carcinoma in situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenocanthoma, papillary serous adnocarcinoma, clear cell) esophagus cancer, gallbladder cancer (mucinous adenocarcinoma, small cell carcinoma), gastrointestinal carcinoid tumors (e.g. choriocarcinoma, chorioadenoma destruens), Hodgkin's disease, non-Hodgkin's lymphoma, Cutaneous T-Cell Lymphoma (CTCL), Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyosarcoma), salivary gland cancer, skin cancer, both melanoma and non-melanoma skin cancer (including Merkel Cell Carcinoma), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma).

IV. Combination Therapies

It is contemplated that intratumoral electroporation of DNA encoding immune-modulory proteins can be administered with other therapeutic entities. Table 6 provides possible combinations. Administration of the combination therapies can be achieved by electroporation alone or a combination of electroporation and systemic delivery.

TABLE 6

Combination Therapies

| Combination | Proposed delivery method | Reference |
|---|---|---|
| IT-pOMI-2A/EP + Anti-PD1 antagonist Ab | Intratumoral Electroporation ("IT-EP") of plasmids encoding cytokines, co-stimulators, immune-directors in pOMI-2A plus systemic anti-PD-1 Ab treatment<br>1. co-administration<br>2. Administration of IT-EP, followed by systemic anti-PD-1 inhibitor | i.e. Quetglas et al. Can, Immol, Res. 2015, 3: 449 |
| IT-pOMI-2A/EP + anti-PDL1 antagonist Ab | IT-EP of pOMI-2A/EP plus systemic anti-PDL-1 Ab treatment<br>1. co-administration<br>2. sequential administration of IT-EP, followed by systemic anti-PDL-1 inhibitor | |

TABLE 6-continued

| Combination Therapies | | |
|---|---|---|
| Combination | Proposed delivery method | Reference |
| IT-pOMI-2A/EP + CTLA4 agonist antibody ("Ab") or ligand | IT-EP of pOMI-2A/EP plus systemic delivery of CTLA4 antagonist Abs<br>1. co-administration<br>2. sequential administration of IT-EP, followed by systemic anti-CTLA4 antagonist Ab | Vom Berg et al., 2013, J. Exp. Med. 210: 2803 |
| IT-pOMI-2A/EP + tumor vaccine | 1. EP of IT-pOMI-2A + cytotoxic agent (separately) to create local tumor antigen pool<br>2. EP of IT-pOMI-2A + system delivery of tumor vaccine (i.e gp100 peptide vaccine for melanoma) | Vergati et al., 2010. *J. Biomed. Biotechnol.* 2010: Article ID 596432 |
| IT-pOMI-2A/EP + Bleomycin, Gemzar, Cytozan, 5-fluoro-uracil, Adriamycin or other chemotherapeutic agent | 1. intratumoral EP of drug + IT-pOMI-2A<br>2. EP of IT-pOMI-2A + system delivery of drug | i.e. Zhang et al., 2015, J. Immunother. 38: 137 |
| IT-pOMI-2A/EP + small molecule inhibitors (i.e. Sunitiinib, Imatinib, Vemurafenib, Trastuzumab, Bevacizumab , Cetuximb, rapamycin, Bortezomib, PI3K-AKT inhibitors, IAP inhibitors | 1. EP of IT-pOMI-2A combined with local drug delivery<br>2. EP of IT-pOMI-2A combined with systemic drug treatment | Hu-Lieskovan et al., (2014) *J. Clin. Oncol.* 32(21 ): 2248-54 Vanneman and Dranoff (2014) *Nat. Rev. Cancer* 12(4): 237-251 |
| IT-pOMI-2A/EP + targeted radiation | Sublethal radiation dose locally at tumor site, followed by IT-pOMI-2A/EP | Almo S C, Guha C. (2014) *Radiation Res.* 182(2): 230-238. |

The broad scope of this invention is best understood with reference to the following examples, which are not intended to limit the inventions to the specific embodiments.

EXAMPLES

I. General Methods

Standard methods in molecular biology are described. Maniatis et al. (1982) Molecular Cloning, A Laboratory Manual, Cold Spring Harbor Laboratory Press, Cold Spring Harbor, N.Y.; Sambrook and Russell (2001) Molecular Cloning, 3rd ed., Cold Spring Harbor Laboratory Press, Cold Spring Harbor, N.Y.; Wu (1993) Recombinant DNA, Vol. 217, Academic Press, San Diego, Calif. Standard methods also appear in Ausbel et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described. Coligan et al. (2000) *Current Protocols in Protein Science*, Vol. 1, John Wiley and Sons, Inc., New York. Chemical analysis, chemical modification, post-translational modification, production of fusion proteins, glycosylation of proteins are described. See, e.g., Coligan et al. (2000) *Current Protocols in Protein Science, Vol.* 2, John Wiley and Sons, Inc., New York; Ausubel et al. (2001) *Current Protocols in Molecular Biology, Vol.* 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391. Production, purification, and fragmentation of polyclonal and monoclonal antibodies are described. Coligan et al. (2001) *Current Protocols in Immunology, Vol.* 1, John Wiley and Sons, Inc., New York; Harlow and Lane (1999) *Using Antibodies*, Cold Spring Harbor Laboratory Press, Cold Spring Harbor, N.Y.; Harlow and Lane, supra. Standard techniques for characterizing ligand/receptor interactions are available. See, e.g., Coligan et al. (2001) *Current Protocols in Immunology, Vol.* 4, John Wiley, Inc., New York.

Methods for flow cytometry, including fluorescence activated cell sorting detection systems (FACS®), are available. See, e.g., Owens et al. (1994) Flow Cytometry Principles for Clinical Laboratory Practice, John Wiley and Sons, Hoboken, N.J.; GivAn (2001) Flow Cytometry, 2nd ed.; Wiley-Liss, Hoboken, N.J.; Shapiro (2003) Practical Flow Cytometry, John Wiley and Sons, Hoboken, N.J. Fluorescent reagents suitable for modifying nucleic acids, including nucleic acid primers and probes, polypeptides, and antibodies, for use, e.g., as diagnostic reagents, are available. Molecular Probes (2003) Catalogue, Molecular Probes, Inc., Eugene, Oreg.; Sigma-Aldrich (2003) Catalogue, St. Louis, Mo.

Standard methods of histology of the immune system are described. See, e.g., Muller-Harmelink (ed.) (1986) Human Thymus: Histopathology and Pathology, Springer Verlag, New York, N.Y.; Hiatt, et al. (2000) Color Atlas of Histology, Lippincott, Williams, and Wilkins, Phila, Pa.; Louis, et al. (2002) Basic Histology: Text and Atlas, McGraw-Hill, New York, N.Y.

Software packages and databases for determining, e.g., antigenic fragments, leader sequences, protein folding, functional domains, glycosylation sites, and sequence alignments, are available. See, e.g., Gen Bank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne et al. (2000) *Bioinformatics* 16: 741-742; Menne et al. (2000) *Bioinformatics Applications Note* 16:741-742; Wren et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690.

II. Subcloning of Human IL-12 p35 and p40 Subunits into pOMI2A

A pUMVC3 backbone was purchased from Aldevron (Fargo, N. Dak.). A 1071 bp DNA fragment (gene block) encoding the translation modulating element P2A linked in-frame to hIL12p40 (P2A-hIL12p40) was purchased from IDT (Coralville, Iowa). The p40 geneblock was PCR amplified using Phusion polymerase (NEB, Ipswich Mass., cat.# M0530S) and ligated into pUMVC3 downstream of the CMV promoter/enhancer using standard restriction enzyme pairing and T4 DNA ligase (Life Technologies, Grand Island N.Y., cat.#15224-017). Positives clones of P2A-hIL12p40/pOMI2A were identified via restriction enzyme digests and verified with DNA sequencing.

Human p35 was ordered as a 789 bp geneblock from IDT (Coralville Iowa) with internal BamH1, BgIII and Xba1 sites removed to facilitate cloning. The p35 geneblock was PCR amplified as described above and ligated upstream of the p40 geneblock in P2A-hIL12p40/pOMI2A. Positives clones of hIL12p35-P2A-p40/pOMI2A were identified via restriction enzyme digests and verified with DNA sequencing.

Other heterodimeric cytokines, single chain cytokines, or innate immune-regulators (Tables 2A, 2B) are cloned into pOMI2A vectors similar to IL-12.

III. Subcloning of IL-15-P2A-IL-15Rα into pOMI2A

A 1384 bp geneblock was ordered from IDT encoding hIL15 and hIL15Rα, linked together in-frame with the translation-modulating element P2A. The geneblock was PCR amplified as described above and ligated into pOMI2A. Positives clones were identified via restriction enzyme digests and verified with DNA sequencing.

A mutant form of IL-15 showing increased activity was also subcloned into the pOMI2A vector as above (see, e.g., Zhu, et al. (2009) *J. Immunol.* 183:3598).

IV. Subcloning of IL-15-P2A-IL-15Rα-IgG1Fc into pOMI2A

A 708 bp DNA geneblock was ordered from IDT encoding the human IgG1 Fc sequence. The geneblock was PCR amplified as described above and ligated downstream of IL-15-P2A-IL-15Rα in pOMI2A. The stop site between IL15Ra and Fc was then removed via a QuikChange mutagenesis reaction (Agilent Technologies, La Jolla Calif., cat.#200521). Finally, the complete IL15-P2A-IL15Rα-IgG1Fc sequence was PCR amplified and ligated back into pOMI2A.

V. Subcloning of INFγ into pOMI2A

A 501 bp DNA geneblock was ordered from IDT encoding the full-length human INF gamma coding sequence. The geneblock was PCR amplified as described above and ligated into pUMVC3 (Aldeveron). Positives clones were identified via restriction enzyme digests and verified with DNA sequencing. Finally, the IFNγ insert was PCR amplified and ligated into various pOMI2A vectors.

VI. Generation of FLT3L-Antigen Fusion Protein Constructs

The FMS-like tyrosine kinase 3 ligand (Flt3L) has been shown to direct antigen to antigen presenting cells (APC) for preferential presentation to T cells (Kim et al. Nat Comm. 2014, Kreiter et al., Cancer Res. 2011, 71:6132). A soluble, secreted form of Flt3L is fused to a variety of protein or peptide antigen s (Table 4; Kim et al. Nat Comm. 2014). An example protocol is given for generating a FLT3L-NY-ESO-1 fusion protein construct.

Three gene blocks were obtained from IDT that each contained the IgK signal peptide sequence followed by the ECD of Flt3L, a short hinge region, and three different segments of the NY-ESO-1 antigen. PCR was used to add flanking restriction sites and introduce these three fusion protein constructs into pUMVC3 (Sequence ID Nos. 17-22). Flt3L was also fused to a concatamer of 3 peptides containing the SIINFEKL peptide antigen from the ovalbumin gene (Seq ID 24) for pre-clinical studies in mice. From pUMVC3, these fusion constructs are introduced into pOMI-2×2A (described below).

An alternative fusion protein using viral antigens (Table 4) is constructed using the same method.

An alternative fusion protein with full length calreticulin (Table 3) is constructed using the same method.

In addition to identified shared tumor antigens, patient-specific neoantigens could be identified and immunogenic peptide antigens tailored to that patient can be fused to Flt3L for personalized therapy via intratumoral electroporation, (see, e.g., Beckhove et al., J. Clin. Invest. 2010, 120:2230).

Versions of all immune-modulatory proteins are constructed in parallel using mouse homolog sequences and are used in pre-clinical studies.

Figure 3A:
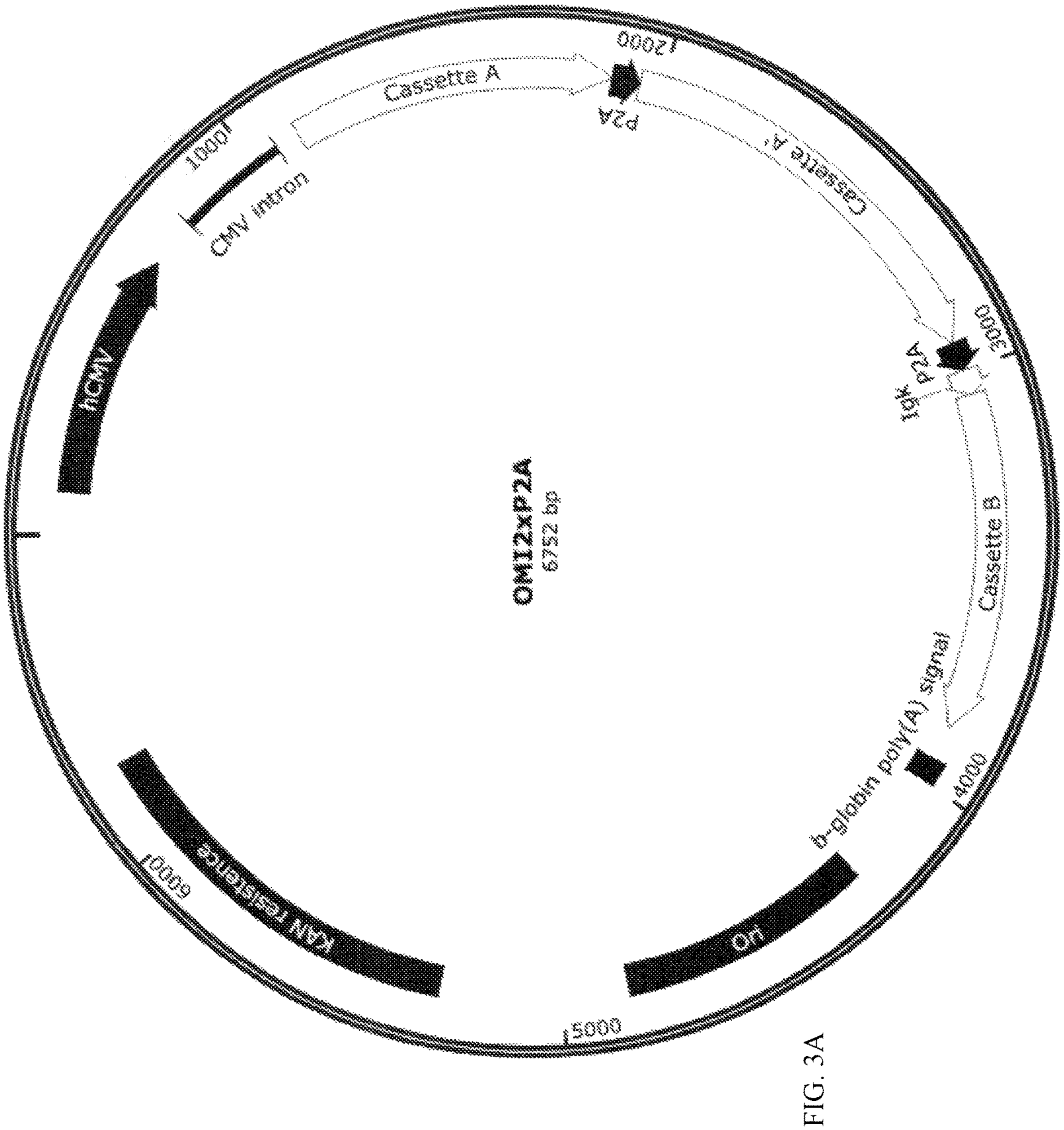
FIG. 3 shows the plasmid maps for vectors for expression of more than two immunomodulatory gene cassettes (A) OMI2×2A: Promoter 1+gene cassette A+P2A+gene cassette B+P2A+gene cassette B' (B) OMI2×2A': Promoter 1+gene cassette A+P2A+gene cassette A'+P2A+gene cassette B.
Figure 3B:
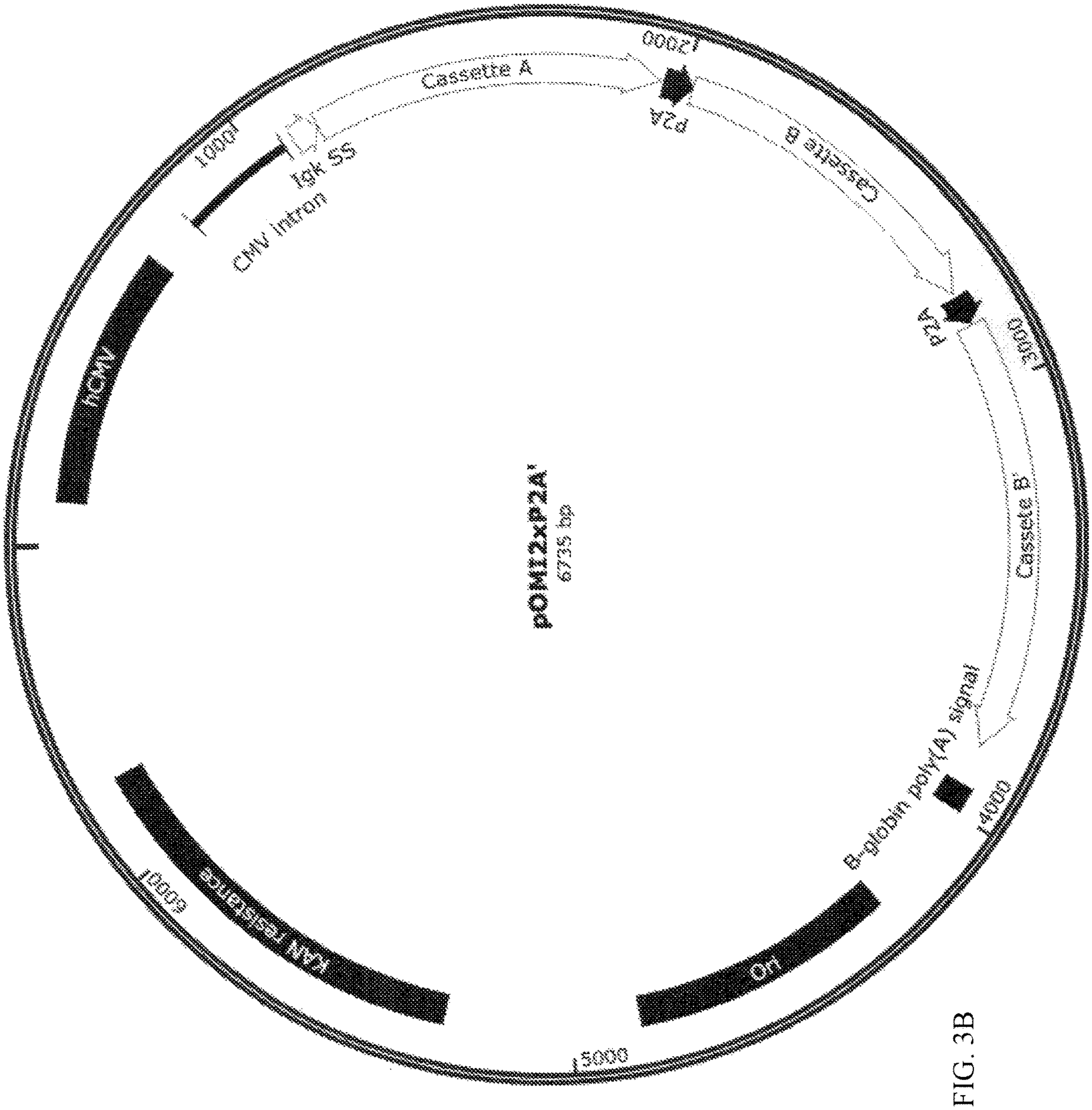

VII. Generation of OMI-2×2A for Expression of Three Proteins from a Single Transcript A schematic diagram of the vector is shown in FIG. 3. All three genes are expressed from the same promoter, with intervening exon skipping motifs to allow all three proteins to be expressed from a single polycistronic message.

An example subcloning protocol is given for IL-12 heterodimeric cytokine, and Flt3L-NY-ESO-1. A DNA geneblock (IDT) encoding FLT3L-NYESO-1 was PCR-amplified with an upstream P2A site and flanking restriction sites and ligated downstream of hIL-12p40. Quikchange mutagenesis (Agilent, Santa Clara, USA) was performed to delete the stop site 3' of p40. Positives clones were identified via restriction enzyme digests and verified with DNA sequencing.

A forth gene can be added either upstream or downstream of the three genes already in the polycistronic message using the same methods.

XIII. ELISA

Clones of OMI2A-IL-12 and OMI2A-IL-15/IL-15R, and OMI2x2A-IL12-Flt3L-NY-ESO-1 were transfected into HEK293 cells using TransIT LT-1 (Mirus, Madison Wis., cat.# MIR 2300) according to the manufacturers recommendations. Two days later, supernatants were collected and spun for 5 minutes at 3000 rpm to remove any cell debris. Cleared supernatants were transferred to new tubes, aliquoted and frozen at −86° C. The levels of hIL-12p70 and hIL15-IL15R□ heterodimeric proteins in the conditioned media were quantitated using an ELISA that specifically detects the complexes (R&D Systems, Minneapolis Minn. cat.# DY1270, DY6924). The level of FLT3L-NYESO-1 fusion protein were quantified by ELISA with anti-Flt3L antibodies (R&D Systems, Minneapolis Minn. cat.# DY308).

Figure 4:
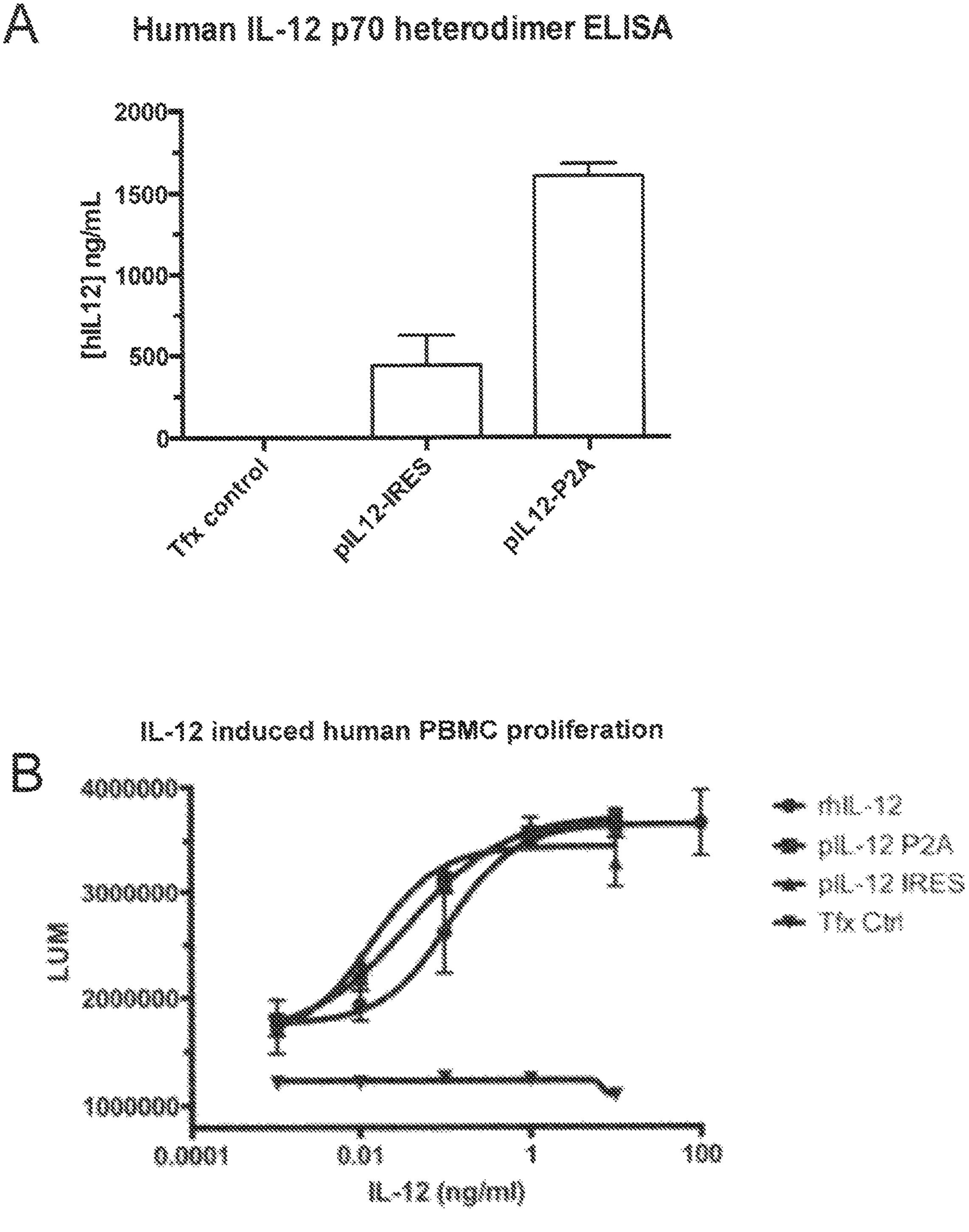
FIG. 4 (A) illustrates the protein expression levels of cells transfected with pOMI2A-hIL-12 and pOMIIRES-hIL-12, as measured by ELISA. (B) illustrates the proliferative activity of IL-12 produced by transfection of pOMI2A-hIL-12 in comparison to pOMIIRES-hIL-12 on peripheral blood monocyte cells (PBMC).
Figure 5:
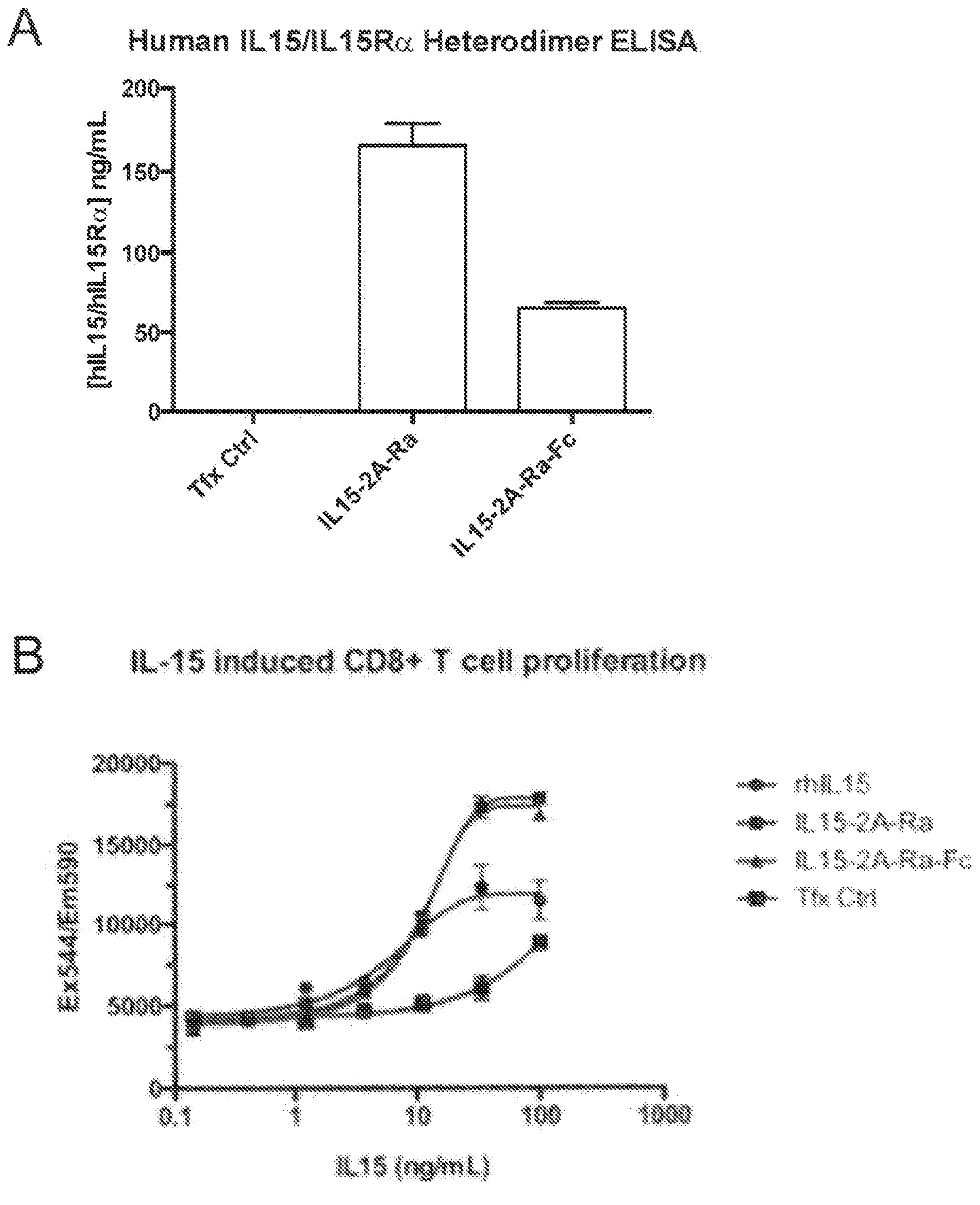
FIG. 5 (A) illustrates the protein expression levels of cells transfected with pOMI2A-hIL-15/hIL-15Ra and pOMI2A-IL-15/IL-15Ra-Fc, as measured by ELISA. (B) illustrates the proliferative activity on human primary CD8+ T cells of hIL-15 produced by transfection of pOMI2A-hIL-15/IL-15Ra and pOMI2A-hIL-15/IL-15Ra-Fc.

Comparison of hIL-12p70 expression and secretion from cells transfected with pOMI2A-hIL-12 and pOMIIRES-hIL-12 revealed that pOMI2A-hIL-12 generated higher expression levels of the mature heterodimeric p70 protein secreted by transfected cells as measured by ELISA (FIG. 4A). Expression and secretion from cells transfected with pOMI2A-hIL-15/IL-15Rα and pOMI2A-hIL-15/IL-15RαFc domain were measured by ELISA and are shown in FIG. 5A.

TABLE 7

Expression and secretion of IL-12 p70 and Flt3L-NY-ESO-1 fusion protein from cells transfected with OMI2x2A-IL-12-Flt3L-NY-ESO-1 were measured by ELISA and are shown.

| Secreted protein | ng/ml; Mean +/− SEM |
|---|---|
| IL-12 p70 | 1364 +/− 5.5 |
| Flt3L-NY-ESO-1 fusion protein | 25.1 +/− 3.1 |

XIX. Protein Detection by Western Blots

For Western Blotting, Laemmli SDS sample buffer NuPAGE 4X LDS, ThermoFisher Scientific) was added to each sample and boiled at 100° C. for 10 minutes and samples were centrifuged. 23 μl of protein+sample buffer was loaded per well and gel was run at 150 volts for about an hour until the smallest standard reached the bottom of the gel. Gel proteins were transferred to PVDF membranes at 100 volts for 1 hour, rinsed with 1X TBST, and then blocked for 1 hour at room temperature on a rocker with 5% BSA in TBST. Rinsed membranes were incubated overnight with rabbit anti-2A peptide antibody (EMD Millipore ABS031) or anti-HA antibody (Cell Signaling, cat#3724) diluted in TBST+5% nonfat dry milk. Blots were incubated for 1 hour at room temperature with donkey anti-rabbit secondary antibody conjugated to horseradish peroxidase (BioRad, Hercules, Calif.). Blots were developed with enhanced chemiluminescence reagents (SuperSignal West Pico, ThermoFisher Scientific) and captured on a digital imaging system (Protein Simple, San Jose, Calif.). Western Blots on HEK 293 conditioned supernatants probed for Flt3L-OVA and Flt3L-NY-ESO-1 revealed that these fusion proteins were stable, secreted and had the predicted molecular weight.

XX. In Vitro Functional Assays

Frozen human PBMCs were purchased from ATCC (Manassas Va., cat.# PCS-800-011) thawed and pre-stimulated for 5 days in RPMI 1640 supplemented with 10% FBS, 1% P/S, 50 ng/mL recombinant human IL-2 and 10 ug/mL PHA-L. Cells ($2\times10^4$) were then seeded into triplicate wells of opaque white 96-well plates and cultured for 72 hours in growth media (RPMI 1640 containing 10% FBS and 1% P/S) with increasing amounts of Il-12p35/p40 heterodimer-containing HEK293 cell culture supernatant, protein concentration was determined via ELISA as described above. Supernatants from un-tranfected cells were used as negative controls. CellTiter-Glo (Promega, Madison Wis., cat.# G7570) was diluted to 1X as described by the manufacturer and 100 uL was pipetted into each well. The plates were gently shaken for 10 min at room temperature, then the luminescence was read on a SpectraMax plate reader (Molecular Devices, Sunnyvale, Calif.) with a 1 s integration time.

Culture supernatants from transfected HEK293 cells expressing and secreting IL-12 expression plasmids were added to the cells are proliferative responses were measured. The half-maximal response for PBMC proliferation was achieved with a 3-fold higher dilution factor for OMIP2A-hIL-12 as compared to OMIIRES-hIL-12 (69244 vs. 19548). When relative p70 protein concentrations were normalized, IL-12p70 expressed from the two vectors had comparable ability to stimulate cell proliferation in human PBMCs (FIG. 4B).

This result indicated that pOMI2A-IL-12 can generate 3 times more IL-12 mediated T cell proliferation from a given dose of plasmid.

Human CD8+ T cells were purchased fresh from AllCells (Alameda Calif., cat.# PB009-3), resuspended in RPMI 1640 containing 10% FBS and 1% P/S, and then seeded in triplicate wells of a black 96-well plate ($2\times10^4$ cells per well). Increasing amounts of IL15/IL15Ra-containing HEK293 cell culture supernatant (determined via ELISA as described above) were added and the cells were cultured for 3 days at 37° C., 5% CO2. CellTiter-Blue (Promega, Madison Wis., cat.# G8080) was then added to the wells followed by a 4 hr incubation at 37° C., The resulting fluorescence signal (Ex 560/Em 590 nm) was read on a Cytation 3 plate-reader (Biotek, Winooski Vt.).

Protein expressed from cells transfected with pOMI2A-IL-15/IL15Ra and pOMI2A-IL-15/IL15Ra-Fc both stimulated cell proliferation in human primary CD8+ T cells (FIG. 5B).

Tissue culture supernatants from cells expressing pOMIP2A-IL12-Flt3L-NY-ESO-1 were tested for the expression of functional IL-12 p70 using HEK-Blue cells. These cells are engineered to express human IL-12 receptors, and a STAT4-driven secreted form of alkaline phosphatase.

This reporter assay was performed according to the manufacturer protocol (HEK-Blue IL-12 cells, InvivoGen catalog #hkb-il12). Expression of secreted alkaline phosphatase (SEAP) was measured according to the manufacturer's protocol (Quanti-Blue, InvivoGen catalog # rep-qbl).

Figure 6:
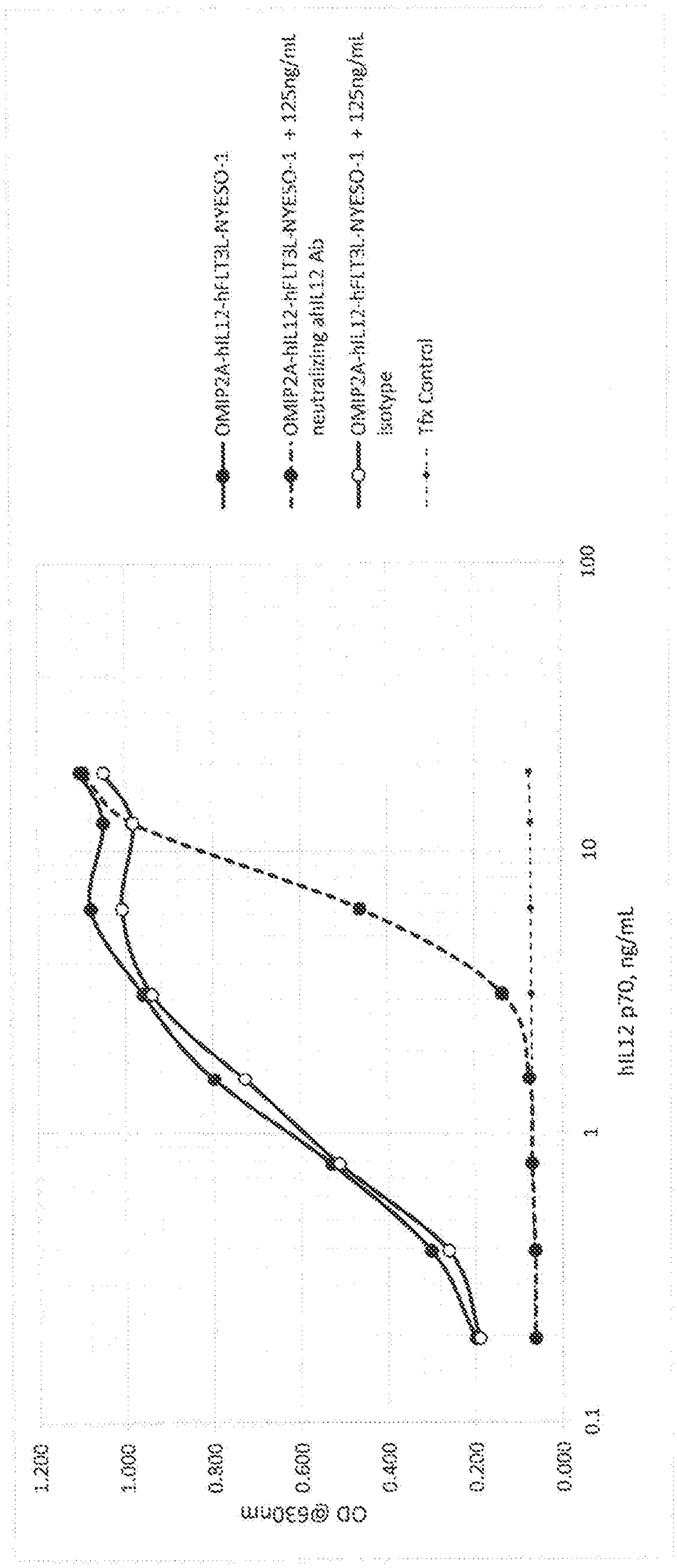
FIG. 6 illustrates the activity tissue culture cell conditioned media containing secreted IL-12 p70 heterodimers expressed from OMIP2A-IL12-Flt3L-NYESO1 vectors as measured using HEK Blue reporter cells. Controls (Addition of neutralizing anti-IL12 antibodies; conditioned media from un-transfected cells) and shown with dotted lines.

IL-1 p70 protein expressed and secreted from the OMIP2A polycistronic vector demonstrated strong activity in the induction of SEAP protein (FIG. 6). This activity was comparable to rhIL-12 protein controls, and was blocked by a neutralizing IL-12 antibody (R&D systems; AB-219-NA) (FIG. 6).

Human Flt3L and Flt3L-NY-ESO-1 fusion protein expressed from pOMIP2A vectors and secreted into the culture medium of HEK 293 cells were tested for binding to FLT3 receptors expressed on the surface THP-1 monocytic cells.

HEK cells were transfected with pOMIP2A-hFlt3L or pOMIP2A-hFlt3L-NYESO-1 (80-180aa) using Mirus TransIT LT-1. Supernatants were collected after 72 hours. The amount of secreted FLT3L proteins was quantified using hFlt3L ELISA (R&D Systems cat. # DY308).

The THP-1 monocyte cell line was cultured in RPMI+10% FBS+1% P/S (ATCC, cat. #TIB-202). For each experiment, 750,000 THP-1 cells were washed in Fc buffer (PBS+5% filtered FBS+0.1% NaN3), preincubated with human Fc block (TruStain FcX, Biolegend 422301) for 10 minutes and then incubated with 150 ng of recombinant hFlt3L-Fc (R&D Systems, cat.# AAA17999.1) or HEK 293 conditioned media containing 150 ng hFlt3L or hFlt3L-NYESO-1 protein and incubated for 1 hour at 4° C. Cells were then washed in Fc buffer and incubated with biotinylated anti-hFlt3L antibodies (R&D Systems, cat. #BAF308) for 1 hour. Cells were then washed in Fc buffer and incubated with streptactin-AlexaFluor-647 2° Ab for 1 hr (ThermoFisher, #S32357). Cell were washed again and analyzed by flow cytometry using a Guava 12HT cytometer (Millipore) on the Red-R channel. HEK 293 cells which do not express Flt3 receptors were also tested as a negative control.

TABLE 8

Secreted recombinant Flt3 ligand proteins bind to Flt3 receptors of the surface of THP-1 monocytes

| | Mean fluorescence intensity | | | |
|---|---|---|---|---|
| Cell line | unstained | Control super | hFlt3L | h-Flt3L-NYESO1 |
| THP-1 | 9.0 | 9.7 | 32.2 | 52.2 |
| HEK293 | 9.0 | 7.5 | 8.4 | 8.8 |

Over 90% of THP-1 cells showed an increase in mean fluorescence intensity with both hFlt3L and hFLT3L-NY-ESO-1 fusion proteins expressed from pOMIP2A vectors indicating that these recombinant proteins bind efficiently to Flt3 receptors on the cell surface.

In order to further test the functionality of the recombinant Flt3L proteins, HEK 293 conditioned media were used to test for induction of dendritic cell maturation in mouse splenocytes.

Spleens were excised from a B16-F10 tumor bearing C58/BL6 mice. Under sterile conditions, spleens were placed in DMEM media into the 70 micron cell strainer (Miltenyi) and mechanically dissociated using the rubber tip of the plunger from a 3 ml syringe. Once the spleen is completely dissociated, 10 mls of HBSS with 10% FBS (PFB) wad used to wash the strainer. Flow-though was spun in a centrifuge at 300×g for 10 mins. to pellet cells. Cells were washed once with PFB. Red blood cells were lysed with ACK lysis buffer according to the manufacturer's instructions (Thermo Fisher A1049201). Cells were filtered through a 40-micron cell strainer into a 15 ml conical tube and spun in a centrifuge at 300×g. Single cell suspension from the spleens were resuspended in complete RPMI-10 media. 1.5 million splenocytes were plated in a 12 well plate and allowed to adhere to the plate approximately 3 hrs. Non-adherent cells were removed and 2 mls of complete RPMI-10 media containing murine GMCSF (100 ng/ml) and murine IL4 (50 ng/ml) were added. The media was changed every 2 days for a week. The adherent dendritic cells were treated in triplicate wells with 1 ml of HEK 293 conditioned supernatants (containing 100 ng/ml Flt3L-NY-ESO-1 fusion protein) for 7 days. 100ng Recombinant Human Flt-3 Ligand Protein was compared as a positive control (R&D systems, AAA17999.1). Cells were gently scraped from a plate and the number of CD11c+ cells was determined by flow cytometric analysis.

When the number of CD3(−)CD11c(+) dendritic cells was tabulated, conditioned media from cells transfected with pOMIP2A-Flt3L-NYESO1 plasmid generated a significant increase in the number of these cells as compared to splenocytes incubated with conditioned media from un-transfected cells.

This result indicated that the FLT3L-NY-ESO-1 fusion protein can function to stimulate Flt3 receptor mediated dendritic cell maturation ex-vivo in mouse splenocytes.

XXI. Tumors and Mice

Female C57Bl/6J or Balb/c mice, 6-8 weeks of age were obtained from Jackson Laboratories and housed in accordance with AALAM guidelines.

B16.F10 cells were cultured with McCoy's 5A medium (2 mM L-Glutamine) supplemented with 10% FBS and 50 ug/ml gentamicin. Cells were harvested by trypsinizing with 0.25% trypsin and resuspended in Hank's balanced salt solution (HBSS). Anesthetized mice were subcutaneously injected with 1 million cells in a total volume of 0.1 ml into the right flank of each mouse. 0.5 million cells in a total volume of 0.1 ml were injected subcutaneously into the left flank of each mouse. Tumor growth was monitored by digital caliper measurements starting day 8 until average tumor volume reaches ~100 $mm^3$. Once tumors are staged to the desired volume, mice with very large or small tumors were culled. Remaining mice were divided into groups of 10 mice each, randomized by tumor volume implanted on right flank.

Additional tumor cell types were tested including B16OVA in C57Bl/6J mice as well as CT26 and 4T1 in Balb/c mice.

This protocol was used as a standard model to test simultaneously for the effect on the treated tumor (primary) and untreated (contralateral). Lung metastases were also quantified in Balb/c mice bearing 4T1 tumors.

XXII. Intratumoral Treatment

Mice were anesthetized with isoflurane for treatment. Circular plasmid DNA was diluted to 1 ug/ul in sterile 0.9% saline. 50 ul of plasmid DNA was injected centrally into primary tumors using a 1 ml syringe with a 26 Ga needle. Electroporation was performed immediately after injection. Electroporation of DNA was achieved using a Medpulser with clinical electroporation parameters of 1500 V/cm, 100 μs pulses, 0.5 cm, 6 needle electrode. Alternative parameters used were 400 V/cm, 10-msec pulses, using either a BTX generator or a generator incorporating impedence spectroscopy, as described above. Tumor volumes were measured twice weekly. Mice were euthanized when the total tumor burden of the primary and contralateral reached 2000 $mm^3$.

XXIII. Intratumoral Expression

One, 2 or 7 days after IT-EP (350 v/cm, 8 10-msec pulses), tumor tissue was isolated from sacrificed mice at various time point to determine expression of the transgenes. Tumor were dissected from mice and transferred to a cryotube in liquid nitrogen. The frozen tumor was transferred to a 4 ml tube containing 300 ul of tumor lysis buffer (50 mM TRIS pH 7.5, 150 mM NaCl, 1 mM EDTA, 0.5% Triton X-100, Protease inhibitor cocktail) and placed on ice and homogenized for 30 seconds (LabGen 710 homogenizer). Lysates were transferred to 1.5 ml centrifuge tube and spun at 10,000×g for 10 minutes at 4'C. Supernatants were to a new tube. Spin and transfer procedure was repeated three times. Tumor extracts were analyzed immediately according to manufacturer's instruction (Mouse Cytokine/Chemokine Magnetic Bead Panel MCYTOMAG-70K, Millepore) or frozen at −80'C. Recombinant Flt3L-OVA were done by standard ELISA protocols (R&D systems) using anti-Flt3L antibody for capture (R&D Systems, Minneapolis Minn. cat.# DY308) and the following antibodies for detection (ThermoFisher, cat.# PA1-196).

TABLE 9

Intratumoral expression of cytokines after electroporation of a polycistronic plasmid encoding hIL-12, hIL-15/hIL-15Rα and hIFNγ.

| Recombinant protein | Untreated [Protein] pg/mg Mean +/− SEM n = 2 | | | EP/pOMI-hIL12/hIL15/hINFγ [Protein] pg/mg Mean +/− SEM n = 3 | | |
|---|---|---|---|---|---|---|
| detected | Day 1 | Day 2 | Day 7 | Day 1 | Day 2 | Day 7 |
| IL-12 p70 | 0 | 0 | 0 | 3000.5 +/− 1872.7 | 2874.7 +/− 1459.1 | 19.1 +/− 4.2 |
| IL-15/IL-15Rα | 0 | 0 | 0 | 1.19 +/− 0.22 | 0.41 +/− 0.29 | 0.09 +/− 0.05 |
| INFγ | 0 | 0 | 0 | 36.6 +/− 6.4 | 45.0 +/− 12.8 | 1.0 +/− 0.4 |

To test for expression and function of our Flt3L-tracking antigen-fusion protein, we constructed a fusion of mouse Flt3L (extracellular domain) and peptides from the ovalbumin gene (Seq ID 25) in OMI2A vectors and electroporated intratumorally as above.

TABLE 10

Intratumoral expression of Flt3L-OVA fusion protein (genetic adjuvant with shared tumor antigen) 2 days after electroporation as analyzed by ELISA (n = 8).

| Recombinant protein construct | EP/pUMVC3 control Mean +/− SEM pg/ml | EP/recombinant protein construct Mean +/− SEM pg/ml |
|---|---|---|
| Flt3L-OVA fusion | 30.6 +/− 1.4 | 441 − 102 |

After intratumoral electroporation of pOMI2A vectors containing mouse homologs of the various immunomodulatory proteins, significant levels of IL-12p70, IL-15/IL-15Rα, INFγ (Table 9), and Flt3L-OVA recombinant proteins (Table x10) were all detectable in tumor homogenates by ELISA.

XXIV. Tumor Regression

TABLE 11

B16F0 tumor regression for treated and untreated tumors after intratumoral electroporation (IT-EP) of OMI vectors encoding mouse IL-12. Electroporation with the parameters of 1500 V/cm, 100 μs, 0.5 cm, 6 needle electrode was performed 8, 12, and 15 days after implantation. Tumor volume measurements shown were taken 16 days after implantation.

| | Tumor volume ($mm^3$), Mean +/− SEM, n = 10 | |
|---|---|---|
| Treatment | Treated tumor | Untreated tumor |
| Untreated | 1005.2 +/− 107.4 | 626.6 +/− 71.8 |
| EP/pUMVC3 control | 345.2 +/− 130.5 | 951.1 +/− 77.0 |
| EP/pOMIIRES-mIL-12 | 140.3 +/− 49.8 | 441.0 +/− 80.8 |
| EP/pOMI2A-mIL-12 | 92.1 +/− 38.7 | 283.3 +/− 87.2 |

Comparison of tumor regression after electroporation of pOMI2A-IL-12 vs. pOMIIRES-IL-12 demonstrated that using P2A exon skipping motif for expression of p35 and p40 subunits not only gave higher p70 IL-12 expression (FIG. 4A), but also better efficacy for tumor regression in vivo.

TABLE 12

B16F10 tumor regression for treated and untreated tumors after IT-EP with different doses of OMIP2A-IL-12. Electroporation with the parameters of 350 V/cm, 8 10-msec pulses using acupuncture needles was performed once, 8 days after implantation.

| | Tumor volume ($mm^3$), Mean +/− SEM, n = 10 | |
|---|---|---|
| Plasmid dose introduced by IT-EP | Treated tumor | Untreated tumor |
| pUMVC3 control 50 ug | 556.4 +/− 59.0 | 211.3 +/− 46.5 |
| pOMI2A-mIL-12 1 ug | 546.1 +/− 92.5 | 158.4 +/− 47.1 |
| pOMI2A-mIL-12 10 ug | 398.6 +/− 78.4 | 79.7 +/− 18.7 |
| pOMI2A-mIL-12 50 ug | 373.6 +/− 46.3 | 74.3 +/− 12.1 |

The extent of regression of both treated and untreated tumors increased with electroporation of increasing dose of OMIP2A-mIL-12 plasmid.

The ability of IT-EP of pOMIP2A-mIL12 to affect 4T1 primary tumor growth and lung metastases in Balb/c mice was also tested.

One million 4T1 cells were injected subcutaneously on the right flank of the mice and 0.25 million 4T1 cells were injected into the left flank. Larger tumors on the right flank were subject to IT-EP with empty vector (pUMVC3, Aldeveron) or with pOMIP2A-mIL12. Tumor volumes were measured every two days and on Day 19, mice were sacrificed, and the lungs were excised and weighed.

TABLE 13

Primary tumor growth and post-mortem weight of lungs of mice electroporated with 350 V/cm, 8 10-msec pulses with acupuncture needles on day 8, and day 15 post-implantation. Primary tumor volumes were measured on Day 17, and lung weights on Day 18.

| Treatment | Primary tumor volume (mm$^3$) Mean +/− SEM, n = 5 | Lung weight (grams) Mean +/− SEM, n = 5 |
| --- | --- | --- |
| Untreated | 897 +/− 131 | 0.252 +/− 0.019 |
| EP/pUMVC3 | 593 +/− 27 | 0.228 +/− 0.006 |
| EP/pOMIP2A-mIL12 | 356 +/− 80 | 0.184 +/− 0.004 |

It has been previously reported that systemic IL-12 treatment can reduce lung metastases in mice with 4T1 tumors (Shi et al., J Immunol. 2004, 172:4111). Our finding indicate that local IT-EP treatment of the tumors also reduced metastasis of these tumor cells to the lung in this model.

In addition to B16F10 tumors, electroporation of pOMIP2A-mIL12 also resulting in regression of both primary (treated) and contralateral (untreated) B16OVA and CT26 tumors. In the 4T1 tumor model, the primary tumor regressed after EP/pOMI-mIL12, and the mice demonstrated a significant reduction in lung weight, indicating a reduction in lung metastases. We show that IT-EP of OMIP2A-mIL12 can reduce tumor burden in 4 different tumor models in two different strains of mice.

TABLE 14

B16F10 tumor regression for treated and untreated tumors after intratumoral electroporation of pOMI2A plasmids containing genes encoding mIL-12 and Flt3L-OVA using 350 V/cm, and 8 10-msec pulses on day 7 and 14 after tumor cell inoculation; tumors measurements shown from Day 16.

| | Tumor volume (mm$^3$), Mean +/− SEM, n = 10 | |
| --- | --- | --- |
| Treatment | Treated tumor | Untreated tumor |
| EP/pUMVC3 control | 600.7 +/− 113.3 | 383.4 +/− 75.9 |
| EP/OMI2A_IL12/ OMI2A_Flt3LOVA | 94.2 +/− 31.7 | 115.7 +/− 42.3 |

TABLE 15

B16F10 tumor regression for treated tumors after IT-EP of pOMIP2A-mIL12-Flt3L-NYESO1 using 350 V/cm, and 8 10-msec pulses on day 7 after tumor cell inoculation; tumors measurements shown from Day 14.

| Treatment | Tumor volume (mm$^3$), Mean +/− SEM, n= |
| --- | --- |
| Untreated | 230.0 +/− 67.5 |
| EP/pUMVC3 empty vector | 170.8 +/− 20.8 |
| EP/pOMIP2A-mIL12-Flt3L-NYESO1 | 4.0 +/− 0.0 |

Electroporation of plasmid expressing both mouse IL-12 p70 and human Flt3L-NY-ESO-1 fusion protein caused complete regression of the treated tumor in 7 days.

The volume of both primary and contralateral tumors is significantly reduced in mice where immunomodulatory genes were introduced by electroporation as compared with electroporation of empty vector control, indicating not only a local effect within the treated tumor microenvironment, but an increase in systemic immunity as well.

XXIV. Flow Cytometry

At various time points after IT-pIL12-EP treatment, mice were sacrificed and tumor and spleen tissue were surgically removed.

Splenocytes were isolated by pressing spleens through a 70 micron filter, followed by red blood cell lysis (RBC lysis buffer, VWR, 420301OBL), and lympholyte (Cedarlane CL5035) fractionation. Lymphocytes were stained with SIINFEKL-tetramers (MBL International T03002), followed by staining with antibody cocktails containing: anti-CD3 (Biolegend 100225), anti-CD4 (Biolegend 100451), anti-CD8a (Biolegend 100742), anti-CD19 (Biolegend 115546), and vital stain (live-dead Aqua; Thermo-Fisher L-34966). Cells were fixed and analyzed on an LSR II flow cytometer (Beckman).

Tumors were dissociated using Gentle-MACS for tumors (Miltenyi tumor dissociation kit 130-096-730, C-tubes, 130-093-237) and homogenized using an Miltenyi gentleMACS™ Octo Dissociator with Heaters (130-096-427). Cells were pelleted at 800×g for 5 min at 4'C and re-suspended in 5 mL of PBS+2% FBS+1 mM EDTA (PFB) and overlaid onto 5 mL of Lympholyte-M (Cedarlane). Lympholyte columns were spun in centrifuge at 1500×g for 20 min at room temperature with no brake. Lymphocyte layer was washed with PBF. Cell pellets were gently re-suspended in 500 uL of PFB with Fc block (BD Biosciences 553142). In 96-well plate, cells were mixed with a solution of SIINFEKL teramer (MBL), representing the immunodominant antigen in B16OVA tumors, according to the manufacturers instruction and incubated for 10 minutes at room temperature. Antibody staining cocktails containing the following: Anti-CD45-AF488 (Biolegend 100723), anti-CD3-BV785 (Biolegend 100232), Anti-CD4-PE (eBioscience12-0041), anti-CD8a-APC (eBioscience 17-0081), anti-CD44-APC-Cy7 (Biolegend 103028), anti-CD19-BV711 (Biolegend 11555), anti-CD127 (135010), anti-KLRG1 (138419), were added and incubated at room temperature for 30 minutes. Cells were washed 3 times with PFB. Cells were fixed in PFB with 1% paraformaldehyde for 1 minutes on ice. Cells were washed twice with PFB and stored at 4'C in the dark. Samples were analyzed on an LSR II flow cytometer (Beckman).

TABLE 16

IT-pIL12-EP increased SIINFEKL-tetramer-binding CD8+ T cells in the spleens of treated, B16OVA tumor-bearing mice. Mice were electroporated intratumorally (IT-EP) once on Day 0 using 350 V/cm, 10-msec pulses, 300 ms pulse frequency, with 0.5 cm acupuncture needles.

| Treatment | Percent of CD3$^+$CD8$^+$CD44$^+$ T cells that are SIINFEKL-tetramer positive on Day 13, n = 6 |
| --- | --- |
| IT-pIL12-EP | 2.36 +/− 0.75 |
| IT-pUMVC3-EP | 0.24 +/− 0.04 |
| untreated | 0.10 +/− 0.04 |

IT-pIL12-EP induces an increase in circulating CD8$^+$ T cells directed against the SIINFEKL peptide from ovalbumin, the dominant antigen in B16OVA tumors. These data indicate that local IL-12 therapy can lead to system tumor immunity in mice.

TABLE 17

Intratumoral electroporation of pIL12 alters the immune environment in B16OVA contralateral tumors. Mice were electroporated intratumorally (IT-EP) once on Day 0 using 350 V/cm, 10-msec pulses, 300 ms pulse frequency, with 0.5 cm acupuncture needles. The composition of infiltrating lymphocytes (TIL) in untreated tumors measured 18 days after treatment is shown.

| | Composition of TIL in untreated tumors Mean +/− SEM, n = 6 | | |
|---|---|---|---|
| Treatment | % $CD3^+CD8^+$ T cells | % SLEC T cells | $CD8^+/T_{reg}$ T cell ratio |
| IT-pIL12-EP | 14.8 +/− 2.7 | 1.0 +/− 0.1 | 1892 +/− 602 |
| IT-pUMVC3-EP | 3.6 +/− 1.1 | 0.2 +/− 0.07 | 659 +/− 129 |
| Untreated | 2.9 +/− 0.9 | 0.09 +/− 0.03 | 753 +/− 288 |

Electroporation of OMI2A-pIL-12 into the primary tumor can significantly alter the composition of TILs within the contralateral, untreated tumor. These results show that intratumoral treatment with pOMI2A-IL-12 can affect the immune environment in untreated tumors indicating that local treatment leads to a systemic anti-tumor immune response. This conclusion is corroborated by increased detection of tumor antigen-specific $CD8^+$ T cells in the spleen (Table 16), contralateral tumor regression (Table 12), and reduction in lung metastases (Table 13).

XXV. Analysis of Mouse Gene Expression

NanoString was used for analysis of changes in gene expression in treated and untreated tumors induced by IT-EP of pOMIP2A-IL12 and pOMI-Flt3L-NYESO1 plasmids. Tumor tissue was carefully harvested from mice using scalpel and flash frozen in liquid nitrogen. Tissues were weighed using a balance (Mettler Toledo, Model ML54). 1 ml of Trizol (Thermo Fisher Scientific, Waltham, Mass.) was added to the tissue and homogenized using a probe homogenizer on ice. RNA was extracted from Trizol using manufacturer's instructions. Contaminating DNA was removed by Dnase (Thermo Fisher, Cat no: EN0525) treatment. Total RNA concentrations were determined using the NanoDrop ND-1000 spectrophotometer (Thermo Fisher Scientific). Gene expression profiling was performed using NanoString technology. In brief, 50 ng of Total RNA was hybridized at 96° C. overnight with the nCounter® (Mouse immune 'v1' Expression Panel NanoString® Technologies). This panel profiles 561 immunology-related mouse gene as well as two types of built-in controls: positive controls (spiked RNA at various concentrations to evaluate the overall assay performance) and 15 negative controls (to normalize for differences in total RNA input). Hybridized samples were then digitally analyzed for frequency of each RNA species using the nCounter SPRINT™ profiler. Raw mRNA abundance frequencies were analyzed using the nSolver™ analysis software 2.5 pack. In this process, normalization factors derived from the geometric mean of housekeeping genes, mean of negative controls and geometric mean of positive controls were used.

TABLE 18

IT-EP of pOMIP2A-IL12 caused an increase in intratumoral levels of lymphocyte and monocyte cell surface markers in both primary and contralateral tumors. Fold change of treated vs. untreated mice values are shown

| Immune Checkpoint | IT-pIL12-EP Mean +/− SEM n = 5 | | IT-pUMVC3-EP Mean +/− SEM n = 4 | | Untreated Mean +/− SEM n = 3 | |
|---|---|---|---|---|---|---|
| Protein RNA | Primary | Contralateral | Primary | Contralateral | Primary | Contralateral |
| CD45 | 11.54 +/− 1.65 | 3.55 +/− 0.40 | 1.70 +/− 0.72 | 1.26 +/− 0.51 | 1.00 +/− 0.38 | 1.00 +/− 0.50 |
| CD3 | 13.16 +/− 2.95 | 5.30 +/− 0.72 | 1.26 +/− 0.38 | 1.09 +/− 0.32 | 1.00 +/− 0.22 | 1.00 +/− 0.40 |
| CD4 | 2.35 +/− 0.39 | 2.74 +/− 0.44 | 0.73 +/− 0.18 | 1.00 +/− 0.22 | 1.00 +/− 0.20 | 1.00 +/− 0.09 |
| CD8 | 16.28 +/− 3.10 | 4.60 +/− 0.50 | 1.23 +/− 0.32 | 1.00 +/− 0.15 | 1.00 +/− 0.14 | 1.00 +/− 0.45 |
| KLRC1 | 14.03 +/− 2.73 | 5.62 +/− 0.23 | 1.16 +/− 0.45 | 1.28 +/− 0.44 | 1.00 +/− 0.07 | 1.00 +/− 0.43 |
| KLRD1 | 4.64 +/− 1.00 | 4.17 +/− 0.33 | 1.05 +/− 0.27 | 1.65 +/− 0.45 | 1.00 +/− 0.20 | 1.00 +/− 0.30 |
| CD11b | 11.13 +/− 2.39 | 4.17 +/− 0.48 | 1.55 +/− 0.52 | 1.11 +/− 0.40 | 1.00 +/− 0.42 | 1.00 +/− 0.34 |

TABLE 19

IT-EP of pOMIP2A-IL12 caused an increase in intratumoral levels of INF-γ regulated genes in both primary and contralateral tumors. Fold change of treated vs. untreated mice values are shown.

| IFN-γ related | IT-pIL12-EP Mean +/− SEM n = 5 | | IT-pUMVC3-EP Mean +/− SEM n = 4 | | Untreated Mean +/− SEM n = 3 | |
|---|---|---|---|---|---|---|
| RNA | Primary | Contralateral | Primary | Contralateral | Primary | Contralateral |
| IFNγ | 8.63 +/− 1.38 | 1.80 +/− 0.44 | 0.76 +/− 0.22 | 0.98 +/− 0.43 | 1.00 +/− 0.15 | 1.00 +/− 0.29 |
| CD274 (PD-L1) | 12.47 +/− 2.24 | 7.03 +/− 2.30 | 1.00 +/− 0.30 | 1.18 +/− 0.83 | 1.00 +/− 0.48 | 1.00 +/− 0.84 |
| CXCL10 | 3.18 +/− 0.58 | 2.26 +/− 0.42 | 0.99 +/− 0.30 | 1.44 +/− 0.85 | 1.00 +/− 0.43 | 1.00 +/− 0.73 |
| CXCL11 | 5.02 +/− 0.74 | 3.14 +/− 0.41 | 0.74 +/− 0.10 | 1.38 +/− 0.82 | 1.00 +/− 0.16 | 1.00 +/− 0.55 |
| CXCL9 | 5.92 +/− 0.60 | 3.75 +/− 0.57 | 1.03 +/− 0.31 | 1.67 +/− 1.37 | 1.00 +/− 0.50 | 1.00 +/− 0.85 |
| H2A-a | 9.21 +/− 1.86 | 6.63 +/− 2.21 | 1.26 +/− 0.36 | 1.52 +/− 0.99 | 1.00 +/− 0.61 | 1.00 +/− 1.28 |
| H2k-1 | 4.23 +/− 1.02 | 3.71 +/− 0.68 | 1.06 +/− 0.19 | 1.42 +/− 0.52 | 1.00 +/− 0.54 | 1.00 +/− 0.87 |
| IRF 1 | 4.18 +/− 0.28 | 2.72 +/− 0.46 | 1.09 +/− 0.28 | 1.28 +/− 0.93 | 1.00 +/− 0.45 | 1.00 +/− 0.78 |

TABLE 19-continued

IT-EP of pOMIP2A-IL12 caused an increase in intratumoral levels of INF-γ regulated genes in both primary and contralateral tumors. Fold change of treated vs. untreated mice values are shown.

| IFN-γ related | IT-pIL12-EP Mean +/− SEM n = 5 | | IT-pUMVC3-EP Mean +/− SEM n = 4 | | Untreated Mean +/− SEM n = 3 | |
|---|---|---|---|---|---|---|
| RNA | Primary | Contralateral | Primary | Contralateral | Primary | Contralateral |
| PDCD1 (PD-1) | 3.80 +/− 0.48 | 2.78 +/− 0.84 | 1.13 +/− 0.25 | 1.18 +/− 0.37 | 1.00 +/− 0.28 | 1.00 +/− 0.56 |
| Stat 1 | 3.51 +/− 0.28 | 3.47 +/− 0.68 | 1.04 +/− 0.26 | 1.36 +/− 0.79 | 1.00 +/− 0.48 | 1.00 +/− 0.79 |
| TAP 1 | 3.80 +/− 0.48 | 2.84 +/− 0.37 | 1.17 +/− 0.27 | 1.36 +/− 0.85 | 1.00 +/− 0.50 | 1.00 +/− 0.97 |
| CCL5 | 24.47 +/− 7.81 | 14.59 +/− 2.97 | 2.21 +/− 0.72 | 1.48 +/− 0.40 | 1.00 +/− 0.29 | 1.00 +/− 0.40 |
| CCR5 | 11.29 +/− 2.72 | 3.70 +/− 0.70 | 1.31 +/− 0.42 | 1.21 +/− 0.42 | 1.00 +/− 0.27 | 1.00 +/− 0.40 |
| GZMA | 11.08 +/− 1.18 | 4.60 +/− 0.96 | 1.43 +/− 0.53 | 2.05 +/− 0.91 | 1.00 +/− 0.23 | 1.00 +/− 0.22 |
| GZMB | 3.11 +/− 0.83 | 2.11 +/− 0.10 | 0.68 +/− 0.22 | 1.47 +/− 0.67 | 1.00 +/− 0.33 | 1.00 +/− 0.47 |
| PRF1 | 8.21 +/− 2.27 | 2.06 +/− 0.26 | 1.0 +/− 0.32 | 1.13 +/− 0.45 | 1.00 +/− 0.23 | 1.00 +/− 0.39 |

Additional NanoString gene expression analysis of extracts from treated and untreated tumors in the 4T1 and MC-38 tumor models after pOMIP2A-IL12 electroporation revealed similar upregulation of lymphocyte and monocyte cell surfacemarkers as well as INFγ-regulated genes, indicating that these effects of IL-12 on the tumor microenvironment are generalizable to multiple mouse tumor models.

Gene expression analysis of tissue from treated and untreated tumors corroborate flow cytometric analysis showing a robust increase in tumor TIL with IT-EP of pOMIP2A-IL12. In addition, an increase in interferon gamma-regulated genes suggest induction of an immunostimulatory environment within the tumors. A significant increase in expression of checkpoint proteins indicate that IT-pIL12-EP could increase the substrate for the action of checkpoint inhibitors used in combination.

Intratumoral electroporation of an OMI plasmid encoding human Flt3L-NY-ESO-1 fusion protein alone also had effects on tumor regression and changes to the immune phenotype of tumor TIL.

TABLE 20

IT-EP of pOMI-Flt3L-NYESO1 plasmid reduced tumor growth. Subcutaneous 4T1 tumors were electroporated once at 350 V/cm, 8 10 msec pulses with acupuncture needles after plamdis injection. Tumor measurements on Day 6 after treatment are shown.

| Treatment | Tumor volume ($mm^3$) Mean +/− SEM n = 5 |
|---|---|
| Untreated | 273.8 +/− 35.7 |
| EP/pUMVC3 (empty vector) | 380.4 +/− 84.7 |
| EP/pOMI-Flt3L-NYESO1 | 127.1 +/− 13.2 |
| EP/pOMIP2A-IL12 | 69.4 +/− 16.4 |

TABLE 21

Changes INFγ related gene expression in treated tumors after IT-EP of pOMI-Flt3L-NYESO1 as measured by NanoString in tumor extracts. Fold change of treated vs. untreated mice values are shown.

| IFN-γ related RNA | IT-EP pUMVC3 Mean +/− SEM n = 3 | IT-EP pOMI-Flt3L-NYESO1 Mean +/− SEM n = 5 |
|---|---|---|
| Cxcl9 | 1.00 +/− 0.07 | 3.68 +/− 0.42 |
| Cxcl10 | 1.00 +/− 0.02 | 1.80 +/− 0.17 |
| Cxcl11 | 1.00 +/− 0.35 | 2.29 +/− 0.41 |
| Cd274 | 1.00 +/− 0.28 | 3.31 +/− 0.55 |

TABLE 21-continued

Changes INFγ related gene expression in treated tumors after IT-EP of pOMI-Flt3L-NYESO1 as measured by NanoString in tumor extracts. Fold change of treated vs. untreated mice values are shown.

| IFN-γ related RNA | IT-EP pUMVC3 Mean +/− SEM n = 3 | IT-EP pOMI-Flt3L-NYESO1 Mean +/− SEM n = 5 |
|---|---|---|
| Irf1 | 1.00 +/− 0.07 | 2.31 +/− 0.16 |
| Stat1 | 1.00 +/− 0.13 | 2.46 +/− 0.25 |

TABLE 22

Changes in antigen presentation machinery (APM) gene expression in treated tumors after IT-EP of pOMI-Flt3L-NYESO1 as measured by NanoString in tumor extracts. Fold change of treated vs. untreated mice values are shown.

| APM RNA | IT-EP pUMVC3 Mean +/− SEM n = 3 | IT-EP pOMI-Flt3L-NYESO1 Mean +/− SEM n = 5 |
|---|---|---|
| H2-Ob | 1.00 +/− 0.24 | 2.09 +/− 0.48 |
| H2-Aa | 1.00 +/− 0.29 | 4.41 +/− 0.78 |
| H2-K1 | 1.00 +/− 0.21 | 2.20 +/− 0.16 |
| H2-Ab1 | 1.00 +/− 0.22 | 4.78 +/− 0.82 |
| H2-Eb1 | 1.00 +/− 0.22 | 3.74 +/− 0.50 |
| Tap1 | 1.00 +/− 0.08 | 2.63 +/− 0.25 |
| Tapbp | 1.00 +/− 0.11 | 2.61 +/− 0.23 |
| Cd74 | 1.00 +/− 0.22 | 4.71 +/− 0.81 |
| Ccr7 | 1.00 +/− 0.09 | 2.08 +/− 0.33 |
| Cd11b | 1.00 +/− 0.18 | 2.22 +/− 0.27 |

TABLE 23

Changes in co-stimulatory gene expression in treated tumors after IT-EP of pOMI-Flt3L-NYESO1 as measured by NanoString in tumor extracts. Fold change of treated vs. untreated mice values are shown.

| Co-stimulatory RNA | IT-EP pUMVC3 Mean +/− SEM n = 3 | IT-EP pOMI-Flt3L-NYESO1 Mean +/− SEM n = 5 |
|---|---|---|
| Cd80 | 1.00 +/− 0.12 | 2.01 +/− 0.35 |
| Cd40 | 1.00 +/− 0.18 | 3.15 +/− 0.52 |
| Ctla4 | 1.00 +/− 0.06 | 3.11 +/− 0.47 |
| Cd274 | 1.00 +/− 0.28 | 3.31 +/− 0.55 |
| Icam1 | 1.00 +/− 0.33 | 2.67 +/− 0.55 |

TABLE 24

Changes in T cell and Natural Killer (NK) cell gene expression in treated tumors after IT-EP of pOMI-Flt3L-NYESO1 as measured by NanoString in tumor extracts. Fold change of treated vs. untreated mice values are shown.

| T and NK cell RNA | IT-EP pUMVC3 Mean +/− SEM n = 3 | IT-EP pOMI-Flt3L-NYESO1 Mean +/− SEM n = 5 |
|---|---|---|
| Klrc1 | 1.00 +/− 0.37 | 2.84 +/− 0.40 |
| Klrd1 | 1.00 +/− 0.11 | 3.91 +/− 0.74 |
| Cd3e | 1.00 +/− 0.38 | 3.57 +/− 0.70 |
| Cd8a | 1.00 +/− 0.36 | 2.03 +/− 0.38 |
| Cd4 | 1.00 +/− 0.10 | 2.08 +/− 0.36 |

In order to test for host response to electroporation of plasmids encoding a tracking antigen fused to Flt3L, B16F10 tumors were electroporated with pOMI-Flt3L-OVA and the host respose to the OVA antigen was measured. Mice were injected with 1 million B16F10 cells on the right flank. Seven days later, tumors were electroporated with pOMI-mIL12-mFlt3L-OVA, empty vector, or left untreated. Electroporation was done using the Genesis generator, 400 V/cm, 8 10-msec pulses. Tumors regression was observed with pOMI-mIL12-mFLT3-OVA (Table 15).

Detection of tracking antigen-specific CD8+ T cells in mouse was tested inguinal lymph nodes 7 days after introduction of plasmid encoding FLt3L-OVA fusion proteins into tumors.

Lymph nodes were isolated 7 days after electroporation treatment. Mice were sacrificed; inguinal lymph nodes were excised, mashed in PBS+2% FBS+1 mM EDTA (PFB) and then strained through a 70 micro filter. Cells were pelleted in a centrifuge at 300×g at 4'C and washed in PFB, and counted on a Cellometer (Nexcelom).

Lymph node cell pellets were gently re-suspended in PFB with Fc block (BD Biosciences 553142). Cells were then mixed with a solution of SIINFEKL tetramer (MBL), according to the manufacturers instruction and incubated for 10 minutes at room temperature. Antibody staining cocktails containing the following: Live/Dead Aqua (Thermo Fisher L34966), Anti-CD3 (Biolegend 100228), anti-CD19 (Biolegend 115555), anti-CD127 (Biolegend), anti-CD8a (MBL D271-4), anti-CD44 (Biolegend 103028), anti-PD-1 (Biolegend 109110), anti-CD4 (Biolegend 100547), anti-KLRG1 (138419), anti-CD62L (Biolegend 104448) were added and incubated at 4'C for 30 minutes. Cells were washed with PFB. Cells were fixed in PFB with 1% paraformaldehyte for 1 minute on ice. Cells were washed 3 times with PFB, and analyzed by flow cytometry (LSR Fortessa X-20).

TABLE 25

Detection of host immune cells displaying tracking antigen and T cells reactive to tracking antigen after IT-EP of pOMI-mIL12-hFlt3L-OVA as compared to pUMVC3 empty vector into B16F10 subcutaneous tumors.

| Plasmid introduced by IT-EP | Frequency of CD44 + SIINFEKLtetramer + CD8 T cells | Frequency of SIINFEKLtetramer + CD8 + T cells |
|---|---|---|
| Untreated n = 3 | 0.0003 +/− 0.0003 | 0.0067 +/− 0.0018 |
| pUMVC3 n = 4 | 0.0026 +/− 0.0003 | 0.0100 +/− 0.0027 |
| pOMI-mIL12-hFlt3L-OVA n = 6 | 0.4050 +/− 0.2457 | 0.2958 +/− 0.0582 |

Using OVA as a surrogate tracking antigen in mice, we demostrate that we can readily detect circulating T cells directed against the tracking antigen which was electroporated into tumor as a Flt3L-fusion protein.

XXV. Introduction of Plasmids by Hydrodynamic Injection into Mouse Tail Vein

The in vivo activity of Flt3L fusion proteins expressed from OMI plasmids was tested by hydrodynamic injection of 5 ugs of plasmids into the tail vein of C57Bl/6J mice. Seven days later, mice were sacrificed, the spleens were excised, weighed, and dissociated for analysis of changes in cell composition by flow cytometry.

Splenocytes were isolated as described above, washed with PFB and re-suspended in PFB with Fc block (BD Biosciences 553142) and incubated for 10 minutes at room temp. Antibody cocktails containing the following were added: Anti NK1.1 (Biolegend108731), Live/Dead Aqua ( ), anti-CD4 (Biolegend 100547), anti-F4/80 (Biolegend 123149), anti-CD19 (Biolegend 115555), Anti-I-A/I-E (Biolegend 107645), Anti-CD8 (MBL International D271-4), anti-CD80 (Biolegend 104722), anti-CD3 (Biolegend 117308), anti-CD40 (Biolegend 124630), anti-GR-1 (Biolegend 108424), anti-CD11c (Biolegend 117324), anti-CD86 (Biolegend 105024, anti-CD11b (Biolegend 101212). Incubate at 37'C. Cells were washed 3 times with PFB, and analyzed by flow cytometry (LSR Fortessa X-20).

TABLE 26

Effect of systemic exposure to pOMIP2A-FLt3L and pOMIP2A-Flt3LNYESO1 plasmids introduced by tail vein injection.

| Injected Plasmid | Spleen weight (grams) Mean +/− SEM, n = 6 | Absolute $CD11c^+$ cell number; Mean × $10^6$ +/− SEM, n = 6 | $CD11c^+$ frequency of parent $CD3^-$ $CD19^-NK1.1^-$; Mean percent +/− SEM, n = 6 |
|---|---|---|---|
| None | 0.085 +/− 0.005 | 1.82 | 7.68 +/− 0.66 |
| pUMVC3 empty vector | 0.090 +/− 0.006 | 2.75 | 12.11 +/− 0.08 |
| OMI-Flt3LNYESO1 | 0.123 +/− 0.009 | 5.26 | 31.75 +/− 2.88 |
| OMI-Flt3L | 0.141 +/− 0.011 | 5.42 | 37.60 +/− 3.22 |

Introduction of plasmids encoding human Flt3L or human FLt3L fused to a portion of the NY-ESO-1 proteins (80-180 aa) lead to an increase in CD11+ dendritic cells (DC) in the spleen. Moreover, the majority of these DC demosgtrated high levels of MHC Class II indicating that they are mature DCs. In addition, a portion of these DCs demonstrated higher levels of cell surface CD86, indicating they were activated.

These data are consistent with exposure to active Flt3 ligand being expressed from these plasmids and leading to DC maturation and activation in the mice (Maraskovsky et al., 2000. Blood 96:878)

SEQUENCE IDENTIFIERS

TABLE 27

Sequence Identifier Table

| SEQ ID NO | Description |
|---|---|
| 1 | Promoter/enhancer: Human CMV |
| 2 | Promoter/enhancer: Simian CMV |
| 3 | Promoter/enhancer: SV-40 |
| 4 | Promoter/enhancer: mPGK |
| 5 | Human IL-12p35-P2A-IL-12p40 (DNA) |
| 6 | Mouse IL-12p35-P2A-IL-12p40 (DNA) |
| 7 | Canine IL-12p35-P2A-IL-12p40 (DNA) |
| 8 | Human IL-15/IL-15Ra with P2A (DNA) |
| 9 | Human IL-15/IL-15Ra with P2A (protein) |
| 10 | Human IL-15/IL-15Ra-Fc with P2A (DNA) |
| 11 | Human IL-15/IL-15Ra-Fc with P2A (protein) |
| 12 | Human interferon gamma (DNA) |
| 13 | Flt3L- NY-ESO-1 (full length) fusion protein (DNA) |
| 14 | Flt3L- NY-ESO-1 (full length) fusion protein (protein) |
| 15 | Flt3L- NY-ESO-1 (amino acids 80-180) fusion protein (DNA) |
| 16 | Flt3L- NY-ESO-1 (amino acids 80-180) fusion protein (protein) |
| 17 | Flt3L- NY-ESO-1 (fusion of peptides) fusion protein (DNA) |
| 18 | Flt3L- NY-ESO-1 (fusion of peptides) fusion protein (protein) |
| 19 | Translation Modulator, exon-skipping motif P2A |
| 20 | Translation Modulator, exon-skipping motif T2A |
| 21 | Translation Modulator, exon-skipping motif E2A |
| 22 | Translation Modulator, exon-skipping motif F2A |
| 23 | Translation modifier: Internal Ribosomal Entry Site (IRES) |
| 24 | Ovalbumin aa 241-270 (DNA) |
| 25 | Ovalbumin aa 241-270 (protein) |

What is claimed is:

1. An expression plasmid comprising an expression cassette represented by the formula:

P-A-T-B wherein:

a) P is an expression promoter;

b) A encodes an immunostimulatory cytokine;

c) B encodes a genetic adjuvant fused to at least one antigen, wherein the genetic adjuvant fused to the at least one antigen comprises the amino acid sequence of: SEQ ID NO: 14, SEQ ID NO: 16, or SEQ ID NO: 18; and d) T is a translation modification element.

2. The expression plasmid of claim 1, wherein P is selected from the group consisting of: a human CMV promoter, a simian CMV promoter, a SV-40 promoter, a mPGK promoter, and a β-Actin promoter.

3. The expression plasmid of claim 1, wherein the immunostimulatory cytokine is selected from the group consisting of: IL-12, IL-15, IL-23, and IL 27.

4. An expression plasmid comprising an expression cassette represented by the formula:

P-A-T-A'-T-B or P-B-T-A-T-A' wherein:

a) P is an expression promoter;

b) A and A' encode subunits of a heterodimeric cytokine;

c) B encodes at least one genetic adjuvant fused to at least one antigen wherein the at least one genetic adjuvant fused to the at least one antigen comprises the amino acid sequence of: SEQ ID NO: 14, SEQ ID NO: 16, or SEQ ID NO: 18; and d) T is a translation modification element.

5. The expression plasmid of claim 4 wherein P is selected from the group consisting of a human CMV promoter, a simian CMV promoter, SV-40 promoter, a mPGK, and a β-Actin promoter.

6. The expression plasmid of claim 4, wherein the heterodimeric cytokine is selected from the group consisting of IL-12, IL-15, IL-23, and IL-27.

7. The expression plasmid of claim 4, wherein:

a) A encodes IL-12p35, IL-23p19, EBI3, or IL-15; and b) A' encodes IL-12p40, IL-27p28, or IL-15Rα.

8. The expression plasmid of claim 4, wherein the translation modification element is selected from the group consisting of: a 2A family member and an internal ribosomal entry site (IRES).

9. The expression plasmid of claim 4, wherein A encodes IL-12p35 and A' encodes IL-12p40.

10. The expression plasmid of claim 4, wherein the antigen is a NYESO-1 antigen.

11. A method of treating a tumor in a subject comprising, delivering the expression plasmid of claim 4 into the tumor using at least one intratumoral electroporation pulse, wherein the tumor is selected from the group of melanoma, triple negative breast cancer, Merkel Cell Carcinoma, CTCL, and head and neck squamous cell carcinoma.

12. The method of claim 11, wherein the intratumoral electroporation pulse has a field strength of about 200 V/cm to 1500 V/cm.

13. The method of claim 11, wherein the subject is a human.

14. The method of claim 11, wherein the electroporation pulse is delivered by a generator capable of electrochemical impedance spectroscopy.

* * * * *

SEQUENCE LISTING

```
<160> NUMBER OF SEQ ID NOS: 25

<210> SEQ ID NO 1
<211> LENGTH: 576
<212> TYPE: DNA
<213> ORGANISM: Artificial Sequence
<220> FEATURE:
<223> OTHER INFORMATION: Human CMV promoter/enhancer

<400> SEQUENCE: 1

tagtaatcaa ttacggggtc attagttcat agcccatata tggagttccg cgttacataa      60

cttacggtaa atggcccgcc tggctgaccg cccaacgacc cccgcccatt gacgtcaata     120

atgacgtatg ttcccatagt aacgccaata gggactttcc attgacgtca atgggtggag     180

tatttacggt aaactgccca cttggcagta catcaagtgt atcatatgcc aagtacgccc     240

cctattgacg tcaatgacgg taaatggccc gcctggcatt atgcccagta catgacctta     300

tgggactttc ctacttggca gtacatctac gtattagtca tcgctattac catggtgatg     360

cggttttggc agtacatcaa tgggcgtgga tagcggtttg actcacgggg atttccaagt     420

ctccacccca ttgacgtcaa tgggagtttg ttttggcacc aaaatcaacg ggactttcca     480
```

-continued aaatgtcgta acaactccgc cccattgacg caaatgggcg gtaggcgtgt acggtgggag 540
gtctatataa gcagagctcg tttagtgaac cgtcag 576

<210> SEQ ID NO 2
<211> LENGTH: 593
<212> TYPE: DNA
<213> ORGANISM: Artificial Sequence
<220> FEATURE:
<223> OTHER INFORMATION: Simian CMV promoter/enhancer

<400> SEQUENCE: 2
atagtattcc atatatgggt tttcctattg acgtagatag cccctcccaa tgggcggtcc 60
catataccat atatggggct tcctaatacc gcccatagcc actcccccat tgacgtcaat 120
ggtctctata tatggtcttt ttcgaaccta ttgacgtcat atgggcggtc ctattgacgt 180
atatggcgcc tcccccattg acgtcaatta cggtaaatgg cccgcctggc tcaatgccca 240
ttgacgtcaa taggaccacc caccattgac gtcaatggga tggctcattg cccattcata 300
tccgttctca cgcccccctat tgacgtcaat gacggtaaat ggcccacttg gcagtacatc 360
aatatctatt aatagtaact tggcaagtac attactattg gaagtacgcc agggtacatt 420
ggcagtactc ccattgacgt caatggcggt aaatggcccg cgatggctgc caagtacatc 480
cccattgacg tcaatgggga ggggcaatga cgcaaatggg cgttccattg acgtaaatgg 540
gcggtaggcg tgcctaatgg gaggtctata taagcaatgc tcgtttaggg aac 593

<210> SEQ ID NO 3
<211> LENGTH: 511
<212> TYPE: DNA
<213> ORGANISM: Mus musculus

<400> SEQUENCE: 3
ttctaccggg taggggaggc gcttttccca aggcagtctg gagcatgcgc tttagcagcc 60
ccgctgggca cttggcgcta cacaagtggc ctctggcctc gcacacattc cacatccacc 120
ggtaggcgcc aaccggctcc gttctttggt ggccccttcg cgccaccttc tactcctccc 180
ctagtcagga agttcccccc cgccccgcag ctcgcgtcgt gcaggacgtg acaaatggaa 240
gtagcacgtc tcactagtct cgtgcagatg gacagcaccg ctgagcaatg gaagcgggta 300
ggcctttggg gcagcggcca atagcagctt tgctccttcg ctttctgggc tcagaggctg 360
ggaaggggtg ggtccggggg cgggctcagg ggcgggctca ggggcggggc gggcgcccga 420
aggtcctccg gaggcccggc attctgcacg cttcaaaagc gcacgtctgc cgcgctgttc 480
tcctcttcct catctccggg cctttcgacc t 511

<210> SEQ ID NO 4
<211> LENGTH: 344
<212> TYPE: DNA
<213> ORGANISM: Artificial Sequence
<220> FEATURE:
<223> OTHER INFORMATION: SV-40 promoter

<400> SEQUENCE: 4
ctgtggaatg tgtgtcagtt agggtgtgga aagtccccag gctccccagc aggcagaagt 60
atgcaaagca tgcatctcaa ttagtcagca accaggtgtg gaaagtcccc aggctcccca 120
gcaggcagaa gtatgcaaag catgcatctc aattagtcag caaccatagt cccgccccta 180
actccgccca tcccgcccct aactccgccc agttccgccc attctccgcc ccatggctga 240
ctaatttttt ttatttatgc agaggccgag gccgcctctg cctctgagct attccagaag 300
tagtgaggag gctttttgg aggcctaggc ttttgcaaaa agct 344

<210> SEQ ID NO 5
<211> LENGTH: 1824
<212> TYPE: DNA
<213> ORGANISM: Artificial Sequence
<220> FEATURE:
<223> OTHER INFORMATION: Human IL12p35-P2A-IL12p40

<400> SEQUENCE: 5
atgtggcccc ctgggtcagc ctcccagcca ccgccctcac ctgccgcggc cacaggtctg 60
catccagcgg ctcgccctgt gtccctgcag tgccggctca gcatgtgtcc agcgcgcagc 120
ctcctccttg tggctaccct ggtcctcctg gaccacctca gtttggccag aaacctcccc 180
gtggccactc cagacccagg aatgttccca tgccttcacc actcccaaaa cctgctgagg 240
gccgtcagca acatgctcca gaaggccaga caaactctcg aattttaccc ttgcacttct 300
gaagagattg atcatgaaga tatcacaaaa gataaaacca gcacagtgga ggcctgttta 360
ccattggaat taaccaagaa tgagagttgc ctaaattcca gagagacctc tttcataact 420
aatgggagtt gcctggcctc cagaaagacc tcttttatga tggccctgtg ccttagtagt 480
atttatgaag acttgaagat gtaccaggtg gagttcaaga ccatgaatgc aaagcttctg 540
atggacccta agaggcaaat cttcctagat caaaacatgc tggcagttat tgatgagctg 600
atgcaggccc tgaatttcaa cagtgagact gtgccacaaa aatcctccct tgaagaaccg 660
gatttctaca agactaaaat caagctctgc atacttcttc atgctttcag aattcgggca 720
gtgactattg atagagtgat gagctatctg aatgcttccg cggccgcagg atctggggcc 780
accaactttt cattgctcaa gcaggcgggc gatgtggagg aaaaccctgg ccccggatcc 840
tgtcaccagc agttggtcat ctcttggttt tccctggttt ttctggcatc tcccctcgtg 900
gccatatggg aactgaagaa agatgtttat gtcgtagaat tggattggta tccggatgcc 960
cctggagaaa tggtggtcct cacctgtgac acccctgaag aagatggtat cacctggacc 1020
ttggaccaga gcagtgaggt cttaggctct ggcaaaaccc tgaccatcca agtcaaagag 1080
tttggagatg ctggccagta cacctgtcac aaaggaggcg aggttctaag ccattcgctc 1140
ctgctgcttc acaaaaagga agatggaatt tggtccactg atattttaaa ggaccagaaa 1200
gaacccaaaa ataagacctt tctaagatgc gaggccaaga attattctgg acgtttcacc 1260
tgctggtggc tgacgacaat cagtactgat ttgacattca gtgtcaaaag cagcagaggc 1320
tcttctgacc cccaaggggt gacgtgcgga gctgctacac tctctgcaga gagagtcaga 1380
ggggacaaca aggagtatga gtactcagtg gagtgccagg aggacagtgc ctgcccagct 1440
gctgaggaga gtctgcccat tgaggtcatg gtggatgccg ttcacaagct caagtatgaa 1500
aactacacca gcagcttctt catcagggac atcatcaaac ctgacccacc caagaacttg 1560
cagctgaagc cattaaagaa ttctcggcag gtggaggtca gctgggagta ccctgacacc 1620
tggagtactc cacattccta cttctccctg acattctgcg ttcaggtcca gggcaagagc 1680
aagagagaaa agaaagatag agtcttcacg gacaagacct cagccacggt catctgccgc 1740
aaaaatgcca gcattagcgt gcgggcccag gaccgctact atagctcatc ttggagcgaa 1800
tgggcatctg tgccctgcag ttag 1824

<210> SEQ ID NO 6
<211> LENGTH: 1794
<212> TYPE: DNA

-continued

<213> ORGANISM: Artificial Sequence
<220> FEATURE:
<223> OTHER INFORMATION: Mouse IL12p35-P2A-IL12p40

<400> SEQUENCE: 6
atggtcagcg ttccaacagc ctcaccctcg gcatccagca gctcctctca gtgccggtcc 60
agcatgtgtc aatcacgcta cctcctcttt ttggccaccc ttgccctcct aaaccacctc 120
agtttggcca gggtcattcc agtctctgga cctgccaggt gtcttagcca gtcccgaaac 180
ctgctgaaga ccacagatga catggtgaag acggccagag aaaaactgaa acattattcc 240
tgcactgctg aagacatcga tcatgaagac atcacacggg accaaaccag cacattgaag 300
acctgtttac cactggaact acacaagaac gagagttgcc tggctactag agagacttct 360
tccacaacaa gagggagctg cctgccccca cagaagacgt ctttgatgat gaccctgtgc 420
cttggtagca tctatgagga cttgaagatg taccagacag agttccaggc catcaacgca 480
gcacttcaga atcacaacca tcagcagatc attcttgaca agggcatgct ggtggccatc 540
gatgagctga tgcagtctct gaatcataat ggcgagactc tgcgccagaa acctcctgtg 600
ggagaagcag acccttacag agtgaaaatg aagctctgca tcctgcttca cgccttcagc 660
acccgcgtcg tgaccatcaa cagggtgatg ggctatctga gctccgccgc ggccgcagga 720
tctggggcca ccaacttttc attgctcaag caggcgggcg atgtggagga aaaccctggc 780
cccggatcct gtcctcagaa gctaaccatc tcctggtttg ccatcgtttt gctggtgtct 840
ccactcatgg ccatgtggga gctggagaaa gacgtttatg ttgtagaggt ggactggact 900
cccgatgccc ctggagaaac agtgaacctc acctgtgaca cgcctgaaga agatgacatc 960
acctggacct cagaccagag acatggagtc ataggctctg gaaagaccct gaccatcact 1020
gtcaaagagt ttcttgatgc tggccagtac acctgccaca aaggaggcga gactctgagc 1080
cactcacatc tgctgctcca caagaaggaa aatggaattt ggtccactga aattttaaag 1140
aatttcaaga acaagacttt cctgaagtgt gaagcaccaa attactccgg acggttcacg 1200
tgctcatggc tggtgcaaag aaacatggac ttgaagttca acatcaagag cagtagcagt 1260
tcccctgact ctcgggcagt gacatgtgga atggcgtctc tgtctgcaga gaaggtcaca 1320
ctggaccaaa gggactatga gaagtattca gtgtcctgcc aggaggatgt cacctgccca 1380
actgccgagg agaccctgcc cattgaactg gcgttggaag cacggcagca gaataaatat 1440
gagaactaca gcaccagctt cttcatcagg gacatcatca aaccagaccc gcccaagaac 1500
ttgcagatga agcctttgaa gaactcacag gtggaggtca gctgggagta ccctgactcc 1560
tggagcactc cccattccta cttctccctc aagttctttg ttcgaatcca gcgcaagaaa 1620
gaaaagatga aggagacaga ggaggggtgt aaccagaaag gtgcgttcct cgtagagaag 1680
acatctaccg aagtccaatg caaaggcggg aatgtctgcg tgcaagctca ggatcgctat 1740
tacaattcct catgcagcaa gtgggcatgt gttccctgca gggtccgatc ctag 1794

<210> SEQ ID NO 7
<211> LENGTH: 1734
<212> TYPE: DNA
<213> ORGANISM: Artificial Sequence
<220> FEATURE:
<223> OTHER INFORMATION: Canine IL12p35-P2A-IL12p40

<400> SEQUENCE: 7
atgtgcccgc cgcgcggcct cctccttgtg accatcctgg tcctgctaag ccacctggac 60
caccttactt gggccaggag cctccccaca gcctcaccga gcccaggaat attccagtgc 120

-continued ctcaaccact cccaaaacct gctgagagcc gtcagcaaca cgcttcagaa ggccagacaa 180
actctcgatt atattccctg cacttccgaa gagattgatc atgaagatat cacaaaggat 240
aaaaccagca cagtggaggc ctgcttacca ctggaattaa ccatgaatga gagttgcctg 300
gcttccagag agatttcttt gataactaac gggagttgcc tggcctctgg aaaggcctct 360
tttatgacgg tcctgtgcct tagcagcatc tatgaggact tgaagatgta ccagatggaa 420
ttcaaggcca tgaacgcaaa gcttttaatg gaccccaaga ggcagatttt tctggatcaa 480
aacatgttga cagctatcga tgagctgtta caggccctga atttcaacag tgtgactgtg 540
ccacagaaat cctcccttga agagccggac ttctacaaga ctaaaatcaa gctctgcata 600
cttcttcatg ctttcagaat tcgtgcggtg accatcgata gaatgatgag ttatctgaat 660
tcttccgcgg ccgcaggatc tggggccacc aacttttcat tgctcaagca ggcgggcgat 720
gtggaggaaa accctggccc cggatcccat cctcagcagt tggtcatctc ctggttttcc 780
ctcgttttgc tggcgtcttc cctcatgacc atatgggaac tggagaaaga tgtttatgtt 840
gtagagttgg actggcaccc tgatgccccc ggagaaatgg tggtcctcac ctgccatacc 900
cctgaagaag atgacatcac ttggacctca gcgcagagca gtgaagtcct aggttctggt 960
aaaactctga ccatccaagt caaagaattt ggagatgctg gccagtatac ctgccataaa 1020
ggaggcaagg ttctgagccg ctcactcctg ttgattcaca aaaaagaaga tggaatttgg 1080
tccactgata tcttaaagga acagaaagaa tccaaaaata agatttttct gaaatgtgag 1140
gcaaagaatt attctggacg tttcacatgc tggtggctga cggcaatcag tactgatttg 1200
aaattcagtg tcaaaagtag cagaggcttc tctgaccccc aaggggtgac atgtggagca 1260
gtgacacttt cagcagagag ggtcagagtg gacaacaggg attataagaa gtacacagtg 1320
gagtgtcagg aaggcagtgc ctgcccctct gccgaggaga gcctacccat cgaggtcgtg 1380
gtggatgcta ttcacaagct caagtatgaa aactacacca gcagcttctt catcagagac 1440
atcatcaaac cagacccacc cacaaacctg cagctgaagc cattgaaaaa ttctcggcac 1500
gtggaggtca gctgggaata ccccgacacc tggagcaccc cacattccta cttctccctg 1560
acattttgcg tacaggccca gggcaagaac aatagagaaa agaaagatag actctgcgtg 1620
gacaagacct cagccaaggt cgtgtgccac aaggatgcca agatccgcgt gcaagcccga 1680
gaccgctact atagttcatc ctggagcgac tgggcatctg tgtcctgcag ttag 1734

<210> SEQ ID NO 8
<211> LENGTH: 1368
<212> TYPE: DNA
<213> ORGANISM: Artificial Sequence
<220> FEATURE:
<223> OTHER INFORMATION: Human IL-15/IL-15Ra with P2A

<400> SEQUENCE: 8
atgagaattt cgaaaccaca tttgagaagt atttccatcc agtgctactt gtgtttactt 60
ctaaacagtc attttctaac tgaagctggc attcatgtct tcattttggg ctgtttcagt 120
gcagggcttc ctaaaacaga agccaactgg gtgaatgtaa taagtgattt gaaaaaaatt 180
gaggatctta ttcaatctat gcatattgat gctactttat atacggaaag tgatgttcac 240
cccagttgca aagtaacagc aatgaagtgc tttctcttgg agttacaagt tatttcactt 300
gagtccggag atgcaagtat tcatgataca gtagaaaatc tgatcatcct agcaaacaac 360
agtttgtctt ctaatgggaa tgtaacagaa tctggatgca aagaatgtga ggaactggag 420

-continued

```
gaaaagaata ttaaagagtt tttgcagagt tttgtacata ttgtccaaat gttcatcaac    480

acttctgcgg ccgcaggatc tggggccacc aacttttcat tgctcaagca ggcgggcgat    540

gtggaggaaa accctggccc cggatccgct ccccgccgcg cgagagggtg tcgaacgctt    600

ggtcttcctg cgttgctgct gttgttgttg ctcaggccgc ctgccacccg cggcataacc    660

tgccccccac cgatgagcgt ggagcacgca gacatctggg tcaaaagcta tagtctgtac    720

tctagggaaa ggtacatttg taacagtggg ttcaaaagaa aggctggcac atcatccctt    780

acagaatgcg tccttaacaa ggccaccaac gtcgcgcatt ggactacccc ttccctgaag    840

tgcatcagag atcctgcgct ggttcaccaa cgcccggccc ccccatctac agttacaacc    900

gctggtgtta cacctcagcc cgaatctctg tcaccttctg gcaaagaacc agcagcctcc    960

tccccaagtt ccaacaatac cgccgccact accgctgcta tcgttccagg ctcacaactg   1020

atgccgagta aatctcccag caccggtaca acagaaatct ctagtcatga gtcctcccat   1080

gggaccccgt cccagaccac tgctaaaaac tgggagctga ccgcctccgc tagccatcag   1140

ccgccccggg tgtacccaca ggggcactct gacaccactg tcgcgattag tactagcaca   1200

gtgctgttgt gcggactgtc tgccgtcagc ttgttggctt gctatctgaa atcccggcag   1260

acgccaccac tggccagcgt ggagatggaa gcaatggaag ctttgcctgt aacctggggg   1320

acgagctcac gggatgagga tctggagaac tgctcacatc acctgtaa                1368
```

<210> SEQ ID NO 9
<211> LENGTH: 455
<212> TYPE: PRT
<213> ORGANISM: Artificial Sequence
<220> FEATURE:
<223> OTHER INFORMATION: Human IL-15/IL-15Ra Fc P2A

<400> SEQUENCE: 9

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser Ala Ala Ala Gly Ser Gly Ala Thr Asn Phe Ser Leu Leu Lys
                165                 170                 175

Gln Ala Gly Asp Val Glu Glu Asn Pro Gly Pro Gly Ser Ala Pro Arg
            180                 185                 190

Arg Ala Arg Gly Cys Arg Thr Leu Gly Leu Pro Ala Leu Leu Leu Leu
```

-continued

```
        195                 200                 205

Leu Leu Leu Arg Pro Pro Ala Thr Arg Gly Ile Thr Cys Pro Pro Pro
    210                 215                 220

Met Ser Val Glu His Ala Asp Ile Trp Val Lys Ser Tyr Ser Leu Tyr
225                 230                 235                 240

Ser Arg Glu Arg Tyr Ile Cys Asn Ser Gly Phe Lys Arg Lys Ala Gly
                245                 250                 255

Thr Ser Ser Leu Thr Glu Cys Val Leu Asn Lys Ala Thr Asn Val Ala
            260                 265                 270

His Trp Thr Thr Pro Ser Leu Lys Cys Ile Arg Asp Pro Ala Leu Val
        275                 280                 285

His Gln Arg Pro Ala Pro Pro Ser Thr Val Thr Thr Ala Gly Val Thr
    290                 295                 300

Pro Gln Pro Glu Ser Leu Ser Pro Ser Gly Lys Glu Pro Ala Ala Ser
305                 310                 315                 320

Ser Pro Ser Ser Asn Asn Thr Ala Ala Thr Thr Ala Ala Ile Val Pro
                325                 330                 335

Gly Ser Gln Leu Met Pro Ser Lys Ser Pro Ser Thr Gly Thr Thr Glu
            340                 345                 350

Ile Ser Ser His Glu Ser Ser His Gly Thr Pro Ser Gln Thr Thr Ala
        355                 360                 365

Lys Asn Trp Glu Leu Thr Ala Ser Ala Ser His Gln Pro Pro Gly Val
    370                 375                 380

Tyr Pro Gln Gly His Ser Asp Thr Thr Val Ala Ile Ser Thr Ser Thr
385                 390                 395                 400

Val Leu Leu Cys Gly Leu Ser Ala Val Ser Leu Leu Ala Cys Tyr Leu
                405                 410                 415

Lys Ser Arg Gln Thr Pro Pro Leu Ala Ser Val Glu Met Glu Ala Met
            420                 425                 430

Glu Ala Leu Pro Val Thr Trp Gly Thr Ser Ser Arg Asp Glu Asp Leu
        435                 440                 445

Glu Asn Cys Ser His His Leu
    450                 455
```

<210> SEQ ID NO 10
<211> LENGTH: 2070
<212> TYPE: DNA
<213> ORGANISM: Artificial Sequence
<220> FEATURE:
<223> OTHER INFORMATION: Human IL-15/IL-15Ra-Fc with P2A

<400> SEQUENCE: 10

```
atgagaattt cgaaaccaca tttgagaagt atttccatcc agtgctactt gtgtttactt      60

ctaaacagtc attttctaac tgaagctggc attcatgtct tcattttggg ctgtttcagt     120

gcagggcttc ctaaaacaga agccaactgg gtgaatgtaa taagtgattt gaaaaaaatt     180

gaggatctta ttcaatctat gcatattgat gctactttat atacggaaag tgatgttcac     240

cccagttgca aagtaacagc aatgaagtgc tttctcttgg agttacaagt tatttcactt     300

gagtccggag atgcaagtat tcatgataca gtagaaaatc tgatcatcct agcaaacaac     360

agtttgtctt ctaatgggaa tgtaacagaa tctggatgca aagaatgtga ggaactggag     420

gaaaagaata ttaaagagtt tttgcagagt tttgtacata ttgtccaaat gttcatcaac     480

acttctgcgg ccgcaggatc tggggccacc aacttttcat tgctcaagca ggcgggcgat     540

gtggaggaaa accctggccc cggatccgct ccccgccgcg cgagagggtg tcgaacgctt     600
```

```
ggtcttcctg cgttgctgct gttgttgttg ctcaggccgc ctgccacccg cggcataacc    660

tgccccccac cgatgagcgt ggagcacgca gacatctggg tcaaaagcta tagtctgtac    720

tctagggaaa ggtacatttg taacagtggg ttcaaaagaa aggctggcac atcatccctt    780

acagaatgcg tccttaacaa ggccaccaac gtcgcgcatt ggactacccc ttccctgaag    840

tgcatcagag atcctgcgct ggttcaccaa cgcccggccc ccccatctac agttacaacc    900

gctggtgtta cacctcagcc cgaatctctg tcaccttctg gcaaagaacc agcagcctcc    960

tccccaagtt ccaacaatac cgccgccact accgctgcta tcgttccagg ctcacaactg   1020

atgccgagta aatctcccag caccggtaca acagaaatct ctagtcatga gtcctcccat   1080

gggaccccgt cccagaccac tgctaaaaac tgggagctga ccgcctccgc tagccatcag   1140

ccgcccgggg tgtacccaca ggggcactct gacaccactg tcgcgattag tactagcaca   1200

gtgctgttgt gcggactgtc tgccgtcagc ttgttggctt gctatctgaa atcccggcag   1260

acgccaccac tggccagcgt ggagatggaa gcaatggaag ctttgcctgt aacctggggg   1320

acgagctcac gggatgagga tctggagaac tgctcacatc acctgggaag atctggcagt   1380

tctggggaca aaactcacac atgcccaccg tgcccagcac ctgaactcct ggggggaccg   1440

tcagtcttcc tcttcccccc aaaacccaag gacaccctca tgatctcccg gacccctgag   1500

gtcacatgcg tggtggtgga cgtgagccac gaagaccctg aggtcaagtt caactggtac   1560

gtggacggcg tggaggtgca taatgccaag acaaagccgc gggaggagca gtacaacagc   1620

acgtaccgtg tggtcagcgt cctcaccgtc ctgcaccagg actggctgaa tggcaaggag   1680

tacaagtgca aggtctccaa caaagccctc ccagccccca tcgagaaaac catctccaaa   1740

gccaaagggc agccccgaga accacaggtc tacaccctgc ccccatcccg ggaggagatg   1800

accaagaacc aggtcagcct gacctgcctg gtcaaaggct tctatcccag cgacatcgcc   1860

gtggagtggg agagcaatgg gcagccggag aacaactaca agaccacgcc tcccgtgctg   1920

gactccgacg gctccttctt cctctacagc aagctcaccg tggacaagag caggtggcag   1980

caggggaacg tcttctcatg ctccgtgatg cacgaggctc tgcacaacca ctacacgcag   2040

aagagcctct ccctgtctcc gggtaaatag                                    2070
```

<210> SEQ ID NO 11
<211> LENGTH: 689
<212> TYPE: PRT
<213> ORGANISM: Artificial Sequence
<220> FEATURE:
<223> OTHER INFORMATION: Human IL-15/IL-15Ra-Fc with P2A

<400> SEQUENCE: 11

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95
```

-continued

```
Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser Ala Ala Ala Gly Ser Gly Ala Thr Asn Phe Ser Leu Leu Lys
                165                 170                 175

Gln Ala Gly Asp Val Glu Glu Asn Pro Gly Pro Gly Ser Ala Pro Arg
            180                 185                 190

Arg Ala Arg Gly Cys Arg Thr Leu Gly Leu Pro Ala Leu Leu Leu Leu
        195                 200                 205

Leu Leu Leu Arg Pro Pro Ala Thr Arg Gly Ile Thr Cys Pro Pro Pro
    210                 215                 220

Met Ser Val Glu His Ala Asp Ile Trp Val Lys Ser Tyr Ser Leu Tyr
225                 230                 235                 240

Ser Arg Glu Arg Tyr Ile Cys Asn Ser Gly Phe Lys Arg Lys Ala Gly
                245                 250                 255

Thr Ser Ser Leu Thr Glu Cys Val Leu Asn Lys Ala Thr Asn Val Ala
            260                 265                 270

His Trp Thr Thr Pro Ser Leu Lys Cys Ile Arg Asp Pro Ala Leu Val
        275                 280                 285

His Gln Arg Pro Ala Pro Pro Ser Thr Val Thr Thr Ala Gly Val Thr
    290                 295                 300

Pro Gln Pro Glu Ser Leu Ser Pro Ser Gly Lys Glu Pro Ala Ala Ser
305                 310                 315                 320

Ser Pro Ser Ser Asn Asn Thr Ala Ala Thr Thr Ala Ala Ile Val Pro
                325                 330                 335

Gly Ser Gln Leu Met Pro Ser Lys Ser Pro Ser Thr Gly Thr Thr Glu
            340                 345                 350

Ile Ser Ser His Glu Ser Ser His Gly Thr Pro Ser Gln Thr Thr Ala
        355                 360                 365

Lys Asn Trp Glu Leu Thr Ala Ser Ala Ser His Gln Pro Pro Gly Val
    370                 375                 380

Tyr Pro Gln Gly His Ser Asp Thr Thr Val Ala Ile Ser Thr Ser Thr
385                 390                 395                 400

Val Leu Leu Cys Gly Leu Ser Ala Val Ser Leu Leu Ala Cys Tyr Leu
                405                 410                 415

Lys Ser Arg Gln Thr Pro Pro Leu Ala Ser Val Glu Met Glu Ala Met
            420                 425                 430

Glu Ala Leu Pro Val Thr Trp Gly Thr Ser Ser Arg Asp Glu Asp Leu
        435                 440                 445

Glu Asn Cys Ser His His Leu Gly Arg Ser Gly Ser Ser Gly Asp Lys
    450                 455                 460

Thr His Thr Cys Pro Pro Cys Pro Ala Pro Glu Leu Leu Gly Gly Pro
465                 470                 475                 480

Ser Val Phe Leu Phe Pro Pro Lys Pro Lys Asp Thr Leu Met Ile Ser
                485                 490                 495

Arg Thr Pro Glu Val Thr Cys Val Val Val Asp Val Ser His Glu Asp
            500                 505                 510

Pro Glu Val Lys Phe Asn Trp Tyr Val Asp Gly Val Glu Val His Asn
```

```
        515                 520                 525

Ala Lys Thr Lys Pro Arg Glu Glu Gln Tyr Asn Ser Thr Tyr Arg Val
    530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Pro Ala Pro Ile Glu Lys
                565                 570                 575

Thr Ile Ser Lys Ala Lys Gly Gln Pro Arg Glu Pro Gln Val Tyr Thr
            580                 585                 590

Leu Pro Pro Ser Arg Glu Glu Met Thr Lys Asn Gln Val Ser Leu Thr
        595                 600                 605

Cys Leu Val Lys Gly Phe Tyr Pro Ser Asp Ile Ala Val Glu Trp Glu
    610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
                645                 650                 655

Ser Arg Trp Gln Gln Gly Asn Val Phe Ser Cys Ser Val Met His Glu
            660                 665                 670

Ala Leu His Asn His Tyr Thr Gln Lys Ser Leu Ser Leu Ser Pro Gly
        675                 680                 685

Lys
```

<210> SEQ ID NO 12
<211> LENGTH: 501
<212> TYPE: DNA
<213> ORGANISM: Artificial Sequence
<220> FEATURE:
<223> OTHER INFORMATION: Human interferon gamma

<400> SEQUENCE: 12

```
atgaaatata caagttatat cttggctttt cagctctgca tcgttttggg ttctcttggc     60

tgttactgcc aggacccata tgtaaaagaa gcagaaaacc ttaagaaata ttttaatgca    120

ggtcattcag atgtagcgga taatggaact cttttcttag gcattttgaa gaattggaaa    180

gaggagagtg acagaaaaat aatgcagagc caaattgtct ccttttactt caaacttttt    240

aaaaacttta aagatgacca gagcatccaa aagagtgtgg agaccatcaa ggaagacatg    300

aatgtcaagt ttttcaatag caacaaaaag aaacgagatg acttcgaaaa gctgactaat    360

tattcggtaa ctgacttgaa tgtccaacgc aaagcaatac atgaactcat ccaagtgatg    420

gctgaactgt cgccagcagc taaaacaggg aagcgaaaaa ggagtcagat gctgtttcga    480

ggtcgaagag catcccagta a                                              501
```

<210> SEQ ID NO 13
<211> LENGTH: 1101
<212> TYPE: DNA
<213> ORGANISM: Artificial Sequence
<220> FEATURE:
<223> OTHER INFORMATION: hFlt3L-NY-ESO-1 full length

<400> SEQUENCE: 13

```
atggatgcta tgaaacgagg actgtgttgt gtgttgcttc tgtgtggagc ggtttttgtg     60

agtcccactc aggattgcag cttccagcat tcacccatat catcagattt tgcagtaaag    120

atcagggaac tctccgatta tctccttcaa gactaccccg taacagtggc ctccaatttg    180

caagacgaag agctttgtgg tgccctctgg cggctcgttt tggcccaaag gtggatggaa    240
```

```
cggcttaaga cagtcgctgg cagcaagatg caagggttgc tcgaacgagt caatacagag    300

atccattttg taaccaagtg tgcatttcaa ccgccgccaa gctgccttcg ctttgttcag    360

acgaatataa gtagactgtt gcaggaaacc tccgagcaac tcgtagccct gaagccctgg    420

attacacggc aaaatttcag tcggtgcctt gagcttcagt gtcagcctga tagtagtacc    480

ttgcctccgc catggtcccc caggcctctt gaagctacag ctccgacagc ccctcagccg    540

ggcagtagtg gtagttctgg acaagcggag ggaagaggga cggggggctc aacgggagac    600

gccgatggac ctggcggtcc tggtatcccg gacggcccag gtggcaatgc tggcggtcca    660

ggcgaggctg gtgcaactgg tggacgcggg ccgcggggcg cgggtgctgc acgggcaagt    720

ggccctgggg gcggcgctcc tcggggtccg catgggggtg cagccagtgg actcaatggg    780

tgctgcagat gcggcgcgag aggtccggaa agtcgattgc ttgaatttta cctcgcaatg    840

cccttcgcaa cgccgatgga ggctgaactg gccaggcgca gtcttgccca ggacgcgcct    900

cccttgccag tgcccggtgt gctgcttaaa gagttcactg tttctggtaa catcttgacg    960

attcgcctga cggcagcaga ccatcgacaa ctccagctct ccatctcttc atgtcttcag   1020

cagctctcac tgttgatgtg gatcacacag tgtttcttgc ccgtgtttct cgcacagcct   1080

ccatctggac agagaaggta a                                             1101
```

```
<210> SEQ ID NO 14
<211> LENGTH: 366
<212> TYPE: PRT
<213> ORGANISM: Artificial Sequence
<220> FEATURE:
<223> OTHER INFORMATION: hFlt3L-NY-ESO-1 full length

<400> SEQUENCE: 14

Met Asp Ala Met Lys Arg Gly Leu Cys Cys Val Leu Leu Leu Cys Gly
1               5                   10                  15

Ala Val Phe Val Ser Pro Thr Gln Asp Cys Ser Phe Gln His Ser Pro
            20                  25                  30

Ile Ser Ser Asp Phe Ala Val Lys Ile Arg Glu Leu Ser Asp Tyr Leu
        35                  40                  45

Leu Gln Asp Tyr Pro Val Thr Val Ala Ser Asn Leu Gln Asp Glu Glu
    50                  55                  60

Leu Cys Gly Ala Leu Trp Arg Leu Val Leu Ala Gln Arg Trp Met Glu
65                  70                  75                  80

Arg Leu Lys Thr Val Ala Gly Ser Lys Met Gln Gly Leu Leu Glu Arg
                85                  90                  95

Val Asn Thr Glu Ile His Phe Val Thr Lys Cys Ala Phe Gln Pro Pro
            100                 105                 110

Pro Ser Cys Leu Arg Phe Val Gln Thr Asn Ile Ser Arg Leu Leu Gln
        115                 120                 125

Glu Thr Ser Glu Gln Leu Val Ala Leu Lys Pro Trp Ile Thr Arg Gln
    130                 135                 140

Asn Phe Ser Arg Cys Leu Glu Leu Gln Cys Gln Pro Asp Ser Ser Thr
145                 150                 155                 160

Leu Pro Pro Pro Trp Ser Pro Arg Pro Leu Glu Ala Thr Ala Pro Thr
                165                 170                 175

Ala Pro Gln Pro Gly Ser Ser Gly Ser Ser Gly Gln Ala Glu Gly Arg
            180                 185                 190

Gly Thr Gly Gly Ser Thr Gly Asp Ala Asp Gly Pro Gly Gly Pro Gly
        195                 200                 205
```

```
Ile Pro Asp Gly Pro Gly Gly Asn Ala Gly Gly Pro Gly Glu Ala Gly
    210                 215                 220

Ala Thr Gly Gly Arg Gly Pro Arg Gly Ala Gly Ala Ala Arg Ala Ser
225                 230                 235                 240

Gly Pro Gly Gly Gly Ala Pro Arg Gly Pro His Gly Gly Ala Ala Ser
                245                 250                 255

Gly Leu Asn Gly Cys Cys Arg Cys Gly Ala Arg Gly Pro Glu Ser Arg
            260                 265                 270

Leu Leu Glu Phe Tyr Leu Ala Met Pro Phe Ala Thr Pro Met Glu Ala
        275                 280                 285

Glu Leu Ala Arg Arg Ser Leu Ala Gln Asp Ala Pro Pro Leu Pro Val
    290                 295                 300

Pro Gly Val Leu Leu Lys Glu Phe Thr Val Ser Gly Asn Ile Leu Thr
305                 310                 315                 320

Ile Arg Leu Thr Ala Ala Asp His Arg Gln Leu Gln Leu Ser Ile Ser
                325                 330                 335

Ser Cys Leu Gln Gln Leu Ser Leu Leu Met Trp Ile Thr Gln Cys Phe
            340                 345                 350

Leu Pro Val Phe Leu Ala Gln Pro Pro Ser Gly Gln Arg Arg
        355                 360                 365
```

<210> SEQ ID NO 15
<211> LENGTH: 867
<212> TYPE: DNA
<213> ORGANISM: Artificial Sequence
<220> FEATURE:
<223> OTHER INFORMATION: hFlt3L-NY-ESO-1 80-180aa

<400> SEQUENCE: 15

```
atggatgcta tgaaacgagg actgtgttgt gtgttgcttc tgtgtggagc ggtttttgtg      60

agtcccactc aggattgcag cttccagcat tcacccatat catcagattt tgcagtaaag     120

atcagggaac tctccgatta tctccttcaa gactaccccg taacagtggc ctccaatttg     180

caagacgaag agctttgtgg tgccctctgg cggctcgttt tggcccaaag gtggatggaa     240

cggcttaaga cagtcgctgg cagcaagatg caagggttgc tcgaacgagt caatacagag     300

atccattttg taaccaagtg tgcatttcaa ccgccgccaa gctgccttcg ctttgttcag     360

acgaatataa gtagactgtt gcaggaaacc tccgagcaac tcgtagccct gaagccctgg     420

attacacggc aaaatttcag tcggtgcctt gagcttcagt gtcagcctga tagtagtacc     480

ttgcctccgc catggtcccc caggcctctt gaagctacag ctccgacagc ccctcagccg     540

ggcagtagtg gtagttctgg agccaggggg ccggagagcc gcctgcttga gttctacctc     600

gccatgcctt tcgcgacacc catggaagca gagctggccc gcaggagcct ggcccaggat     660

gccccaccgc ttcccgtgcc aggggtgctt ctgaaggagt tcactgtgtc cggcaacata     720

ctgactatcc gactgactgc tgcagaccac cgccaactgc agctctccat cagctcctgt     780

ctccagcagc tttccctgtt gatgtggatc acgcagtgct ttctgcccgt gtttttggct     840

cagcctccct cagggcagag gcgctaa                                         867
```

<210> SEQ ID NO 16
<211> LENGTH: 288
<212> TYPE: PRT
<213> ORGANISM: Artificial Sequence
<220> FEATURE:
<223> OTHER INFORMATION: hFlt3L-NY-ESO-1 80-180aa

<400> SEQUENCE: 16

```
Met Asp Ala Met Lys Arg Gly Leu Cys Cys Val Leu Leu Leu Cys Gly
1               5                   10                  15

Ala Val Phe Val Ser Pro Thr Gln Asp Cys Ser Phe Gln His Ser Pro
            20                  25                  30

Ile Ser Ser Asp Phe Ala Val Lys Ile Arg Glu Leu Ser Asp Tyr Leu
        35                  40                  45

Leu Gln Asp Tyr Pro Val Thr Val Ala Ser Asn Leu Gln Asp Glu Glu
    50                  55                  60

Leu Cys Gly Ala Leu Trp Arg Leu Val Leu Ala Gln Arg Trp Met Glu
65                  70                  75                  80

Arg Leu Lys Thr Val Ala Gly Ser Lys Met Gln Gly Leu Leu Glu Arg
                85                  90                  95

Val Asn Thr Glu Ile His Phe Val Thr Lys Cys Ala Phe Gln Pro Pro
            100                 105                 110

Pro Ser Cys Leu Arg Phe Val Gln Thr Asn Ile Ser Arg Leu Leu Gln
        115                 120                 125

Glu Thr Ser Glu Gln Leu Val Ala Leu Lys Pro Trp Ile Thr Arg Gln
    130                 135                 140

Asn Phe Ser Arg Cys Leu Glu Leu Gln Cys Gln Pro Asp Ser Ser Thr
145                 150                 155                 160

Leu Pro Pro Pro Trp Ser Pro Arg Pro Leu Glu Ala Thr Ala Pro Thr
                165                 170                 175

Ala Pro Gln Pro Gly Ser Ser Gly Ser Ser Gly Ala Arg Gly Pro Glu
            180                 185                 190

Ser Arg Leu Leu Glu Phe Tyr Leu Ala Met Pro Phe Ala Thr Pro Met
        195                 200                 205

Glu Ala Glu Leu Ala Arg Arg Ser Leu Ala Gln Asp Ala Pro Pro Leu
    210                 215                 220

Pro Val Pro Gly Val Leu Leu Lys Glu Phe Thr Val Ser Gly Asn Ile
225                 230                 235                 240

Leu Thr Ile Arg Leu Thr Ala Ala Asp His Arg Gln Leu Gln Leu Ser
                245                 250                 255

Ile Ser Ser Cys Leu Gln Gln Leu Ser Leu Leu Met Trp Ile Thr Gln
            260                 265                 270

Cys Phe Leu Pro Val Phe Leu Ala Gln Pro Pro Ser Gly Gln Arg Arg
        275                 280                 285
```

<210> SEQ ID NO 17
<211> LENGTH: 828
<212> TYPE: DNA
<213> ORGANISM: Artificial Sequence
<220> FEATURE:
<223> OTHER INFORMATION: hFlt3L-NY-ESO various peptides

<400> SEQUENCE: 17

```
atggatgcta tgaaacgagg actgtgttgt gtgttgcttc tgtgtggagc ggtttttgtg     60

agtcccactc aggattgcag cttccagcat tcacccatat catcagattt tgcagtaaag    120

atcagggaac tctccgatta tctccttcaa gactaccccg taacagtggc ctccaatttg    180

caagacgaag agctttgtgg tgccctctgg cggctcgttt tggcccaaag gtggatggaa    240

cggcttaaga cagtcgctgg cagcaagatg caagggttgc tcgaacgagt caatacagag    300

atccattttg taaccaagtg tgcatttcaa ccgccgccaa gctgccttcg ctttgttcag    360

acgaatataa gtagactgtt gcaggaaacc tccgagcaac tcgtagccct gaagccctgg    420
```

```
attacacggc aaaatttcag tcggtgcctt gagcttcagt gtcagcctga tagtagtacc    480

ttgcctccgc catggtcccc caggcctctt gaagctacag ctccgacagc ccctcagccg    540

ggcagtagtg gtagttctgg aaggggacct gagtcaaggc tgctcgaatt ctacttggca    600

atgccttttg cgacccctat gctgcttgaa ttttaccttg caatgccctt cgccaccccc    660

atggaagcag aactcgcccg gcgatccttg gctcagagcc tcttgatgtg gataactcaa    720

tgcagtttgt tgatgtggat aactcaatgc tttctgcccg ttttttggat aacgcaatgc    780

tttctcccgg tgtttctcgc tcaaccccct agcgggcaaa ggcgctaa                 828


<210> SEQ ID NO 18
<211> LENGTH: 275
<212> TYPE: PRT
<213> ORGANISM: Artificial Sequence
<220> FEATURE:
<223> OTHER INFORMATION: hFlt3L-NY-ESO various peptides

<400> SEQUENCE: 18

Met Asp Ala Met Lys Arg Gly Leu Cys Cys Val Leu Leu Leu Cys Gly
1               5                   10                  15

Ala Val Phe Val Ser Pro Thr Gln Asp Cys Ser Phe Gln His Ser Pro
            20                  25                  30

Ile Ser Ser Asp Phe Ala Val Lys Ile Arg Glu Leu Ser Asp Tyr Leu
        35                  40                  45

Leu Gln Asp Tyr Pro Val Thr Val Ala Ser Asn Leu Gln Asp Glu Glu
    50                  55                  60

Leu Cys Gly Ala Leu Trp Arg Leu Val Leu Ala Gln Arg Trp Met Glu
65                  70                  75                  80

Arg Leu Lys Thr Val Ala Gly Ser Lys Met Gln Gly Leu Leu Glu Arg
                85                  90                  95

Val Asn Thr Glu Ile His Phe Val Thr Lys Cys Ala Phe Gln Pro Pro
            100                 105                 110

Pro Ser Cys Leu Arg Phe Val Gln Thr Asn Ile Ser Arg Leu Leu Gln
        115                 120                 125

Glu Thr Ser Glu Gln Leu Val Ala Leu Lys Pro Trp Ile Thr Arg Gln
    130                 135                 140

Asn Phe Ser Arg Cys Leu Glu Leu Gln Cys Gln Pro Asp Ser Ser Thr
145                 150                 155                 160

Leu Pro Pro Pro Trp Ser Pro Arg Pro Leu Glu Ala Thr Ala Pro Thr
                165                 170                 175

Ala Pro Gln Pro Gly Ser Ser Gly Ser Ser Gly Arg Gly Pro Glu Ser
            180                 185                 190

Arg Leu Leu Glu Phe Tyr Leu Ala Met Pro Phe Ala Thr Pro Met Leu
        195                 200                 205

Leu Glu Phe Tyr Leu Ala Met Pro Phe Ala Thr Pro Met Glu Ala Glu
    210                 215                 220

Leu Ala Arg Arg Ser Leu Ala Gln Ser Leu Leu Met Trp Ile Thr Gln
225                 230                 235                 240

Cys Ser Leu Leu Met Trp Ile Thr Gln Cys Phe Leu Pro Val Phe Trp
                245                 250                 255

Ile Thr Gln Cys Phe Leu Pro Val Phe Leu Ala Gln Pro Pro Ser Gly
            260                 265                 270

Gln Arg Arg
        275
```

-continued

<210> SEQ ID NO 19
<211> LENGTH: 66
<212> TYPE: DNA
<213> ORGANISM: Artificial Sequence
<220> FEATURE:
<223> OTHER INFORMATION: Translational modifier: Exon skipping motif P2A

<400> SEQUENCE: 19
ggatctgggg ccaccaactt ttcattgctc aagcaggcgg gcgatgtgga ggaaaaccct 60
ggcccc 66

<210> SEQ ID NO 20
<211> LENGTH: 63
<212> TYPE: DNA
<213> ORGANISM: Artificial Sequence
<220> FEATURE:
<223> OTHER INFORMATION: Translational modifier: Exon skipping motif T2A

<400> SEQUENCE: 20
ggaagcggag agggcagagg aagtctgcta acatgcggtg acgtcgagga gaatcctggc 60
cca 63

<210> SEQ ID NO 21
<211> LENGTH: 69
<212> TYPE: DNA
<213> ORGANISM: Artificial Sequence
<220> FEATURE:
<223> OTHER INFORMATION: Translational modifier: Exon skipping motif E2A

<400> SEQUENCE: 21
ggaagcggac agtgtactaa ttatgctctc ttgaaattgg ctggagatgt tgagagcaac 60
cctggacct 69

<210> SEQ ID NO 22
<211> LENGTH: 75
<212> TYPE: DNA
<213> ORGANISM: Artificial Sequence
<220> FEATURE:
<223> OTHER INFORMATION: Translational modifier: Exon skipping motif F2A

<400> SEQUENCE: 22
ggcagcggcg tgaagcagac cctgaacttc gacctgctga agctggccgg cgacgtggag 60
agcaaccccg gcccc 75

<210> SEQ ID NO 23
<211> LENGTH: 568
<212> TYPE: DNA
<213> ORGANISM: Artificial Sequence
<220> FEATURE:
<223> OTHER INFORMATION: Translational modifier: Internal Ribosomal
      Entry Sequence (IRES)

<400> SEQUENCE: 23
tccgcccccc cccctaacgt tactggccga agccgcttgg aataaggccg gtgtgcgttt 60
gtctatatgt tattttccac catattgccg tcttttggca atgtgagggc ccggaaacct 120
ggccctgtct tcttgacgag cattcctagg ggtctttccc ctctcgccaa aggaatgcaa 180
ggtctgttga atgtcgtgaa ggaagcagtt cctctggaag cttcttgaag acaaacaacg 240
tctgtagcga ccctttgcag gcagcggaac cccccacctg gcgacaggtg cctctgcggc 300
caaaagccac gtgtataaga tacacctgca aaggcggcac aaccccagtg ccacgttgtg 360

-continued

```
agttggatag ttgtggaaag agtcaaatgg ctctcctcaa gcgtattcaa caaggggctg    420

aaggatgccc agaaggtacc ccattgtatg ggatctgatc tggggcctcg gtgcacatgc    480

tttacatgtg tttagtcgag gttaaaaaaa cgtctaggcc ccccgaacca cggggacgtg    540

gttttccttt gaaaaacacg atgataat                                       568


<210> SEQ ID NO 24
<211> LENGTH: 90
<212> TYPE: DNA
<213> ORGANISM: Artificial Sequence
<220> FEATURE:
<223> OTHER INFORMATION: Ovalbumin aa 241-270

<400> SEQUENCE: 24

tccatgcttg tgttgttgcc tgacgaggtg tccgggttgg agcagttgga aagcataata     60

aacttcgaga agttgactga atggacataa                                      90


<210> SEQ ID NO 25
<211> LENGTH: 29
<212> TYPE: PRT
<213> ORGANISM: Artificial Sequence
<220> FEATURE:
<223> OTHER INFORMATION: Ovalbumin aa 241-270

<400> SEQUENCE: 25

Ser Met Leu Val Leu Leu Pro Asp Glu Val Ser Gly Leu Glu Gln Leu
1               5                   10                  15

Glu Ser Ile Ile Asn Phe Glu Lys Leu Thr Glu Trp Thr
            20                  25
```